(12) United States Patent
Moellering et al.

(10) Patent No.: US 12,048,686 B2
(45) Date of Patent: Jul. 30, 2024

(54) COMPOSITIONS AND METHODS FOR ACTIVATING NRF2-DEPENDENT GENE EXPRESSION

(71) Applicant: The University of Chicago, Chicago, IL (US)

(72) Inventors: Raymond Moellering, Chicago, IL (US); John Coukos, Chicago, IL (US); Gihoon Lee, Chicago, IL (US); Jae Won Chang, Chicago, IL (US); Gokhan Mutlu, Chicago, IL (US)

(73) Assignee: The University of Chicago, Chicago, IL (US)

( * ) Notice: Subject to any disclaimer, the term of this patent is extended or adjusted under 35 U.S.C. 154(b) by 377 days.

(21) Appl. No.: 17/309,017

(22) PCT Filed: Oct. 14, 2019

(86) PCT No.: PCT/US2019/056105
§ 371 (c)(1),
(2) Date: Apr. 14, 2021

(87) PCT Pub. No.: WO2020/081446
PCT Pub. Date: Apr. 23, 2020

(65) Prior Publication Data
US 2022/0031656 A1 Feb. 3, 2022

Related U.S. Application Data

(60) Provisional application No. 62/745,454, filed on Oct. 14, 2018.

(51) Int. Cl.
*A61K 31/381* (2006.01)

(52) U.S. Cl.
CPC ................... *A61K 31/381* (2013.01)

(58) Field of Classification Search
CPC .................................................. A61K 31/381
See application file for complete search history.

(56) References Cited

U.S. PATENT DOCUMENTS

| | | | | |
|---|---|---|---|---|
| 2010/0047368 A1* | 2/2010 | Biswal | ............ | A61K 48/00 435/325 |
| 2011/0250300 A1* | 10/2011 | Biswal | ............ | A61P 25/00 435/375 |
| 2014/0012018 A1 | 1/2014 | Miyada et al. | | |
| 2016/0130258 A1 | 5/2016 | Lairson et al. | | |
| 2018/0346456 A1* | 12/2018 | Lander | ............ | A61P 35/00 |

FOREIGN PATENT DOCUMENTS

| | | |
|---|---|---|
| CN | 107814792 | 3/2018 |
| WO | WO 2012/045196 | 4/2012 |
| WO | WO 2016/111991 | 7/2016 |

OTHER PUBLICATIONS

Kinase Inhibitors, Methods in Molecular Biology 795 (B. Kuster ed., 2012).*
Canning et al., "Structural basis of Keap1 interactions with Nrf2" *Free Radical Biology and Medicine* 2015, 88, 101-107.
Database Registry [Online] Chemical Abstracts Service; Sep. 24, 2010, XP055913058, Database accession No. 1242814-78-3 (Abstract only).
Database Registry [Online] Chemical Abstracts Service; Sep. 26, 2010, XP055913051, Database accession No. 1242825-17-7 (Abstract only).
Database Registry [Online] Chemical Abstracts Service; Sep. 26, 2010, XP055913048, Database accession No. 1242830-92-7 (Abstract only).
Database Registry [Online] Chemical Abstracts Service; Sep. 26, 2010, XP055913046, Database accession No. 1242832-96-7 (Abstract only).
Database Registry [Online] Chemical Abstracts Service; Sep. 29, 2010, XP055913042, Database accession No. 1243688-98-3 (Abstract only).
Database Registry [Online] Chemical Abstracts Service; Sep. 29, 2010, XP055913035, Database accession No. 1243816-57-0 (Abstract only).
Database Registry [Online] Chemical Abstracts Service; Jun. 30, 2011, XP055913037, Database accession No. 1311000-37-9 (Abstract only).
Database Registry [Online] Chemical Abstracts Service; Sep. 30, 2010, XP055913033, Database accession No. 1243822-21-0 (Abstract only).
Extended European Search Report issued in Corresponding European Application No. 19873293.5, dated Aug. 5, 2022.
Gupta et al., "In silico screening for identification of novel HIV-1 integrase inhibitors using QSAR and docking methodologies" *Med Chem Res* 2013, 22:5014-5028.
Bollong et al., "A metabolite-derived protein modification integrates glycolysis with KEAP1-NRF2 signaling" *Nature* 2018, 562(7728), 1-37.
Cleasby et al., "Structure of the BTB domain of Keap1 and its interaction with the triterpenoid antagonist CDDO." *PloS one* 2014, 9, e98896.
Hur et al., "A small-molecule inducer of the antioxidant response element." *Chemistry & biology* 2010, 17, 537-547.
International Search Report and Written Opinion issued in Corresponding PCT Application No. PCT/US2019/056105, dated Feb. 10, 2020.
Jaramillo et al., "The emerging role of the Nrf2-Keap1 signaling pathway in cancer." *Genes & development* 2013, 27, 2179-2191.
Khor et al., "Nrf2-deficient mice have an increased susceptibility to dextran sulfate sodium-induced colitis." *Cancer research* 2006, 66, 11580-11584.

(Continued)

Primary Examiner — Bong-Sook Baek
(74) Attorney, Agent, or Firm — Norton Rose Fulbright US LLP

(57) ABSTRACT

Embodiments are directed to a series of novel small molecule activators of NRF2 dependent gene expression that are evaluated in an effort to develop therapeutic methods against diseases with deregulated KEAP1-NRF2 signaling.

4 Claims, 47 Drawing Sheets

Specification includes a Sequence Listing.

(56) References Cited

OTHER PUBLICATIONS

Scannevin et al., "Fumarates promote cytoprotection of central nervous system cells against oxidative stress via the nuclear factor (erythroid-derived 2)-like 2 pathway." *The Journal of pharmacology and experimental therapeutics* 2012, 341, 274-284.
Sykiotis et al., "Keap1/Nrf2 signaling regulates oxidative stress tolerance and lifespan in *Drosophila*." *Developmental cell* 2008, 14, 76-85.
Uruno et al., "The Keap1-Nrf2 system prevents onset of diabetes mellitus." *Molecular and cellular biology* 2013, 33, 2996-3010.

\* cited by examiner

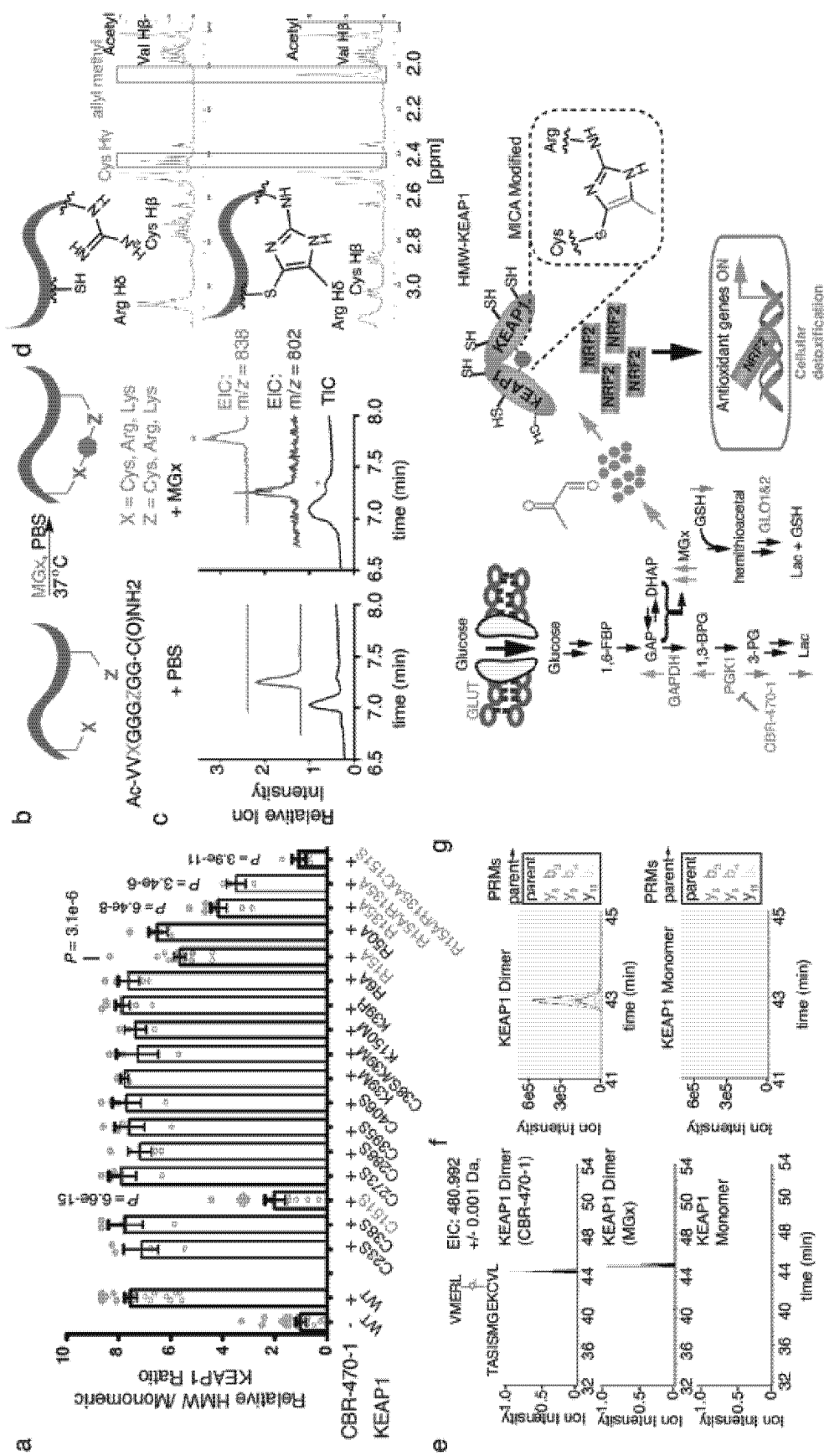
FIG. 3A-G

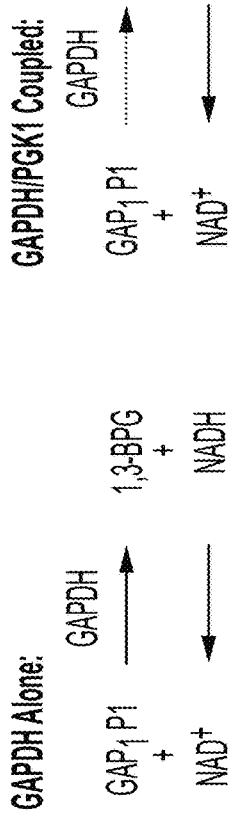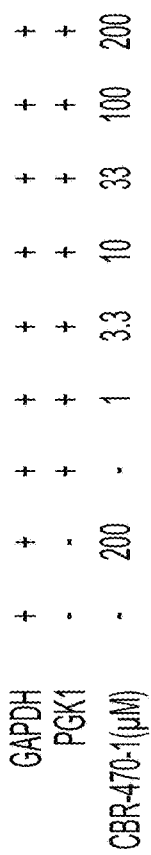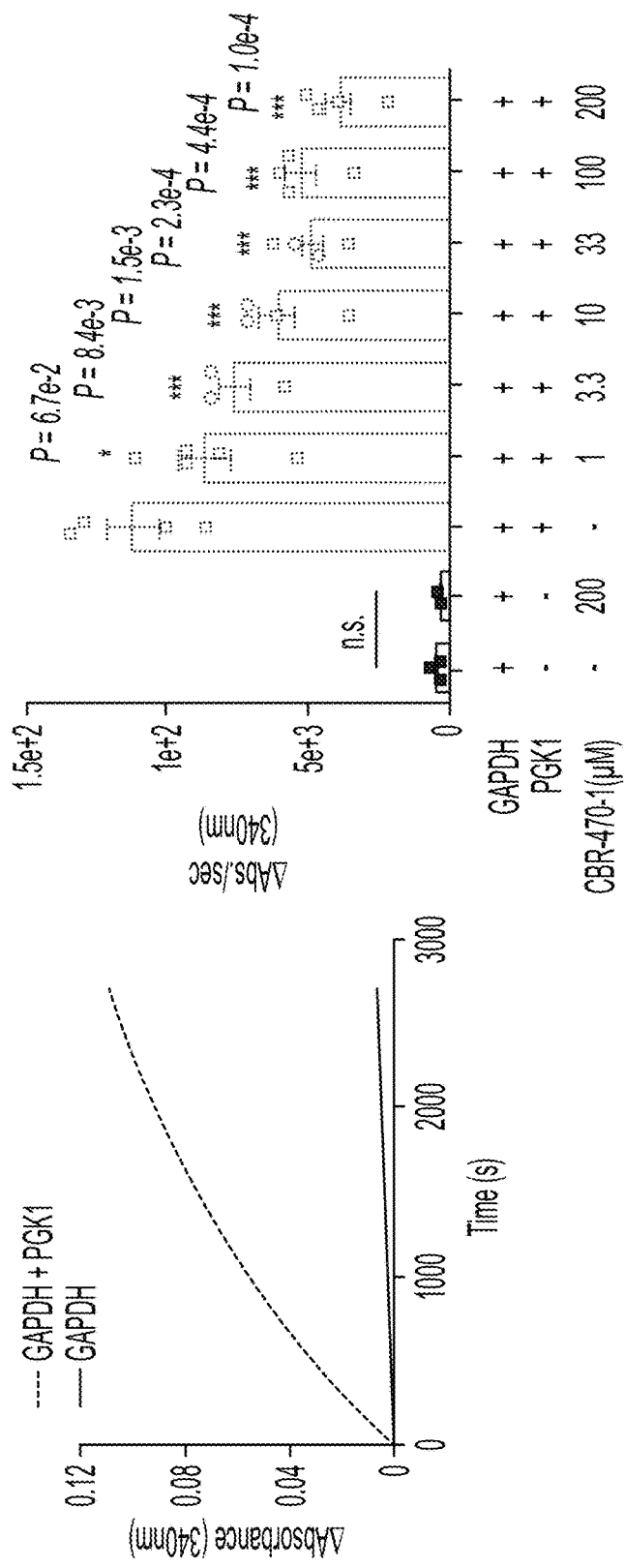
FIG. 6A
FIG. 6B

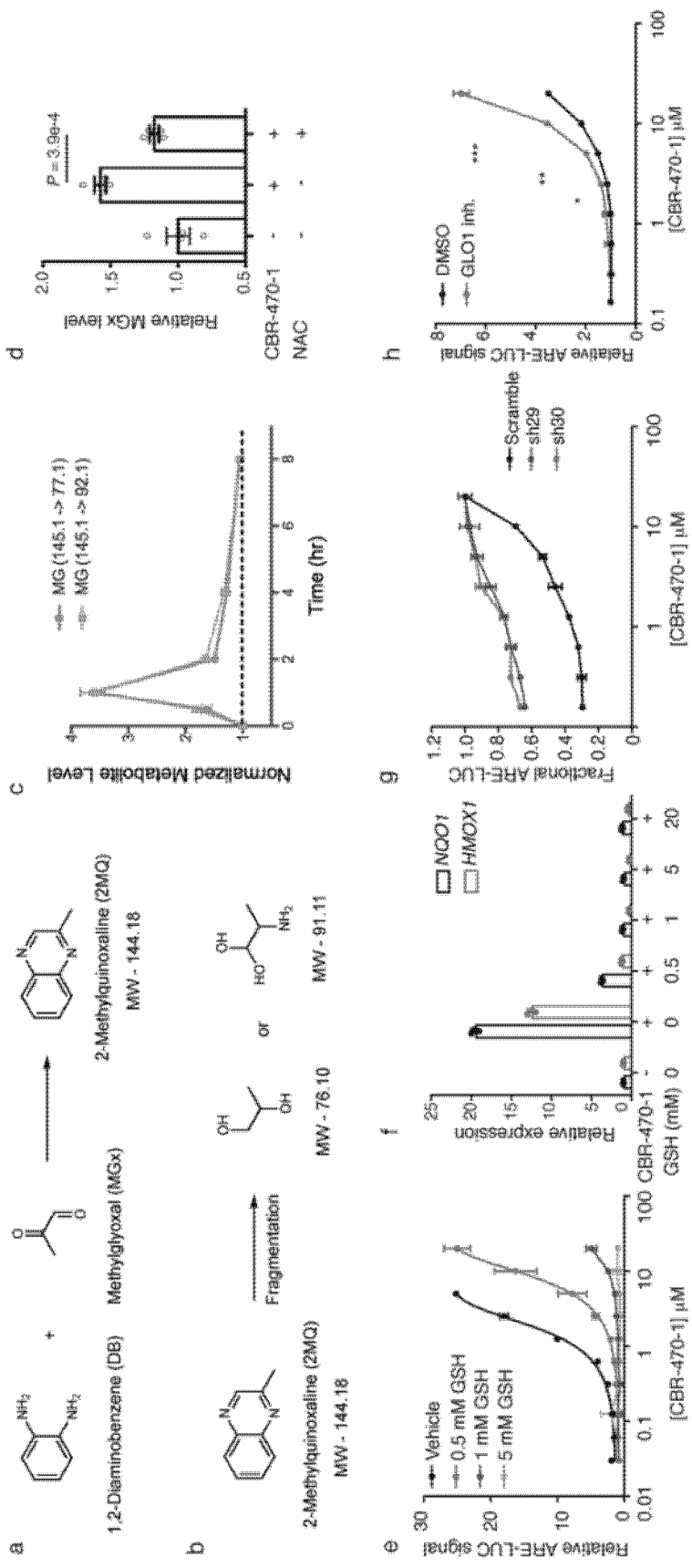
FIG. 8A-H

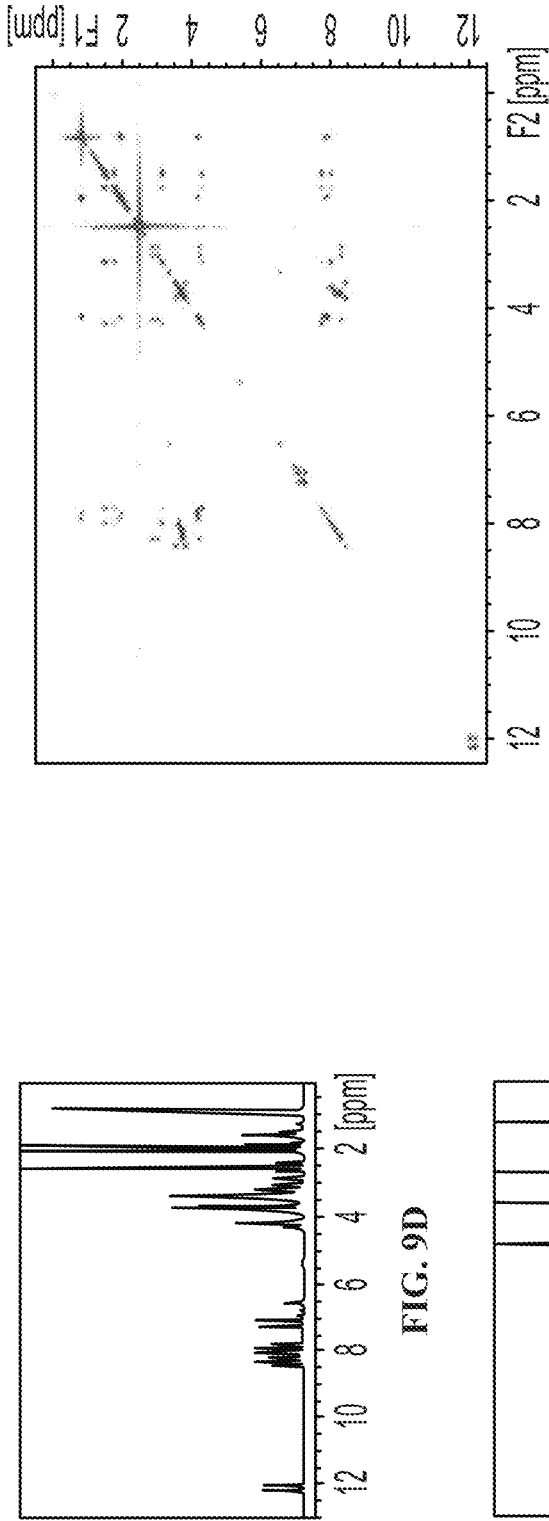
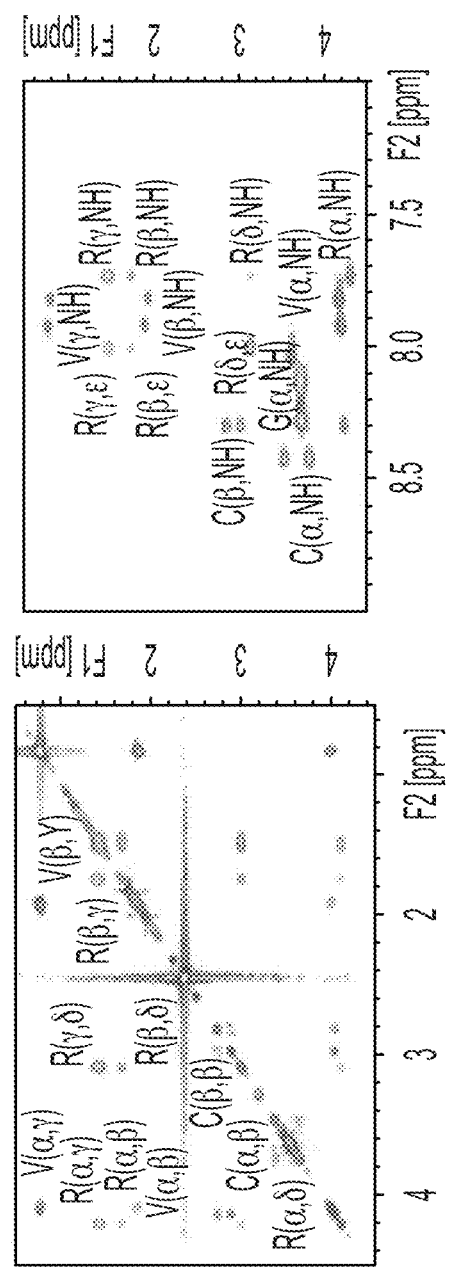
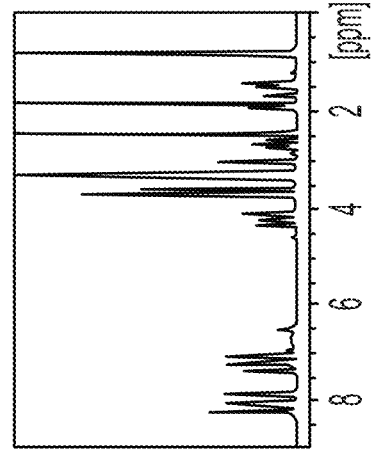
FIG. 9D
FIG. 9E
FIG. 9F

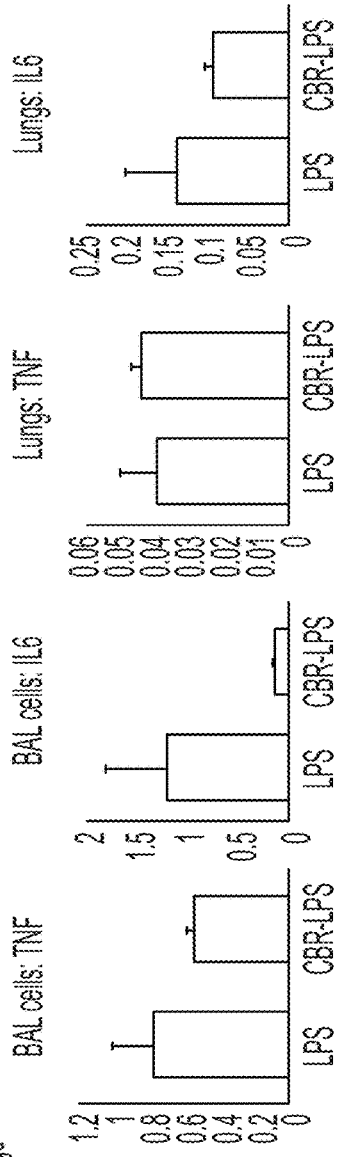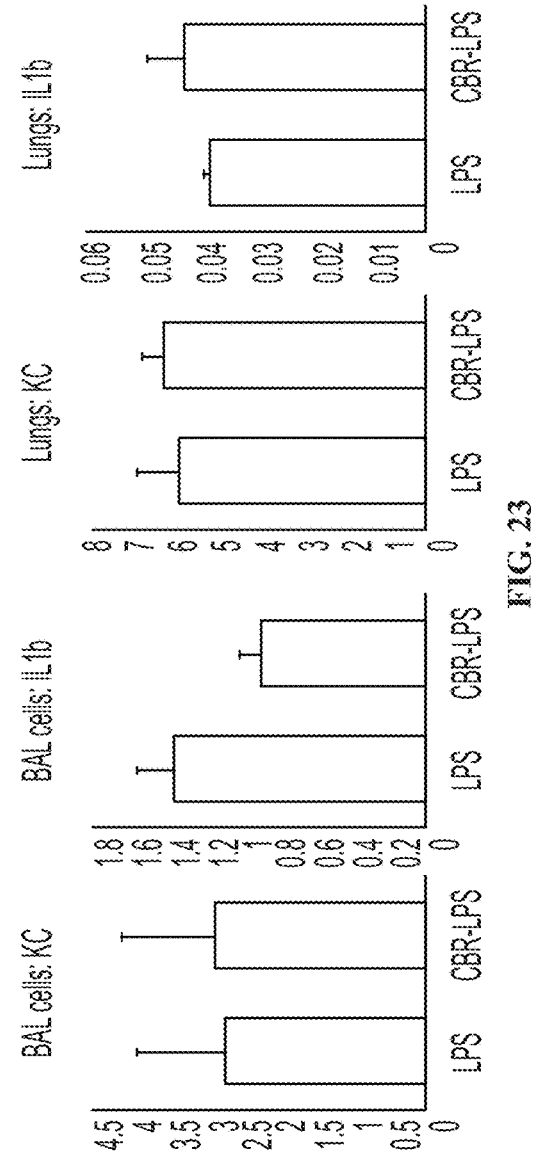
FIG. 23

| Cell line | CBR-470 IC50 [uM] | CBR-470 % viability reduction (20uM) | + 3 mM Pyruvate IC50 [uM] | + 3 mM Pyruvate % viability reduction (20uM) | + 1 mM Metformin IC50 [uM] | + 1 mM Metformin % viability reduction (20uM) | + 3 mM N-Acetylcysteine IC50 [uM] | + 3 mM N-Acetylcysteine % viability reduction (20uM) |
|---|---|---|---|---|---|---|---|---|
| A549 | >20 | 33.0 | >20 | 45.1 | >20 | 31.1 | >20 | 3.4 |
| U87 | >20 | 40.1 | >20 | 36.6 | >20 | 37.5 | >20 | increase 11.5 |
| U87 EGFRvIII | 16.4 | 59.3 | >20 | 38.7 | >20 | 38.5 | ~20 | 49.2 |
| H1299 | 13.7 | 61.9 | 11.2 | 69.2 | 12.2 | 64.3 | >20 | increase 9.2 |
| HeLa | 13.4 | 80.1 | 10.4 | 83.3 | 12.1 | 81.4 | >20 | 5.3 |
| SKOV3 | 11.4 | 70.7 | 10.2 | 70.3 | 9.4 | 73.1 | >20 | Increase 4.1 |
| OVCAR3 | 10.9 | 58.8 | 7.2 | 71.2 | >20 | 41.2 | >20 | 0.1 |
| MCF7 | 10.8 | 90.9 | 16.5 | 57.1 | 11.8 | 87.0 | >20 | 3.8 |
| PC3 | 9.6 | 75.5 | 13.5 | 71.3 | >20 | 48.1 | >20 | 17.5 |
| LNCaP | 8.4 | 73.0 | 18.1 | 58.5 | 10.5 | 70.5 | >20 | Increase 11.0 |
| HEK | 8.0 | 86.5 | 9.1 | 83.0 | 9.1 | 87.1 | >20 | 3.8 |
| IMR32 | 2.4 | 98.5 | 2.9 | 97.4 | 2.8 | 98.5 | >20 | 10.2 |

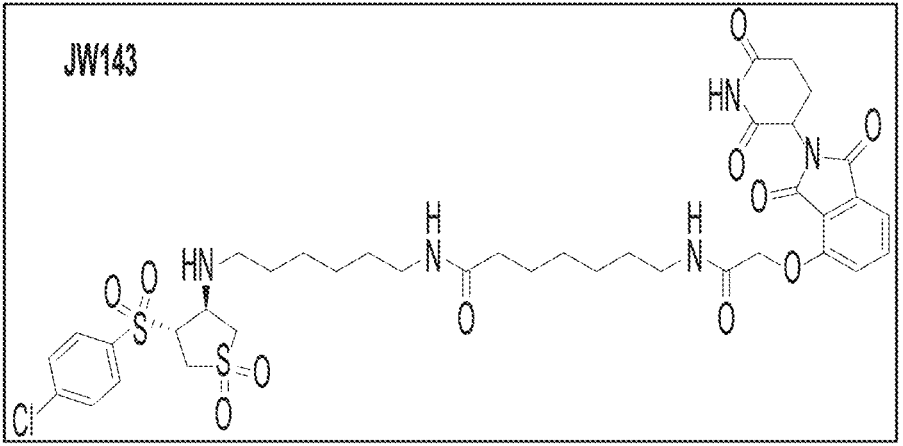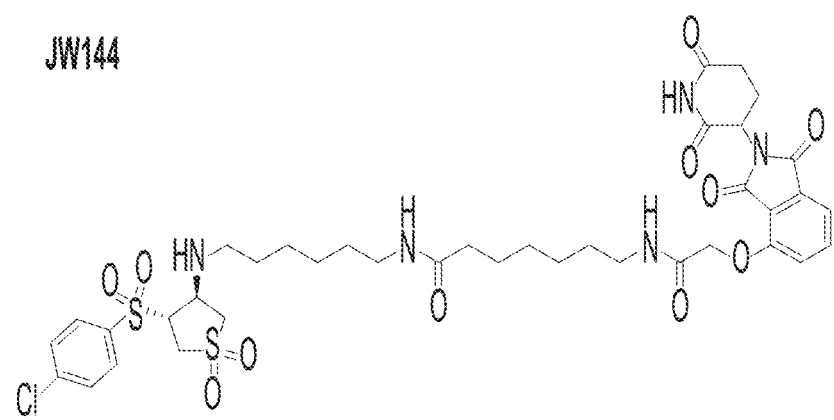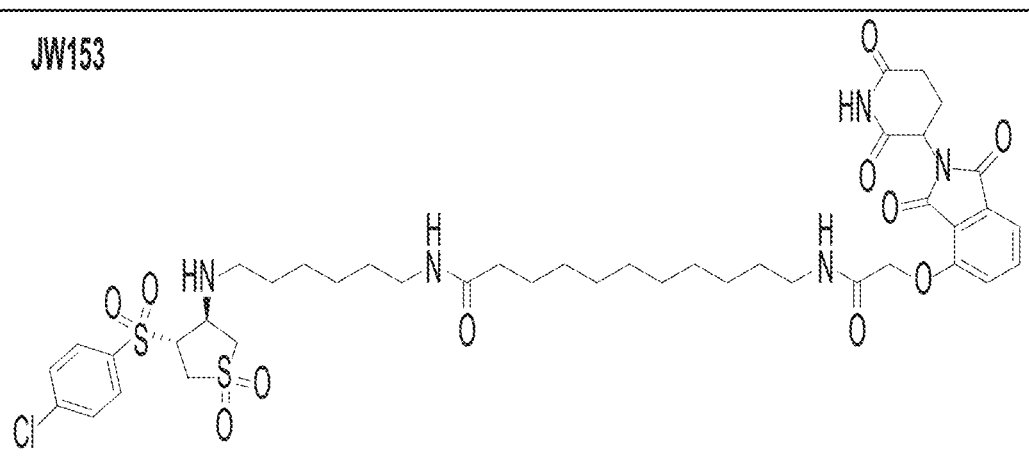
FIG. 29A (Continued)

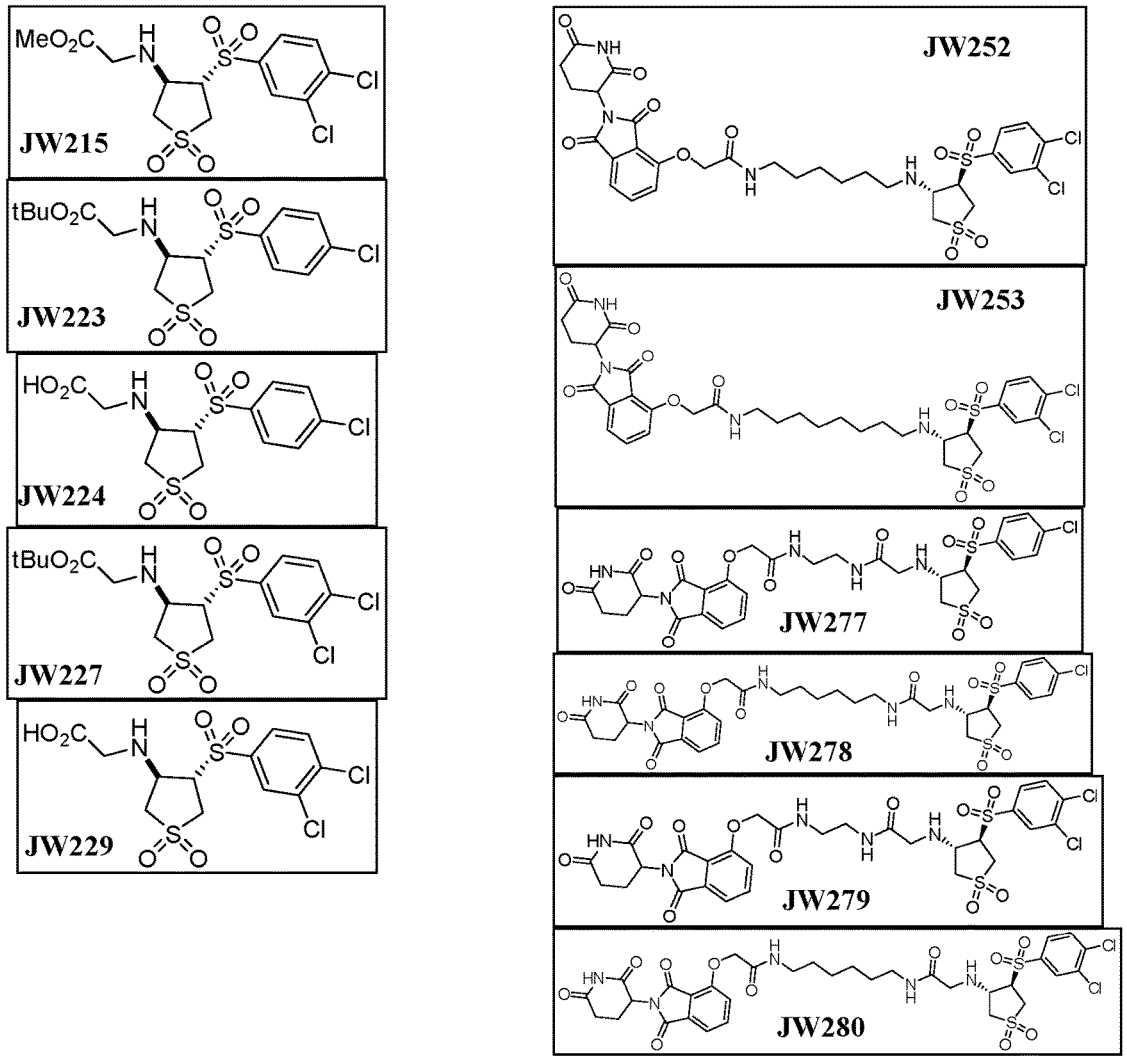
FIG. 29B
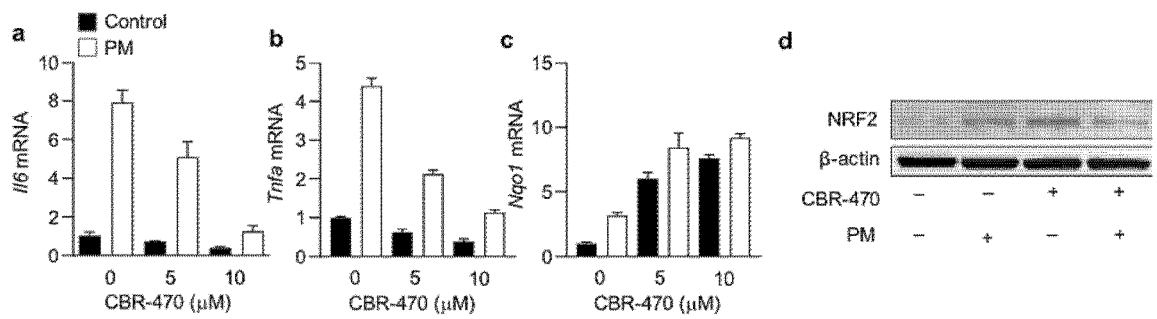
FIG. 30A-D

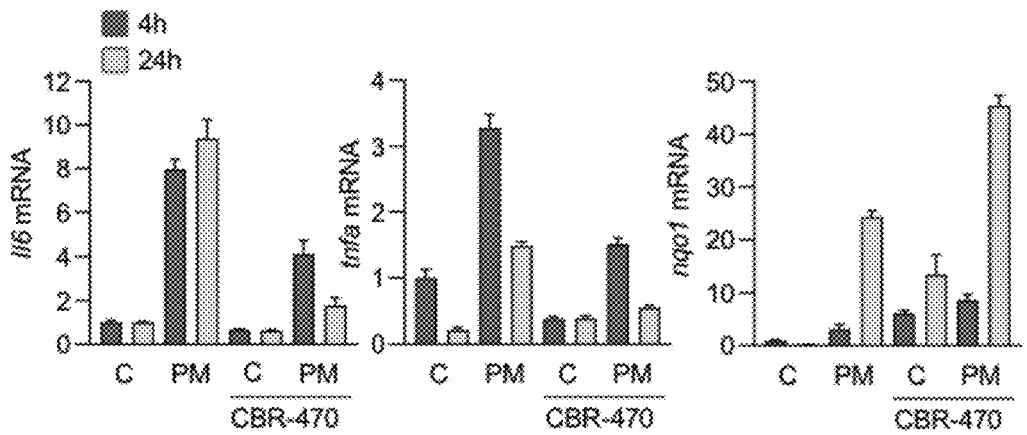
FIG. 31
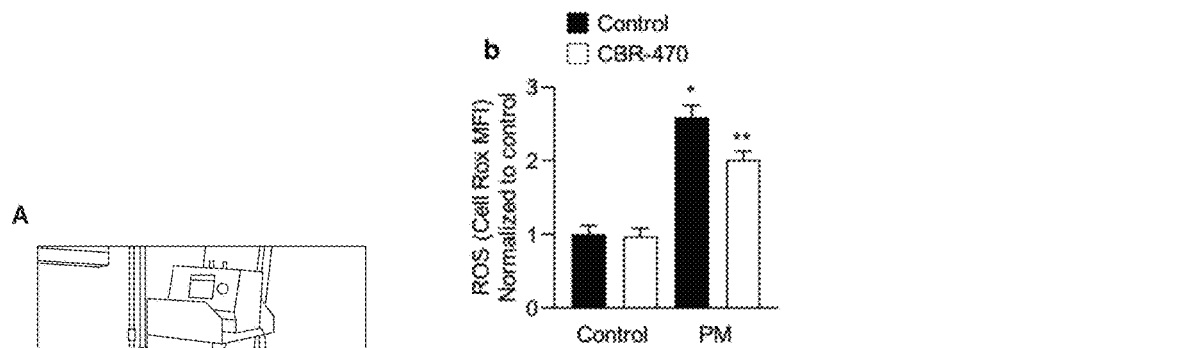
FIG. 32
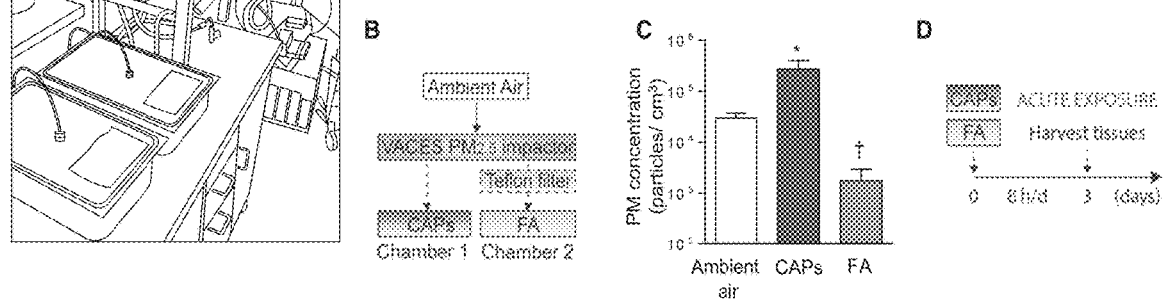
FIG. 33A-D

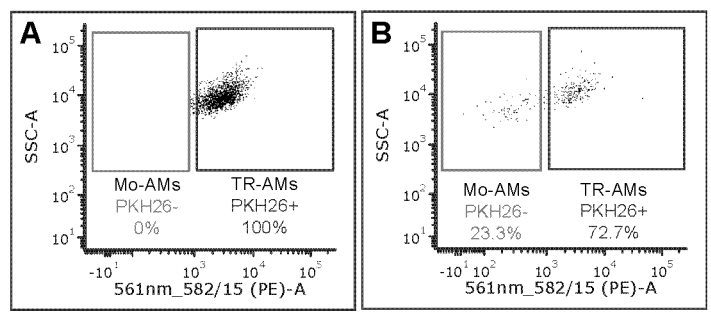
FIG. 34A-B
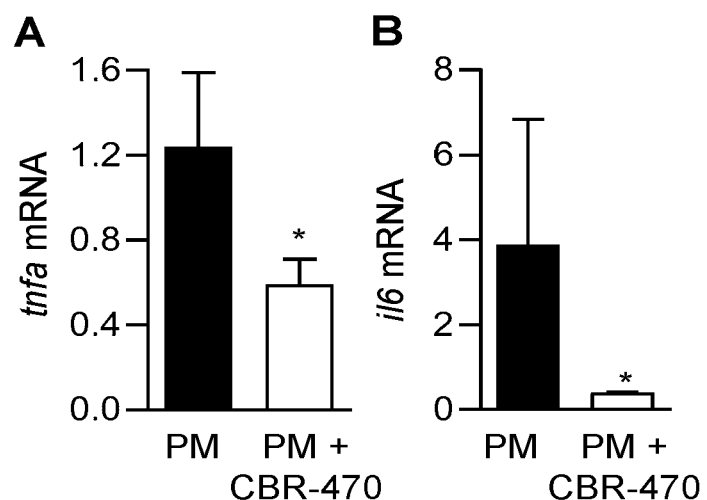
FIG. 35A-B

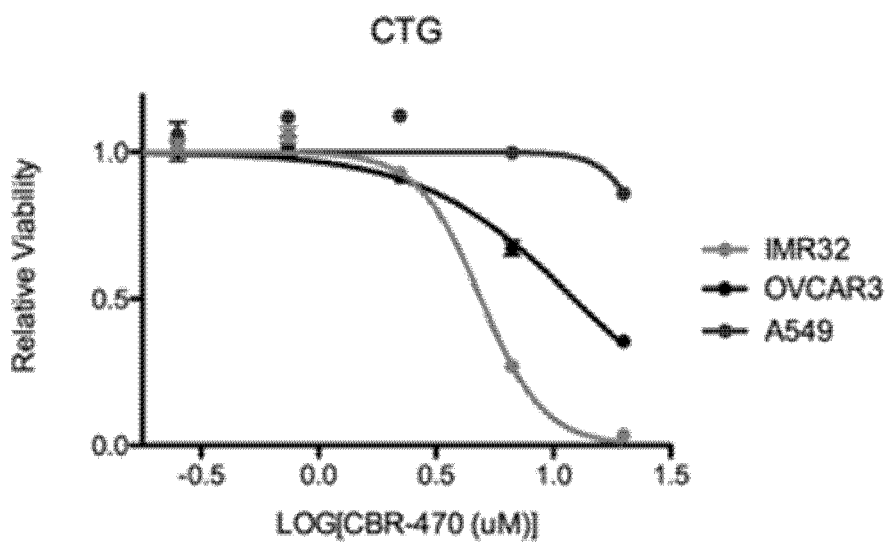
FIG. 36A-B

A.
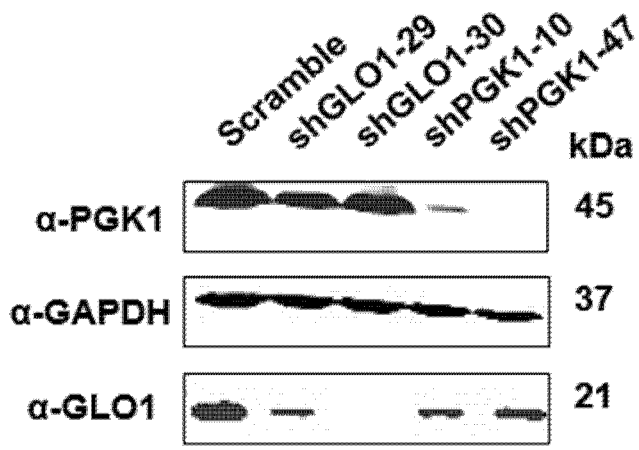
B.
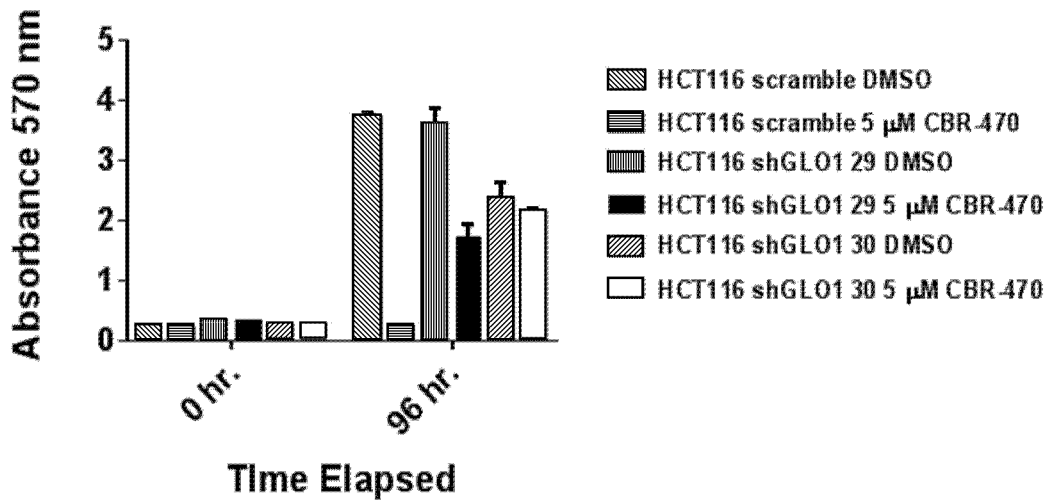
C.
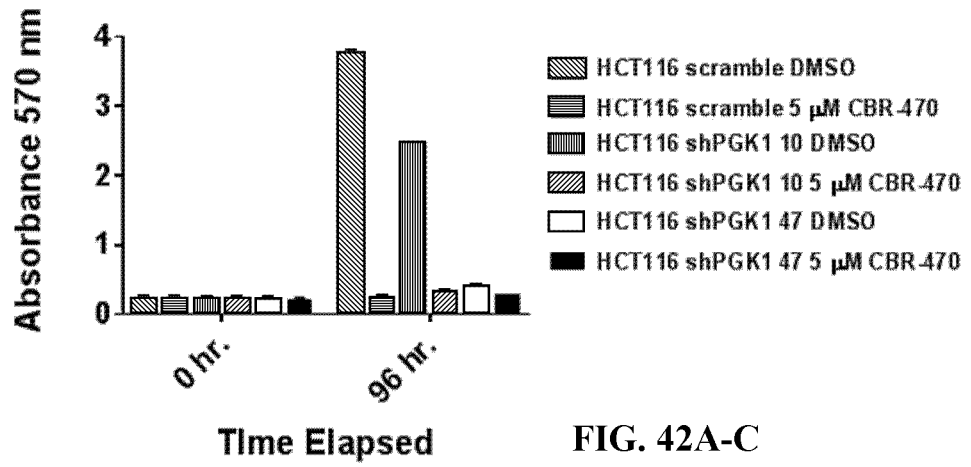
FIG. 42A-C

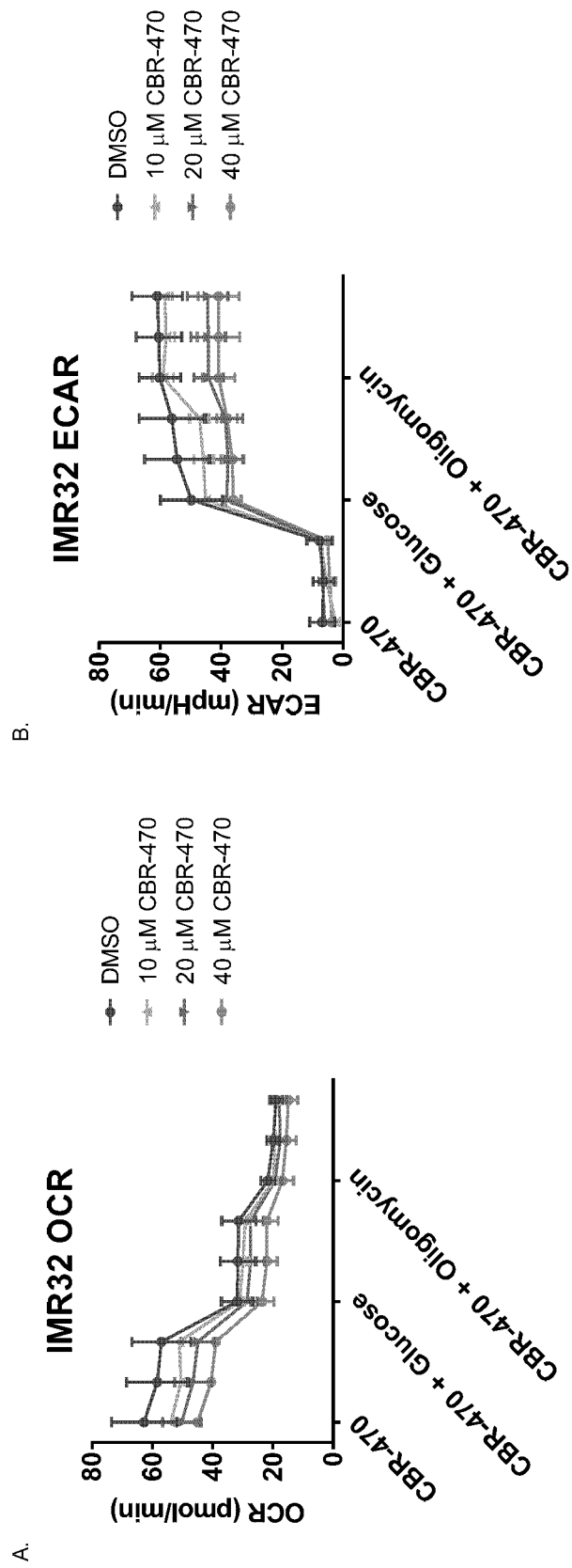
FIG. 43A-B

COMPOSITIONS AND METHODS FOR ACTIVATING NRF2-DEPENDENT GENE EXPRESSION

CROSS-REFERENCE TO RELATED APPLICATIONS

This application is a national phase application under 35 U.S.C. § 371 of International Application No. PCT/US2019/056105 filed Oct. 14, 2019, which claims the benefit of priority of U.S. Provisional Patent Application No. 62/745,454 filed Oct. 14, 2018, all of which are hereby incorporated by reference in their entirety.

STATEMENT REGARDING FEDERALLY FUNDED RESEARCH

This invention was made with government support under CA175399 and GM128199 awarded by the National Institutes of Health. The government has certain rights in the invention.

BACKGROUND

Mechanisms that integrate the metabolic state of a cell to regulatory pathways are necessary to maintain cellular homeostasis. Endogenous, intrinsically reactive metabolites are capable of forming functional, covalent modifications on proteins without the aid of enzymes[1,2], and regulate cellular functions including metabolism[3-5] and transcription[6]. A 'sensor' protein that captures specific metabolic information and transforms it into an appropriate response is Kelch-like ECH-associated protein 1 (KEAP1), which contains reactive cysteines that collectively act as an electrophile sensor tuned to respond to reactive species resulting from endogenous and xenobiotic molecules. Covalent modification of KEAP1 results in reduced ubiquitination and the accumulation of the NRF2[7,8], which then initiates transcription of cytoprotective genes at antioxidant-response element (ARE) loci. There are numerous diseases/conditions, including cancer[9], neurodegenerative disorders[10], chronic inflammatory diseases[11], diabetes[12] and aging[13] that are linked with deregulated KEAP1-NRF2 signaling.

There remains a need for additional compositions for modulating Nrf2 dependent gene expression, as well as methods of using such compositions to benefit subjects in need of upregulation.

SUMMARY

Certain embodiments are directed to compositions and methods for reducing ubiquitination of NRF2 resulting in accumulation of NRF2. The methods include exposing a target cell to conditions or compounds that directly or indirectly covalently modify Kelch-like ECH-associated protein 1 (KEAP1). In certain aspects, NRF2 accumulation initiates transcription of cytoprotective genes at antioxidant-response element (ARE) loci. The antioxidant response can be beneficial in treating or ameliorating numerous conditions and/or pathologies.

In providing additional compounds and/or methods for the positive modulation of NRF2 transcription pathway a number of phosphoglycerate kinase 1 (PGK1) inhibitors were tested for their ability to increase NRF2 transcription. In certain aspects PGK1 inhibitors increase the level of multimeric KEAP1, e.g., dimeric KEAP1, resulting in the reduced ubiquitinization of NRF2, increased NRF2 protein levels, and an increase in NRF2 target transcripts, proteins, and antioxidant response environmental factors in the cell.

Certain embodiments are directed to phosphoglycerate kinase 1 inhibitors having a general formula of:

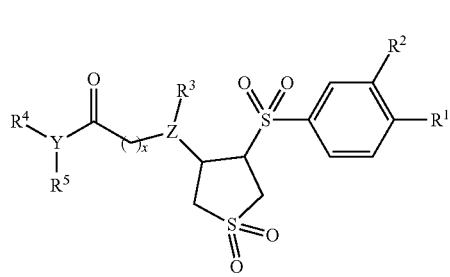

Formula I where $R^1$, $R^2$, $R^3$, $R^4$, and $R^5$ are independently selected from hydrogen, halo, nitro, mercapto, cyano, azido, silyl, hydroxy, amino, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and/or heteroaryl; x can be 0, 1, 2, 3, 4, 5, 6, 7, 8, 9, 10, 11, 12, 13, 14, 15, 16, 17, 18, 19, 20; and Y is N or O. In certain aspects, Z can be N, S, or O In certain instances at least one of $R^1$ or $R^2$ is a halogen; $R^3$ and $R^5$ is hydrogen, $R^4$ is hydrogen or C1 to C4 alkyl, and Y is O, wherein $R^1$ and $R^2$ are not chlorine when $R^4$ is hydrogen. In certain aspects $R_3$ can be a methyl; ethyl; linear, branched, or cyclic propyl or linear, branched, or cyclic butyl. In certain instances a propyl group is an isopropyl or cyclopropyl. In other instances the butyl group is a n-butyl, sec-butyl, isobutyl, or a tert-butyl. In certain aspects, $R^1$ is chlorine (Cl). In another aspect, $R^2$ is chlorine. In still another aspect $R^1$ and $R^2$ are chlorine. In certain instances compounds where $R^1$ and $R^2$ is chlorine, x is 1, Y is O and $R^4$ and $R^5$ are hydrogen can be specifically excluded. In certain aspects the compound can be CBR-470-1 or CBR-470-2.

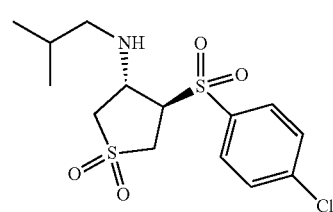

CBR-470-1

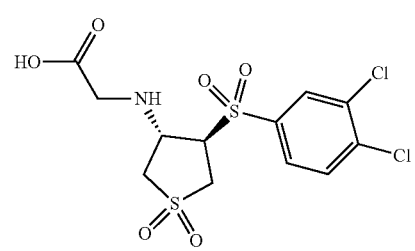

CBR-470-2

In certain embodiments a phosphoglycerate kinase 1 inhibitor/ubiquitin recruiter can have a general formula of:

Formula II

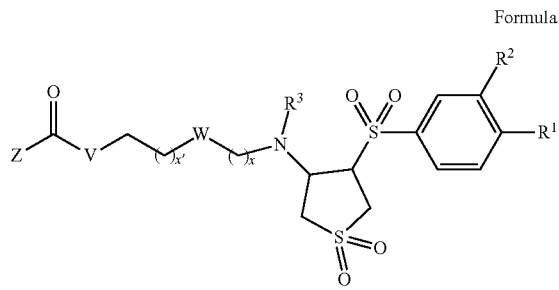

where $R^1$, $R^2$ and $R^3$ are independently selected from hydrogen, halo, nitro, mercapto, cyano, azido, silyl, hydroxy, amino, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and/or heteroaryl; x and/or x' is independently 0, 1, 2, 3, 4, 5, 6, 7, 8, 9, 10, 11, 12, 13, 14, 15, 16, 17, 18, 19, 20; W is direct bond, amide, or diol; V is N or O; and Z is an recruiter molecule. In certain aspects, the recruiter molecule is a ubiquitinase recruiter. A ubiquitinase recruiter can include, but is not limited to a moiety having the structure of Formula III.

Formula III

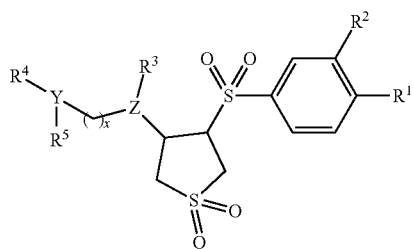

In a particular aspect, a compound of Formula II has $R^1$ is chlorine (Cl). In another aspect, $R^2$ is chlorine. In still another aspect $R^1$ and $R^2$ are chlorine. In certain aspects, $R^1$ is Cl, $R^2$ is H, x is 6, x' is 0, and W is a bond, V is N, and Z is a ubiquitinase recruiting moiety (JW121).

Certain embodiments are directed to phosphoglycerate kinase 1 inhibitors having a general formula of:

Formula IV

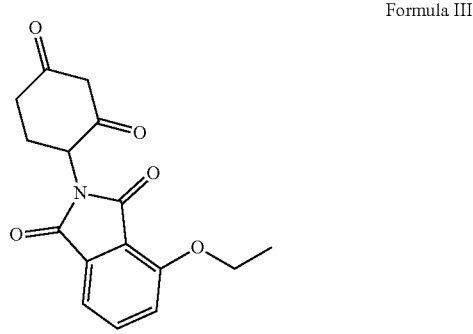

where $R^1$, $R^2$, $R^3$, $R^4$, and $R^5$ are independently selected from hydrogen, halo, nitro, mercapto, cyano, azido, silyl, hydroxy, amino, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and/or heteroaryl; x can be 0, 1, 2, 3, 4, 5, 6, 7, 8, 9, 10, 11, 12, 13, 14, 15, 16, 17, 18, 19, 20; and Y is direct bond, N or O. In certain instances at least one of $R^1$ or $R^2$ is a halogen; $R^3$ and $R^5$ is hydrogen, $R^4$ is hydrogen or C1 to C4 alkyl, and Y is O, wherein $R^1$ and $R^2$ are not chlorine when $R^4$ is hydrogen. In certain aspects $R_3$ can be a methyl; ethyl; linear, branched, or cyclic propyl or linear, branched, or cyclic butyl. In certain instances a propyl group is an isopropyl or cyclopropyl. In other instances the butyl group is a n-butyl, sec-butyl, isobutyl, or a tert-butyl. In certain aspects, $R^1$ is chlorine (Cl). In another aspect, $R^2$ is chlorine. In still another aspect $R^1$ and $R^2$ are chlorine. In certain instances compounds where $R^1$ is chlorine, $R^2R^4$ and $R^5$ are hydrogen, x is 0, Y is a direct bond, and $R^3$ is iso-butyl can be specifically excluded. In certain aspects, Formula IV can specifically exclude a compound where Y is a direct bond; $R^2$, $R^3$, and $R^4$ is hydrogen; $R^5$ is a C6 cycloalkyl; and $R^1$ if fluorine.

In certain embodiments a phosphoglycerate kinase 1 inhibitor/ubiquitin recruiter can have a general formula of:

Formula V

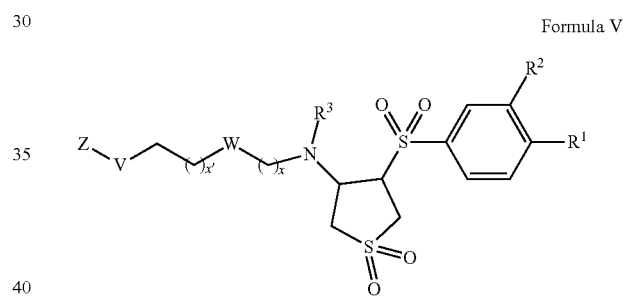

where $R^1$, $R^2$ and $R^3$ are independently selected from hydrogen, halo, nitro, mercapto, cyano, azido, silyl, hydroxy, amino, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and/or heteroaryl; x and/or x' is independently 0, 1, 2, 3, 4, 5, 6, 7, 8, 9, 10, 11, 12, 13, 14, 15, 16, 17, 18, 19, 20; W is a direct bond, amide, or diol; V is direct bond, N or O; and Z is an recruiter molecule. In certain aspects, the recruiter molecule is a ubiquitinase recruiter. A ubiquitinase recruiter can include, but is not limited to a moiety having the structure of Formula III.

Certain embodiments are directed to methods for activating NRF2 dependent transcription by inhibiting phosphoglycerate kinase 1 (PGK1) with a compound having a general formula of Formula I or Formula II or Formula IV or Formula V.

In certain embodiments NRF2 dependent transcription is activated to treat pulmonary fibrosis, acute lung injury, cancer, neurodegenerative disorders, chronic inflammatory diseases, diabetes, autoimmune disease, or aging.

Certain embodiments are directed to methods of treating pulmonary fibrosis comprising administering an activator of NRF2 dependent gene expression to a subject having pulmonary fibrosis, wherein the activator of NRF2 dependent gene expression is a compound of Formula I or Formula II or Formula IV or Formula V.

Other embodiments are directed to methods of treating acute lung injury comprising administering an activator of NRF2 dependent gene expression to a subject having acute lung injury, wherein the activator of NRF2 dependent gene expression is a compound of Formula I or Formula II or Formula IV or Formula V.

Certain embodiments are directed to methods of enhancing an immune response comprising administering an activator of NRF2 dependent gene expression to a subject, wherein the activator of NRF2 dependent gene expression is a compound of Formula I or Formula II or Formula IV or Formula V.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

As used herein, the term "IC50" refers to an inhibitory dose that results in 50% of the maximum response obtained.

The term half maximal effective concentration (EC50) refers to the concentration of a drug that presents a response halfway between the baseline and maximum after some specified exposure time.

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Use of the one or more compositions may be employed based on methods described herein. Use of one or more compositions may be employed in the preparation of medicaments for treatments according to the methods described herein. Other embodiments are discussed throughout this application. The embodiments in the Example section are understood to be embodiments that are applicable to all aspects of the technology described herein.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 3A-G. Methylglyoxal forms a novel posttranslational modification between proximal cysteine and arginine residues in KEAP1. (a) Quantified HMW-KEAP1 formation of wild-type or mutant FLAG-KEAP1 from HEK293 T cells treated with DMSO or CBR-470-1 for 8 hr (n=23 for WT; n=16 for R15A; n=13 for C151S; n=7 for K39R, R135A; n=4 for R6A, R50A, all other C-to-S mutations, and R15/135A & C151S triple-mutant; n=3 for R15/135A, and all K-to-M mutations). (b) Schematic of the model peptide screen for intramolecular modifications formed by MGx and nucleophilic residues. (c) Total ion-(TIC) and extracted ion chromatograms (EIC) from MGx- and mock-treated peptide, with a new peak in the former condition marked with an asterisk. EICs are specific to the indicated m/z. (n=3 independent biological replicates). (d) $^1$H-NMR spectra of the unmodified (top) and MICA-modified (bottom) model peptide, with pertinent protons highlighted in each. Notable changes in the MICA-modified spectrum include the appearance of a singlet at 2.04 p.p.m. (allyl methyl in MICA), loss of the thiol proton at 2.43 p.p.m., and changes in chemical shift and splitting pattern of the cysteine beta protons and the arginine delta and epsilon protons. (e) EIC from LC-MS/MS analyses of gel-isolated and digested HMW-KEAP1 (CBR-470-1 and MGx-induced) and monomeric KEAP1 for the C151-R135 crosslinked peptide. Slight retention time variation was observed on commercial columns (n=3 independent biological replicates). (f) PRM chromatograms for the parent and six parent-to-daughter transitions in representative targeted proteomic runs from HMW-KEAP1 and monomeric digests (n=6). (g) Schematic depicting the direct communication between glucose metabolism and KEAP1-NRF2 signaling mediated by MGx modification of KEAP1 and subsequent activation of the NRF2 transcriptional program. Univariate two-sided t-test (a); data are mean±SEM of biologically independent samples.

FIG. 6A-D. CBR-470-1 inhibits PGK1 in vitro and in situ. (a) Schematic of the GAPDH/PGK1 coupled assay. Pre-equilibration of the GAPDH reaction (top left) results in an NAD$^+$/NADH equilibrium, which upon addition of PGK1 and ADP pulls the reaction to the right producing more NADH. Monitoring NADH absorbance after addition of PGK1 (bottom right) can be used to monitor PGK1 activity in the forward direction (right). Kinetic monitoring of NADH absorbance (340 nm) after established equilibrium with GAPDH shows little change (black curve), but is significantly increased upon addition of PGK1, pulling the equilibrium to the right (red curve). (b) CBR-470-1 does not affect the GAPDH equilibrium alone, but significantly inhibits PGK1-dependent activity and accumulation of NADH (n=5). (c, d) Relative level of central metabolites in IMR32 cells treated with viral knockdown of PGK1 for 72 hours (c) (n=4) and with CBR-470-1 relative DMSO alone for the indicative times (d) (n=3). Each metabolite is normalized to the control condition at each time point. Data shown represent mean±SEM of biologically independent samples.

FIG. 8A-H. MGx and glyoxylase activity regulates NRF2 activation. CBR-470-1 causes elevated MGx levels in cells. (a) Schematic depicting chemical derivatization and trapping of cellular MGx for analysis by targeted metabolomics using two unique fragment ions. (b, c) Daughter ion fragments (b) and resulting MS/MS quantification of MGx levels (c) in IMR32 cells treated with CBR-470-1, relative to DMSO (n=4). (d) Quantitative LC-MS/MS measurement of cellular MGx levels in IMR32 cells treated for 2 hours with CBR-470-1 or co-treated for 2 hours with CBR-470-1 and NAC (2 mM) relative to DMSO (n=4).

FIG. 9A-F. Schematic of SILAC-based proteomic mapping of KEAP1 modifications in response to CBR-470-1 and NMR characterization of CR-MGx peptide. (a) Stable isotope-labeled cells (stable isotope labeling with amino acids in cell culture, SILAC) expressing FLAG-tagged KEAP1 were treated with vehicle ('light') and CBR-470-1 or MGx ('heavy'), respectively. Subsequent mixing of the cell lysates, anti-FLAG enrichment, tryptic digestion and LC-MS/MS analysis permitted detection of unmodified portions of KEAP1, which retained ~1:1 SILAC ratios relative to the median ratios for all detected KEAP1 peptides. In contrast, peptides that are modified under one condition will no longer match tryptic MS/MS searches, resulting skewed SILAC ratios that "drop out" (bottom). (b) Structural depiction of potentially modified stretches of human KEAP1 (red) using published x-ray crystal structure of the BTB (PDB: 4CXI) and KELCH (PDB: 1U6D) domains. Intervening protein stretches are depicted as unstructured loops in green. (c) SILAC ratios for individual tryptic peptides from FLAG-KEAP1 enriched MGx treated heavy' cell lysates and no treated 'light' cell lysates, relative to the median ratio of all KEAP1 peptides. Highlighted tryptic peptides were significantly reduced by 2- to 2.5-fold upon relative to the KEAP1 median, indicative of structural modification (n=12). (d) $^1$H-NMR of CR-MGx peptide (isolated product of MGx incubated with Ac-NH-VVCGGGRGG-C(O)NH$_2$ peptide) (SEQ ID NO:70). $^1$H NMR (500 MHz, d6-DMSO) δ 12.17 (s, 1H), 12.02 (s, 1H), 8.44 (t, J=5.6 Hz, 1H), 8.32-8.29 (m, 2H), 8.23 (t, J=5.6 Hz, 1H), 8.14 (t, J=5.9 Hz, 1H), 8.05 (t, J=5.9 Hz, 1H), 8.01 (t, J=5.9 Hz, 1H), 7.93 (d, J=8.5 Hz, 1H), 7.74 (d, J=8.0 Hz, 1H), 7.26 (s, 1H), 7.09 (s, 1H), 4.33-4.28 (m, 1H), 4.25-4.16 (m, 3H), 3.83 (dd, J=6.9 Hz, J=16.2 Hz, 1H), 3.79-3.67 (m, 6H), 3.63 (d, J=5.7 Hz, 2H), 3.54 (dd, J=4.9 Hz, J=16.2 Hz, 1H), 3.18-3.13 (m, 2H), 3.04 (dd, J=4.9 Hz, J=13.9 Hz, 1H), 2.88 (dd, J=8.6 Hz, J=13.6 Hz, 1H), 2.04 (s, 3H), 1.96 (sep, J=6.8 Hz, 2H), 1.87 (s, 3H), 1.80-1.75 (m, 1H), 1.56-1.47 (m, 3H), 0.87-0.82 (m, 12H). (e) 1H-NMR of CR peptide (Ac-NH-VVCGGGRGG-C(O) NH$_2$). 1H NMR (500 MHz, d6-DMSO) δ 8.27-8.24 (m, 2H), 8.18 (t, J=5.7 Hz, 1H), 8.13-8.08 (m, 3H), 8.04 (t, J=5.7 Hz, 1H), 7.91 (d, J=8.8 Hz), 7.86 (d, J=8.8 Hz, 1H), 7.43 (t, J=5.4 Hz, 1H), 7.28 (s, 1H), 7.10 (s, 1H), 4.39 (dt, J=5.6 Hz, J=7.4 Hz, 1H), 4.28 (dt, J=5.7 Hz, J=7.2 Hz, 1H), 4.21-4.13 (m, 2H), 3.82-3.70 (m, 8H), 3.64 (d, J=5.8 Hz, 2H), 3.08 (dt, J=6.5 Hz, J=6.5 Hz, 2H), 2.80-2.67 (m, 2H), 2.43 (t, J=8.6 Hz, 1H), 1.94 (sep, J=6.8 Hz, 2H), 1.85 (s, 3H), 1.75-1.68 (m, 1H), 1.54-1.42 (m, 3H), 0.85-0.81 (m, 12H). (f) $^1$H-$^1$H TOCSY of CR-MGx peptide. (g) Peak assignment for CR-MGx peptide TOCSY spectrum. Data are mean±SEM of biologically independent samples.

FIG. 23. Mice treated with CBR-470-2 or vehicle (NaOH) IP and intratracheally instill LPS to induce acute lung injury. CBR-470-2 decreased IL-6, and mRNA expression in immune cells (BAL cells).

FIG. 29A-B. Non-limiting examples of chemical structures for NRF2 dependent gene expression activators.

FIG. 30A-D. CBR-470 activates NRF2 and inhibits PM-induced inflammatory cytokine production from alveolar macrophages. (a-c) Indicated transcript levels in response to PM exposure for 4 hr in the presence and absence of CBR-470, PGK1 inhibitor (10 micromolar). (d) Western blot analysis of NRF2 protein levels under the conditions in a-c.

FIG. 31. Time dependent effects of CBR-470-1 on alveolar macrophage cytokine mRNA levels at specific timepoints FIG. 32. CBR-470-1 does not cause significant ROS elevation in alveolar macrophages, and only a slight decrease in overall cellular bioenergetics in this cell and metabolic background. This represents a distinct mechanism of action compared to many other pharmacologic NRF2 activators, which achieve efficacy through induction of ROS (reactive oxygen species).

FIG. 33A-D. Inhalational exposure to concentrated ambient particles (CAPs). (A) The photograph and (B) schematic of the VACES PM2.5 impactor and chambers depicting how mice will be exposed to CAPs or filtered air (FA). The PM2.5 generated from ambient air are delivered to murine chambers housing up to 32 mice each (with food and water). Control mice are housed in an identical chamber, connected to the VACES with a Teflon filter placed in the chamber inlet. (C) Ambient and delivered particle concentrations are measured using a TSI 3775 particle counter Particle concentrations are about 10-fold higher or lower than ambient air levels in the CAPs and FA chambers, respectively. 13,21 $p<0.05$, *CAPs and †FA vs. ambient air. (D) Timeline for exposure to PM (8 h/d×3 days).

FIG. 34A-B. Identification of tissue resident (TR-AMs) and monocyte-derived (Mo-AMs) alveolar macrophages using PKH26 dye method. Mice are treated with PKH26 Red Fluorescent Cell Linker dye (Sigma) 1 day prior to intratracheal instillation of PM (10 □g/Ma-douse). The PKH26 labels the lipid membrane of tissue resident alveolar macrophages (TR-AMs), but not the bone marrow cells from which infiltrating monocyte-derived recruited macrophages (Mo-AMs) arise. Following PM exposure, cells were collected and stained with F4/80 antibody to select for macrophages. Then TR-AMs (PKH26+) and recruited Mo-AMs (PKH26−) were flow-sorted based on PKH26 fluorescence. Flow cytometry plots show that (A) TR-AMs are the only subpopulation of AMs on day 0 and (B) both Mo-AMs and TR-AMs following PM are observed.

FIG. 35A-B. Inhibition of PGK1 (CBR-470) attenuates PM-induced cytokine production from alveolar macrophages in mice. C57Bl/6 mice were exposed to either PM or filtered air 8 h/day for 3 days while receiving either CBR-470 or control vehicle. At the end of exposure, alveolar macrophages are isolated and measured mRNA expression of (A) TNFa and (B) IL-6. Expression data is shown relative to FA samples and control housekeeping gene.

FIG. 36A-B. Viability assays performed in each cell line with compound treatment with CBR-470-1. Concentrations ranging from 0.1 to 30 micromolar for 48 hr. Viability was measured using Cell titer glo ATP quantification assay. Representative curves for three cell lines at 48 are shown on the left in (A). Table of 20 cell line IC50 values are shown in (B).

FIG. 42A-C. Genetic manipulation of central glycolytic targets GLO1 and PGK1 regulate viability in the very sensitive colorectal cancer cell line HCT116. In line with genetic correlations, acclimation of cells to low GLO1 levels results in resistance to CBR-470-1 metabolic inhibition PGK1 knockdown cells grow more slowly and are more sensitive to CBR-470-1 metabolic inhibition FIG. 43A-B. IMR32, a more sensitive cell line to the anti-proliferative effects of CBR-470-1, exhibits reduced glycolytic flux and oxidative phosphorylation rate, as measured by global bioenergetics with a Seahorse XF96 global metabolic profile of Extracellular Acidification Rate (ECAR) and Oxygen Consumption Rate (OCR). Cells were plated for 24 hrs., then incubated with the indicated doses of CBR-470 for 1 hr. Under CBR-470-1 treated conditions, cellular ECAR and OCR was recorded for CBR-470 alone, CBR-470+10 mM Glucose, and CBR-470+3 μM Oligomycin.

DESCRIPTION

Figure 1A:
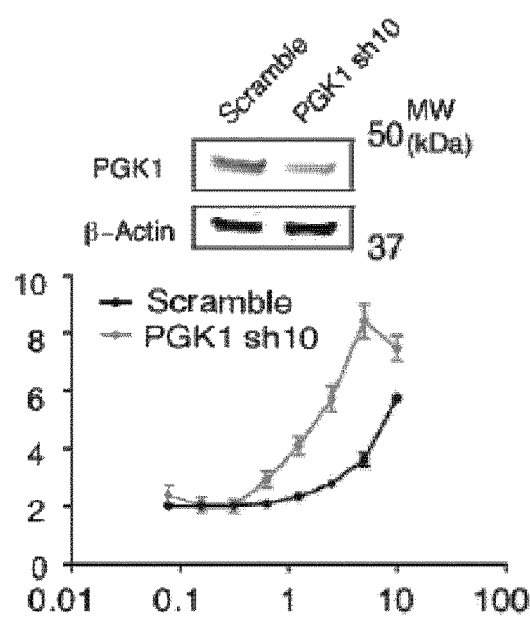
FIG. 1A-D. CBR-470-1-dependent inhibition of glycolysis activates NRF2 signaling. CBR-470-1 activation of ARE-LUC reporter in HEK293T cells with transient knockdown (a) or overexpression (b) of PGK1 demonstrates opposing effects on compound potency. PGK1, Actin and Tubulin protein levels are shown from representative experiments (n=3). (c) Heat map depiction of relative metabolite levels in IMR32 cells treated for 30 min with CBR-470-1 (left) or viral shRNA knockdown of PGK1 (right) relative to DMSO and scramble shRNA controls, respectively. BPG refers to both 2,3-BPG and 1,3-BPG, whereas 1,3-BPG specifically refers to the 1,3-isomer.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to intimate that the scope of the disclosure, including the claims, is limited to that embodiment.

Certain embodiments are directed to compositions and methods for initiating or activating or increasing transcription of cytoprotective genes at antioxidant-response element (ARE) loci. The increase in cytoprotective gene transcription can be positively modulated by reducing ubiquitination of NRF2 resulting in accumulation of NRF2. The methods include exposing a target cell to conditions or compounds that directly or indirectly covalently modify Kelch-like ECH-associated protein 1 (KEAP1) that results in an increase in NRF2 dependent transcription.

In certain aspects, the compositions include small molecule inhibitors of the glycolytic enzymes, such as PGK1. In certain aspects the glycolysis pathway can be manipulated so that methylglyoxal (MGx) levels are increased. Small molecule inhibitors of the glycolytic enzyme PGK1 revealed a link between glycolysis and NRF2 signaling. Inhibition of PGK1 results in accumulation of the reactive metabolite MGx, which selectively modifies KEAP1 to form a novel methylimidazole crosslink between proximal cysteine and arginine residues (MICA) posttranslational modification (PTM). This PTM results in KEAP1 dimerization, NRF2 accumulation and activation of the NRF2 transcriptional program. These results demonstrate the existence of direct inter-pathway communication between glycolysis and the KEAP1-NRF2 transcriptional axis, provides new insight into metabolic regulation of cell stress response, and suggests a novel therapeutic strategy for controlling the cytoprotective antioxidant response in numerous human diseases by modulation of the KEAP1-NRF2 axis by manipulation of the glycolysis pathway.

In certain embodiments the compositions, medicaments, and/or NRF2 dependent gene expression activators are prepared for oral, sublingual, buccal, topical, rectal, inhalation, transdermal, subcutaneous, intravenous, intra-arterial, intrathecal, intramuscular, intraosseous, intradermal, intraperitoneal, transmucosal, intra-articular, peri-articular, local, epidural, or epicutaneous administration.

In a further aspect the NRF2 dependent gene expression activator is administered separately, sequentially, or simultaneously (co-administered or co-formulated) in combination with one or more further pharmacologically active compounds or agents (i.e., secondary agents). In certain aspects, secondary agent can include agents useful for treating pulmonary fibrosis, acute lung injury, cancer, neurodegenerative disorders, chronic inflammatory diseases, diabetes, autoimmune disease or aging.

In further embodiments the secondary agent can be a therapeutic agent, such as an anti-cancer agent (e.g., a chemotherapeutic) or anti-diabetic agent.

Certain aspects are directed to providing a pharmaceutical composition for the prevention and/or treatment of pulmonary fibrosis, acute lung injury, cancer, neurodegenerative disorders, chronic inflammatory diseases, diabetes, autoimmune disease or aging and/or symptoms of pulmonary fibrosis, acute lung injury, cancer, neurodegenerative disorders, chronic inflammatory diseases, diabetes, autoimmune disease or aging or for ameliorating, controlling, reducing incidence of, or delaying the development or progression of pulmonary fibrosis, acute lung injury, cancer, neurodegenerative disorders, chronic inflammatory diseases, diabetes, autoimmune disease or aging and/or symptoms of pulmonary fibrosis, acute lung injury, cancer, neurodegenerative disorders, chronic inflammatory diseases, diabetes, autoimmune disease or aging in an individual, comprising an NRF2 dependent gene expression activator and a pharmaceutically acceptable carrier and/or an excipient.

In one embodiment, "prepared for" herein means the medicament is in the form of a dosage unit or the like suitably packaged and/or marked for use in treating pulmonary fibrosis, acute lung injury, cancer, neurodegenerative disorders, chronic inflammatory diseases, diabetes, autoimmune disease or aging.

"Reducing incidence" of pulmonary fibrosis, acute lung injury, cancer, neurodegenerative disorders, chronic inflammatory diseases, diabetes, autoimmune disease or aging and/or a symptom associated with pulmonary fibrosis, acute lung injury, cancer, neurodegenerative disorders, chronic inflammatory diseases, diabetes, autoimmune disease or aging means any of reducing severity (which can include reducing need for and/or amount of (e.g., exposure to) other drugs and/or therapies generally used for these conditions), duration, and/or frequency.

"Ameliorating" pulmonary fibrosis, acute lung injury, cancer, neurodegenerative disorders, chronic inflammatory diseases, diabetes, autoimmune disease or aging and/or a symptom associated with pulmonary fibrosis, acute lung injury, cancer, neurodegenerative disorders, chronic inflammatory diseases, diabetes, autoimmune disease or aging means a lessening or improvement of one or more symptoms of pulmonary fibrosis, acute lung injury, cancer, neurodegenerative disorders, chronic inflammatory diseases, diabetes, autoimmune disease or aging respectively and/or symptoms associated with pulmonary fibrosis, acute lung injury, cancer, neurodegenerative disorders, chronic inflammatory diseases, diabetes, autoimmune disease or aging respectively as compared to not administering an Nrf2 dependent gene expression activator. "Ameliorating" also includes shortening or reduction in duration of a symptom.

"Palliating" pulmonary fibrosis, acute lung injury, cancer, neurodegenerative disorders, chronic inflammatory diseases, diabetes, autoimmune disease or aging and/or a symptom associated with pulmonary fibrosis, acute lung injury, cancer, neurodegenerative disorders, chronic inflammatory diseases, diabetes, autoimmune disease or aging means lessening the extent of one or more undesirable clinical manifestations of pulmonary fibrosis, acute lung injury, cancer, neurodegenerative disorders, chronic inflammatory diseases, diabetes, autoimmune disease or aging respectively in an individual or population of individuals treated with an Nrf2 dependent gene expression activator in accordance with the invention.

As used therein, "delaying" the development of pulmonary fibrosis, acute lung injury, cancer, neurodegenerative disorders, chronic inflammatory diseases, diabetes, autoimmune disease or aging means to defer, hinder, slow, retard, stabilize, and/or postpone progression of pulmonary fibrosis, acute lung injury, cancer, neurodegenerative disorders, chronic inflammatory diseases, diabetes, autoimmune disease or aging respectively and/or a symptom associated with pulmonary fibrosis, acute lung injury, cancer, neurodegenerative disorders, chronic inflammatory diseases, diabetes, autoimmune disease or aging respectively. This delay can be of varying lengths of time, depending on the history of the disease and/or individuals being treated. As is evident to one skilled in the art, a sufficient or significant delay can, in effect, encompass prevention, in that the individual does not develop pulmonary fibrosis, acute lung injury, cancer, neurodegenerative disorders, chronic inflammatory diseases, diabetes, autoimmune disease or aging respectively. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

Certain aspects are directed to treating cancer or cancer metastasis in a subject by administering an NRF2 dependent gene expression activator.

In certain embodiments an NRF2 dependent gene expression activator can be administered for the treatment of cancer. In certain aspects the cancer is pancreatic cancer, pancreatic ductal adenocarcinoma, prostate cancer, skin cancer, melanoma, bladder cancer, blood cancer, bone cancer, brain cancer, breast cancer, colorectal cancer, esophageal cancer, gastrointestinal cancer, liver cancer, lung cancer, nasopharynx cancer, ovarian cancer, stomach cancer, testicular cancer, or uterine cancer. In certain aspects the NRF2 dependent gene expression activator is selected from the NRF2 dependent gene expression activator described herein.

Cancer can be one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukemia, primary or secondary bone cancer, tumors that metastasize to the bone, tumors infiltrating the nerve and hollow viscus, tumors near neural structures. Further preferably the cancer pain comprises visceral pain, such as visceral pain that arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

Some embodiments of the present invention concern methods of treating a patient. The patient may have any disease or condition for which treatment of NRF2 dependent gene expression activator is indicated. Examples of such diseases and conditions are discussed throughout this specification. "Treatment" and "treating" as used herein refer to administration or application of a therapeutic agent to a subject or performance of a procedure or modality on a subject for the purpose of obtaining a therapeutic benefit of a disease or health-related condition. For example, a pharmaceutical composition that includes one or more NRF2 dependent gene expression activator may be administered to a subject to inhibit pulmonary fibrosis, acute lung injury, cancer, neurodegenerative disorders, chronic inflammatory diseases, diabetes, autoimmune disease or aging.

The term "therapeutic benefit", "effective amount" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

I. Chemical Definitions

Various chemical definitions related to compounds described herein are provided as follows.

As used herein, the term "nitro" means —$NO_2$; the term "halo" or "halogen" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e., unbranched) or branched carbon chain of 1, 2, 3, 4, 5, 6, 7, 8, 9, or 10 carbons, which may be fully saturated, mono-unsaturated, or polyunsaturated. An unsaturated alkyl group includes those having one or more carbon-carbon double bonds (alkenyl) and those having one or more carbon-carbon triple bonds (alkynyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, iso-propyl), —$CH_2CH_2CH_2CH_3$ (n-Bu, n-butyl), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups. Specifically included within the definition of "alkyl" are those alkyl groups that are optionally substituted.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the heteroalkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, —$CH_2CH_2OC(O)CH_3$, —$CH_2CH_2NHCO_2C(CH_3)_3$, and —$CH_2Si(CH_3)_3$. Specifically included within the definition of "heteroalkyl" are those heteroalkyl groups that are optionally substituted.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, and the like. Specifically included within the definition of "cycloalkyl" are those cycloalkyl groups that are optionally substituted. Specifically included within the definition of "heterocyclyl" are those heterocycle groups that are optionally substituted.

The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. In certain aspects an aryl group is a phenyl group. Specifically included within the definition of "aryl" are those aromatic groups that are optionally substituted. For example, in some embodiments of the present invention, the "aryl" groups are optionally substituted with from 1 to 5 substituents selected from the group consisting of hydrogen, hydroxy, aryl, acyl, C1-C6 alkyl, C1-C6 alkoxy, C2-C6 alkenyl, C2-C6 alkynyl, substituted alkyl, substituted alkoxy, substituted alkenyl, substituted alkynyl, amino, amino substituted by one or two C1-C6 alkyl groups, cyano, halogen, nitro, and trihalomethyl. In some embodiments of the present invention, for example, in some embodiments wherein the ary group is phenyl, the aryl groups are optionally substituted with from 1 to 5 substituents selected from the group consisting of hydrogen, hydroxy, aryl, acyl, C1-C6 alkoxy, C2-C6 alkenyl, C2-C6 alkynyl, substituted alkyl, substituted alkoxy, substituted alkenyl, substituted alkynyl, amino, amino substituted by one or two C1-C6 alkyl groups, cyano, halogen, nitro, and trihalomethyl.

The term "heteroaryl" refers to an aryl group that contains one to four heteroatoms selected from N, O, and S. Specifically included within the definition of "heteroaryl" are those heteroaryl groups that are optionally substituted. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl. Specifically included within the definition of "alkoxy" are those alkoxy groups that are optionally substituted.

Various groups, including alkyl, heteroalkyl, cycloalkyl, heterocyclyl, aryl, heteroaryl, and alkoxy, are described herein as substituted or unsubstituted (i.e., optionally substituted). Optionally substituted groups may include one or more substituents independently selected from: CF—, $CF_3O$, halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and heteroaryl. In certain aspects the substituents may be further substituted with one or more substituents independently selected from: halogen, nitro, cyano, hydroxy, amino, mercapto, formyl, carboxy, carbamoyl, alkyl, heteroalkyl, alkoxy, alkylthio, alkylamino, (alkyl)$_2$amino, alkylsulfinyl, alkylsulfonyl, arylsulfonyl, cycloalkyl, heterocyclyl, aryl, or heteroaryl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means oxygen that is double bonded to a carbon atom.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base, such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the three dimensional configuration of those atoms differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

II. Pharmaceutical Formulations and Administration

In certain embodiments, the invention also provides compositions comprising one or more NRF2 dependent gene expression activator of Formula I and/or Formula II with one or more of the following: a pharmaceutically acceptable diluent; a carrier; a solubilizer; an emulsifier; a preservative; and/or an adjuvant. Such compositions may contain an effective amount of at least one NRF2 dependent gene expression activator. Thus, the use of one or more NRF2 dependent gene expression activator as provided herein for the preparation of a medicament is also included. Such compositions can be used in the treatment of a variety of NRF2 dependent gene expression associated diseases or conditions such as pulmonary fibrosis, acute lung injury, cancer, neurodegenerative disorders, chronic inflammatory diseases, diabetes, autoimmune disease or aging.

An NRF2 dependent gene expression activator may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the NRF2 dependent gene expression activator, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to an organ or a tumor is also contemplated by the present invention. When administering the compositions by injection, the administration may be by continuous infusion or by single or multiple boluses. For parenteral administration, the NRF2 dependent gene expression activator may be administered in a pyrogen-free, parenterally acceptable aqueous solution comprising the desired NRF2 dependent gene expression activator in a pharmaceutically acceptable vehicle. A particularly suitable vehicle for parenteral injection is sterile distilled water in which one or more NRF2 dependent gene expression activator are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

Therapeutically effective doses will be easily determined by one of skill in the art and will depend on the severity and course of the disease, the patient's health and response to treatment, the patient's age, weight, height, sex, previous medical history and the judgment of the treating physician.

The amount of one of more NRF2 dependent gene expression activator or composition comprising one of more NRF2 dependent gene expression activator that is administered to a subject can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg of total NRF2 dependent gene expression activator, or any range derivable therein. Alternatively, the amount administered may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mg/kg of NRF2 dependent gene expression activator, or any range derivable therein, with respect to the weight of the subject.

When provided in a discrete amount, each intake of one of more NRF2 dependent gene expression activator or composition comprising one of more NRF2 dependent gene expression activator can be considered a "dose." A medical practitioner may prescribe or administer multiple doses over a particular time course (treatment regimen) or indefinitely.

The pharmaceutical composition may be administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that one of more NRF2 dependent gene expression activator may be taken for an indefinite period of time or for as long as the patient exhibits symptoms of the medical condition for which the therapeutic agent was prescribed. Also, one of more NRF2 dependent gene expression activator may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

In some methods of the invention, an NRF2 dependent gene expression activator is administered to a cancer cell. The cancer cell may be in a patient and the patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intraarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

The term "fibrosis" refers to excessive growth of fibrous connective tissue in an organ, part, or tissue. The phrase "pulmonary fibrosis" refers to excessive growth of fibrous connective tissue in a lung. Pulmonary fibrosis can be idiopathic pulmonary fibrosis, pulmonary fibrosis that accompanies lung diseases such as sarcoidosis or other interstitial lung diseases (e.g., those associated with collagen vascular diseases), fibrosis caused by drug toxicity (e.g., that associated with bleomycin or amiodarone), or fibrosis caused by irradiation.

Acute lung injury refers to conditions generally involving bilateral pulmonary infiltrates on chest X-ray, a pulmonary capillary wedge pressure of less than 18 mm Hg, and a $PaO_2/FiO_2$ of less than 300. Acute lung injury includes hypoxemic respiratory syndrome and acute respiratory distress syndrome (ARDS). ARDS is one of the most severe forms of acute lung injury. ARDS may be caused by include sepsis, pulmonary aspiration, pneumonias, major trauma, burns, and infections (e.g., with the severe acute respiratory syndrome (SARS) coronavirus).

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

CBR-470-1 Inhibits PGK1 and Activates NRF2-Dependent Gene Expression

A. Results and Discussion

Figure 4:
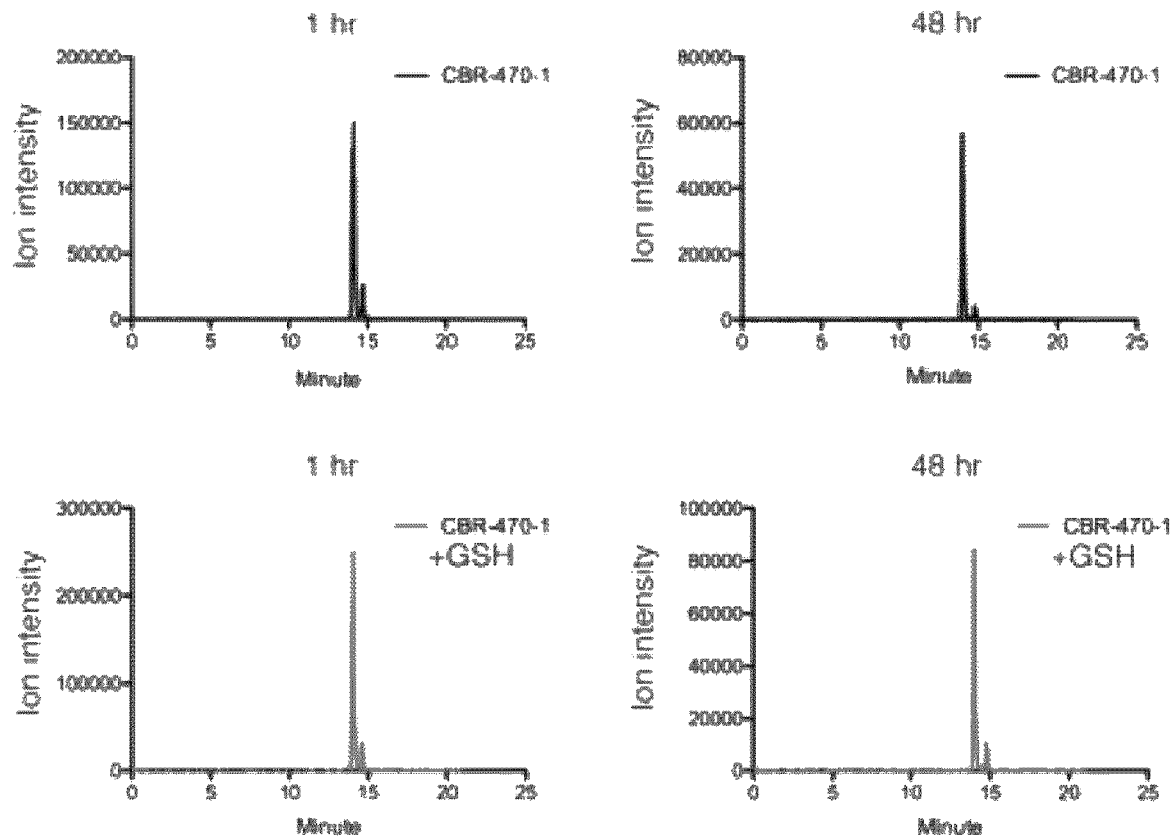
FIG. 4 A high throughput screen identifies a non-covalent NRF2 activator chemical series which activate a robust NRF2 transcriptional program in multiple cell types. LC-MS quantification of CBR-470-1 (50 μM) incubated in the presence or absence of GSH (1 mM) in PBS for 1 hour (left) and 48 hours (right). Relative ion intensities within each time point were compared with representative chromatograms shown (n=2).

To discover noncovalent modulators of the KEAP1-NRF2 signaling axis, as well as potentially novel mechanisms of action for its regulation, a cell-based, high-throughput phenotypic screen using a NRF2-dependent luciferase reporter (pTI-ARE-LUC) in IMR32 cells[15] was performed. Structure activity relationship (SAR) elaboration around the cyclic sulfone scaffold afforded CBR-470-1 an isobutylamine substituted analog that was not reactive in glutathione assays (FIG. 4).

Whether CBR-470-1 and related analogs induce activation of NRF2 signaling in vivo was determined. Published studies in NRF2-knockout mice have demonstrated that NRF2 is essential to protect against photo-aging phenotypes and skin carcinogenesis resulting from UV irradiation. The combined pharmacodynamic and efficacy data indicate that CBR-470-2 treatment is capable of modulating NRF2 signaling in vivo, despite this compound series operating via an apparent mechanism that is independent of direct KEAP1 binding.

Figure 1B:
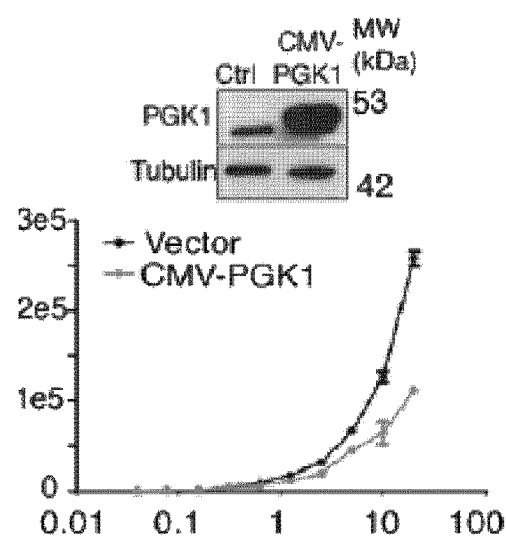
Figure 5A:
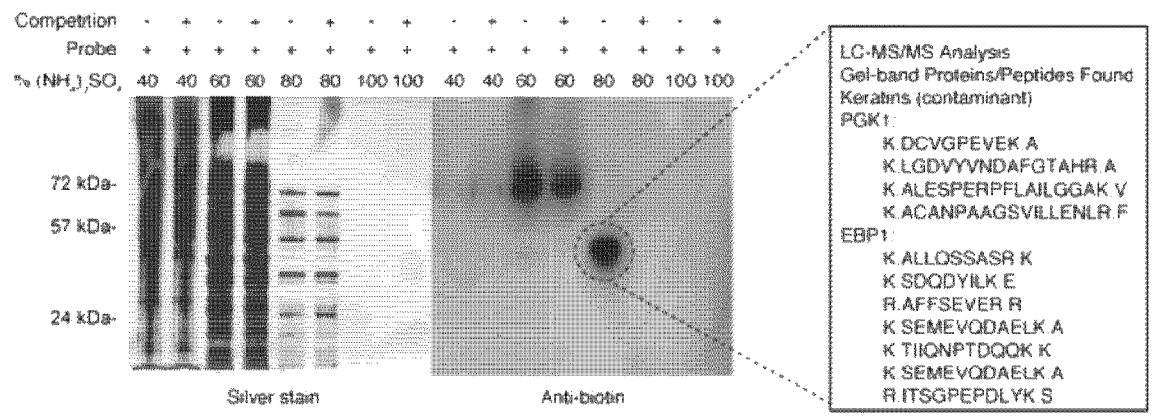
FIG. 5A-E. A photoactivatable affinity probe-based approach identifies PGK1 as the relevant cellular target of CBR-470-1. (a) Silver staining and anti-biotin Western blots of ammonium sulfate fractionated lysates from UV-irradiated IMR32 cells treated with 5 μM for 1 hour with or without CBR-470-1 competition (250 μM) (n=3). Shown on the right are initial proteomic target results from gel-band digestion and LC-MS/MS analysis. (b) Dye-based thermal denaturation assay with recombinant PGK1 in the presence CBR-470-1 (20 μM) or vehicle alone (n=3). Calculated $T_m$ values are listed. (c, d) Dose-dependent thermal stability assay of recombinant PGK1 and GAPDH in the presence of increasing doses of CBR-470-1 near the $T_m$ of both proteins (57° C.) (c) (n=5) or room temperature (d) (n=3). Western blot of sample supernatants after centrifugation (13,000 rpm) detected total PGK1 and GAPDH protein, which were plotted in Prism (below). (e) ARE-LUC reporter activity in HEK293T cells with transient shRNA.
Figure 5B:
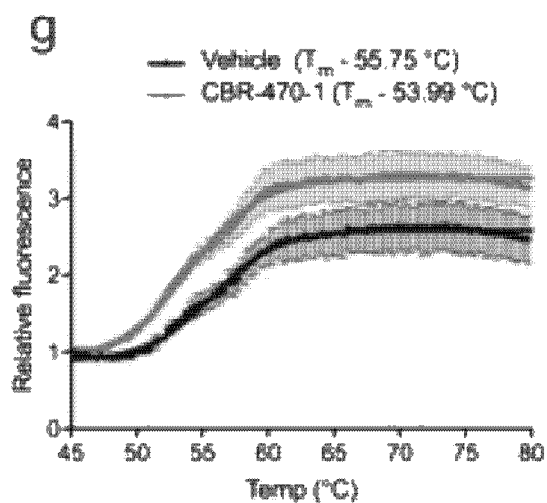
Figures 5C, 5D, 5E:
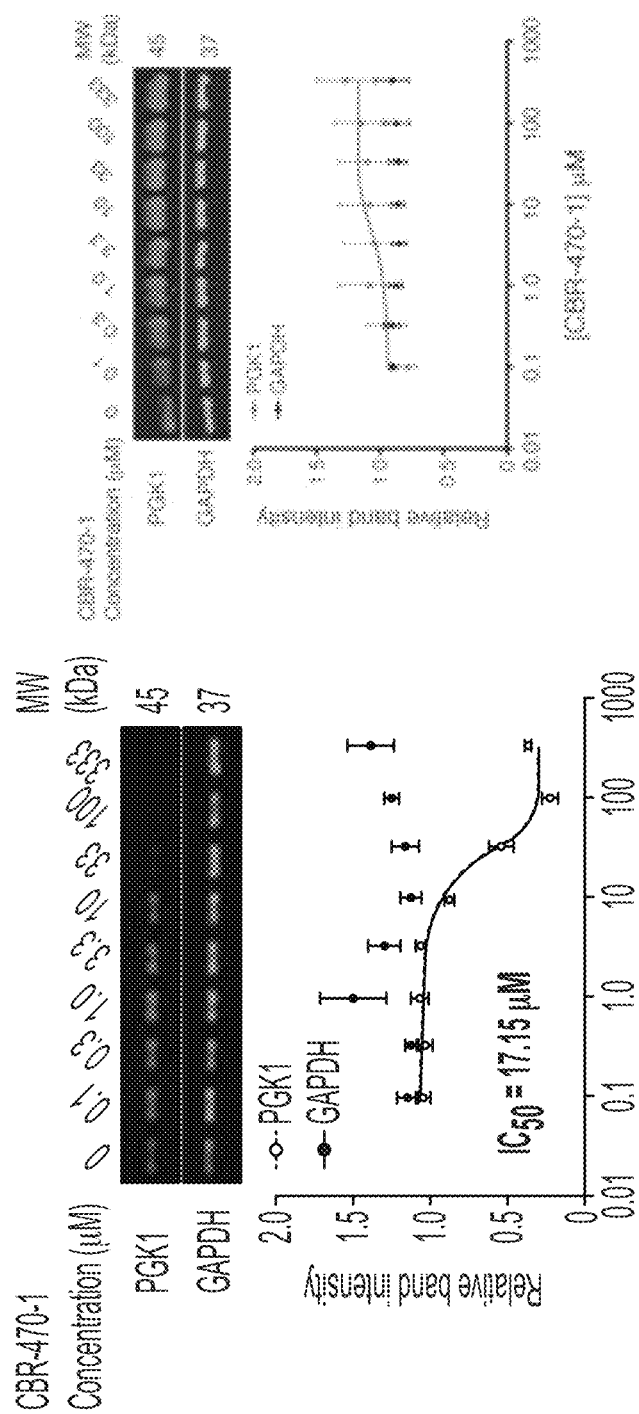

To determine the mechanism by which CBR-470-1 activates NRF2 signaling, a photo-affinity probe containing biotin and diazirine substituents, termed CBR-470-PAP (FIG. 5), was generated. Biochemical fractionation and LC-MS/MS analysis identified the enzyme phosphoglycerate kinase 1 (PGK1) as a potential target of CBR-470-PAP (FIG. 5a). Thermal stability assays in the presence of CBR-470-1 resulted in a consistent shift in PGK1 stability, and isothermal dose response profiling[19] against PGK1 and GAPDH also confirmed the selective, dose-dependent alteration of PGK1 stability in the presence of CBR-470-1 (FIG. 5b-d). Knockdown or overexpression of PGK1 protein modulated the NRF2-reporter, with decreased and increased observed CBR-470-1 EC50 values, respectively (FIG. 1a-b). Finally, depletion of enolase 1, an enzyme downstream of PGK1, was also found to induce ARE-LUC signal in IMR32 cells (FIG. 5e). These results suggested that CBR-470-1 modulation of PGK1 activity, and therefore glycolysis, regulates NRF2 activation.

Figure 1C:
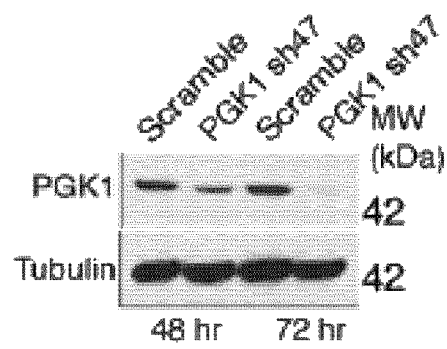
Figure 1D:
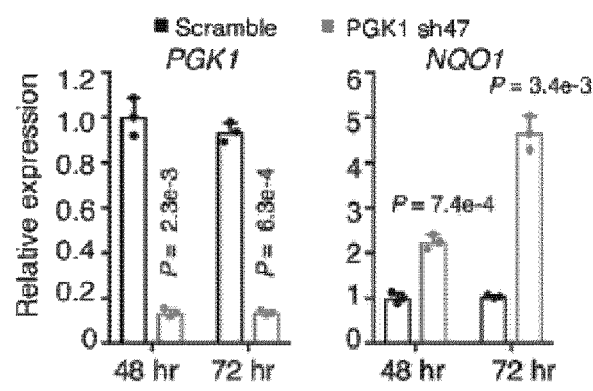
Figure 6C:
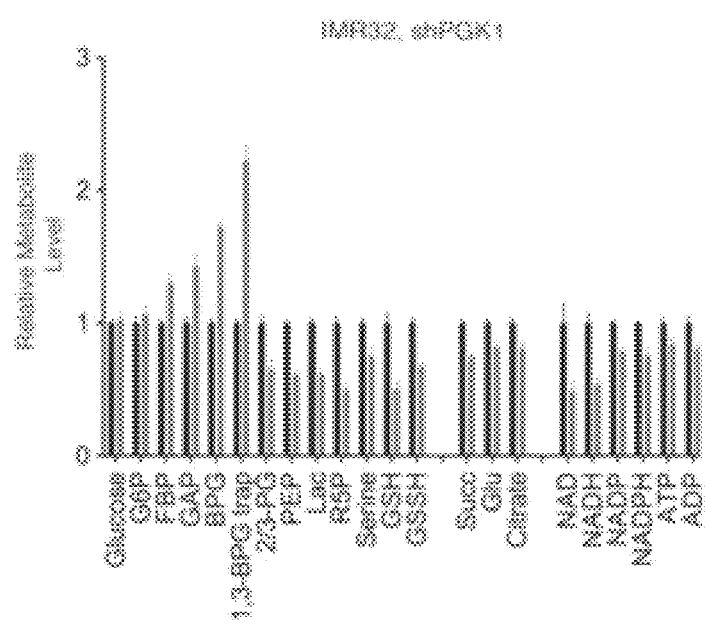
Figure 6D:
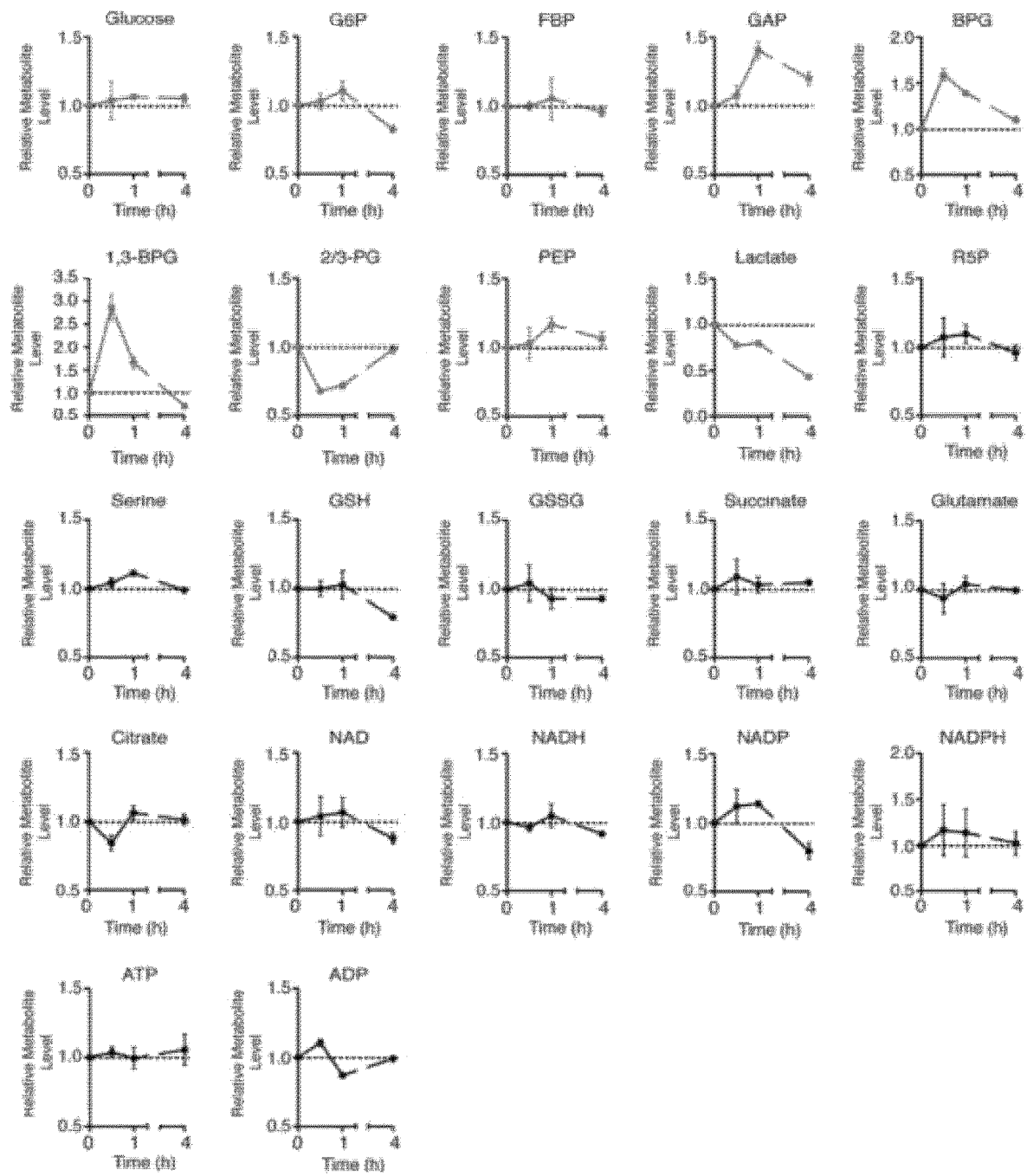

Consistent with the PGK1 inhibitory activity of CBR-470-1 (FIG. 6a-b), targeted metabolomic profiling[4, 20] of IMR32 cells treated with compound revealed a rapid increase in metabolite levels upstream of PGK1 (1,3- and 2,3-bisphosphoglycerate [BPG], and D-glyceraldehyde-3-phosphate [GAP]), and depletion of downstream metabolites such as 3-phosphoglycerate (3PG) and lactate (Lac), which mirrored the profile observed upon viral knockdown of PGK1 in IMR32 cells (FIG. 1c; FIG. 6c-d). Taken together, these data suggested that glycolytic intermediates may serve as a signal to the NRF2 signaling axis.

Figure 2A:
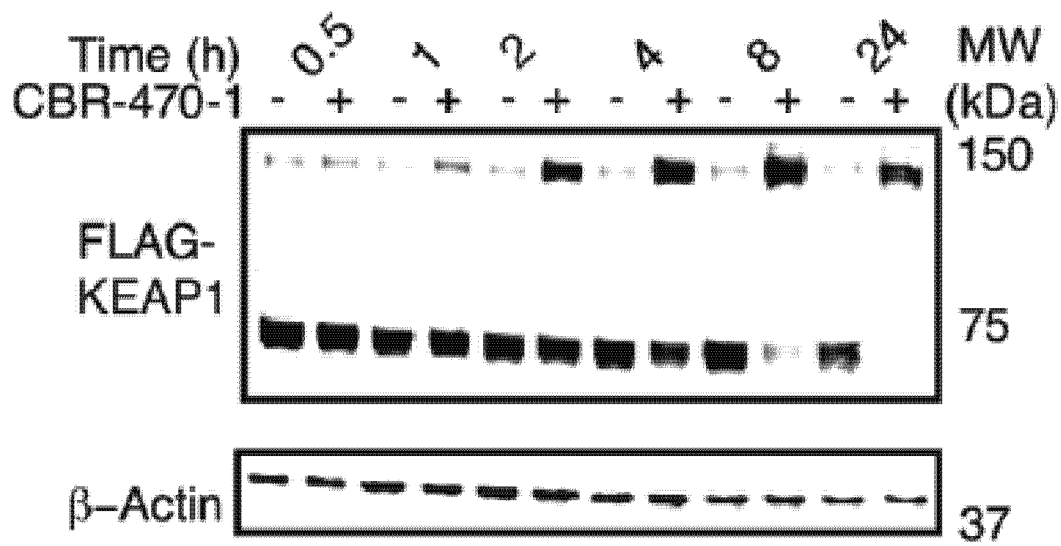
FIG. 2A-F. Methylglyoxal modifies KEAP1 to form a covalent, high molecular weight dimer and activate NRF2 signaling. (a) Time-course, anti-FLAG Western blot analysis of whole cell lysates from HEK293T cells expressing FLAG-KEAP1 treated with DMSO or CBR-470-1. (b) Western blot monitoring of FLAG-KEAP1 migration in HEK293 T lysates after incubation with central glycolytic metabolites in vitro (1 and 5 mM, left and right for each metabolite). (c) FLAG-KEAP1 (red) and β-actin (green) from HEK293T cells treated with MGx (5 mM) for 8 hr. (d) Relative NQO1 and HMOX1 mRNA levels in IMR32 cells treated with MGx (1 mM) or water control (n=3). (e) LC-MS/MS quantitation of cellular MGx levels in IMR32 cells treated with CBR-470-1 relative to DMSO (n=4). (f) ARE-LUC reporter activity in HEK293T cells with transient shRNA knockdown of GLO1 (n=8). Univariate two-sided t-test (d, f); data are mean±SEM of biologically independent samples.
Figure 7C:
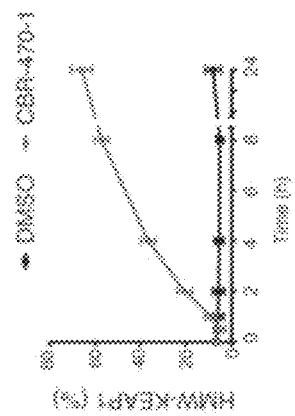
FIG. 7A-F. Modulation of PGK1 induces HMW-KEAP1. (a) Anti-pgK (phosphoglyceryl-lysine) and anti-GAPDH Western blots analysis of CBR-470-1 or DMSO-treated IMR32 cells at early (30 min) and late (24 hr) time points (n=6). (b) Anti-FLAG (left) and anti-pgK (right) Western blot analysis of affinity purified FLAG-KEAP1 from HEK293T cells treated with DMSO or CBR-470-1 for 30 min. Duplicate samples were run under non-reducing (left) and reducing (DTT, right) conditions (n=6). (c) Densitometry quantification of total endogenous KEAP1 levels (combined bands at ~70 and 140 kDa) in IMR32 cells treated with DMSO or CBR-470-1 for the indicated times (n=6). (d) Western blot detection of FLAG-KEAP1 in HEK293 T cells comparing no-reducing reagent to DTT (left), and stability of CBR-470-1-dependent HMW-KEAP1 to the presence of DTT (12.5 mM final concentration, middle) and beta-mercaptoethanol (5% v/v final concentration, right) during sample preparation. treated with DMSO or CBR-470-1 for 8 hours (n=8). (e) Transient shRNA knockdown of PGK1 induced HMW-KEAP1 formation, which was blocked by co-treatment of cells by GSH (n=3). (f) Anti-FLAG Western blot analysis of FLAG-KEAP1 monomer and HMW-KEAP1 fraction with dose-dependent incubation of distilled MGx in lysate from HEK-293T cells expressing FLAG-KEAP1 (n=4). (g) SDS-PAGE gel (silver stain) and anti-FLAG Western blot analysis of purified KEAP1 treated with the MGx under the indicated reducing conditions for 2 hr at 37° C. (n=3). Purified protein reactions were quenched in 4xSDS loading buffer containing βME and processed for gel analysis as in (d). Data shown represent mean±SEM of biologically independent samples.
Figure 7F:
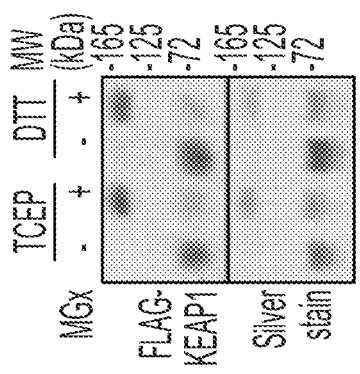
Figure 7B:
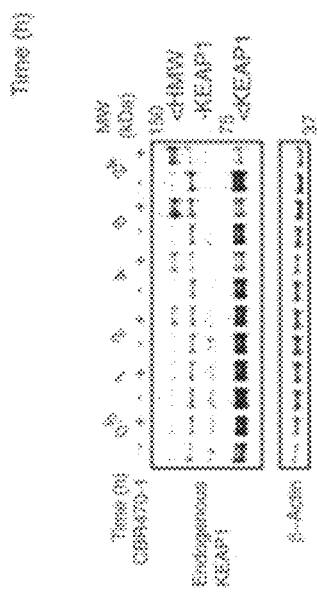
Figure 7E:
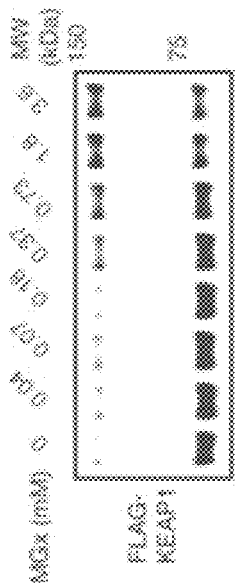
Figure 7A:
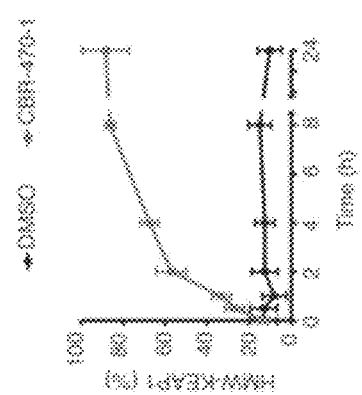
Figure 7D:
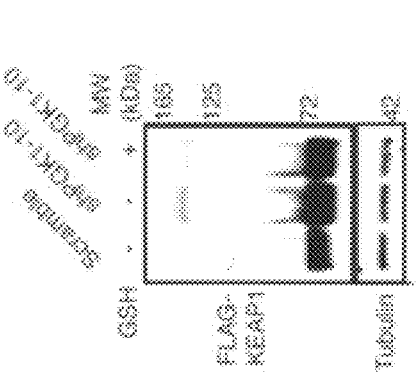

It was analyzed whether 1,3-BPG, which is directly metabolized by PGK1, could be involved in signaling to the KEAP1-NRF2 pathway via phosphoglyceryl-lysine (pgK) modification of KEAP1. However, CBR-470-1 treatment of IMR32 cells for 30 minutes, a time at which 1,3-BPG levels are elevated, did not result in altered KEAP1 levels, or any α-pgK immunoreactive bands using polyclonal antibodies raised against the phosphoglyceryl-lysine epitope (FIG. 7a-c). These Western blots did, however, reveal the appearance of a CBR-470-1-dose-dependent, high molecular weight KEAP1 (HMW-KEAP1) band at roughly twice the molecular weight of monomeric KEAP1 (FIG. 2a). The HMW-KEAP1 band was stable to reduction (FIG. 7d) and exhibited kinetics and dose-dependent formation consistent with CBR-470-1-dependent NRF2 stabilization and NQO1 induction, but distinct from the direct KEAP1 alkylator tBHQ Knockdown of PGK1, which activates NRF2 target gene expression, also formed HMW-KEAP1, and this band was competed by co-treatment with GSH (FIG. 7e). Together these data indicated that modulation of glycolysis by CBR-470-1 results in the formation of a HMW-KEAP1 that is consistent with a covalent KEAP1 dimer, which has been previously observed[21-23], but remained uncharacterized at the molecular level. Viability assays were performed in IMR32, OVCAR3, and A549 cell lines with compound treatment with CBR-470-1. Concentrations ranging from 0.1 to 30 micromolar for 48 hr. Viability was measured using Cell titer glo ATP quantification assay. Representative curves for three cell lines at 48 are shown in (FIG. 36A). Table of 20 cell line IC50 values are shown in (FIG. 36B).

Figure 2B:
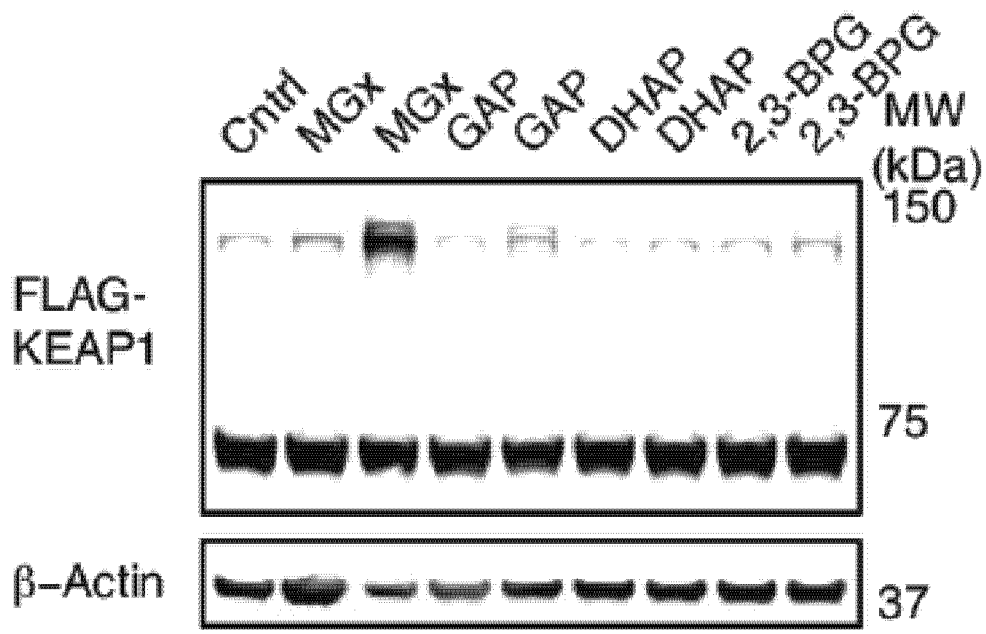
Figure 2C:
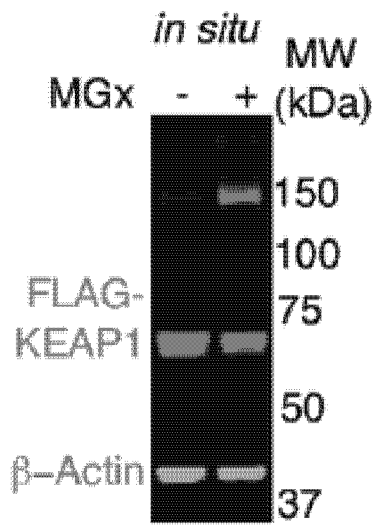
Figure 2D:
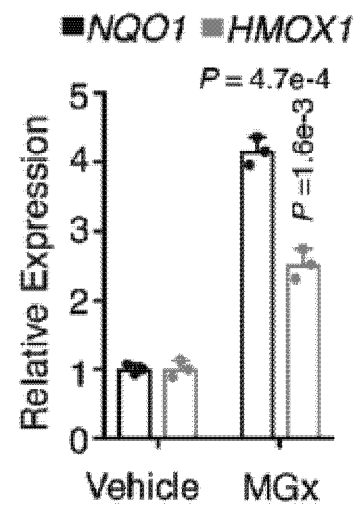
Figure 2E:
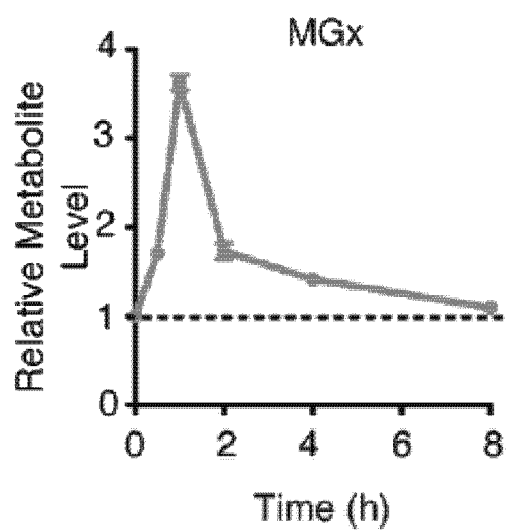
Figure 2F:
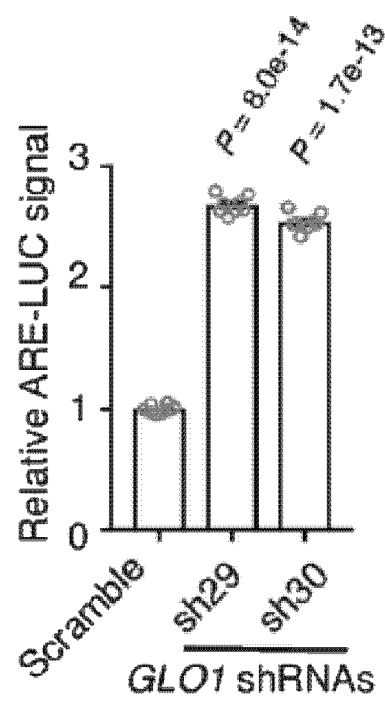

Several central glycolytic metabolites other than 1,3-BPG contain reactive functionalities, including the triosephosphate isomers D-glyceraldehyde-3-phosphate (GAP) and dihydroxyacetone phosphate (DHAP), as well as their non-enzymatic elimination product methylglyoxal (MGx), an electrophilic dicarbonyl compound that has been found to form numerous modifications on nucleophilic residues in proteins[24, 25]. Among these candidates, only treatment of cell lysates or live cells with MGx resulted in the selective formation of HMW-KEAP1 (FIG. 2b-c). Treatment of FLAG-KEAP1 containing lysates or purified KEAP1 with freshly distilled MGx induced dose-dependent formation of HMW-KEAP1 at mid-µM concentrations (FIG. 7f-g), which is consistent with the range of MGx concentrations previously reported in living cells[26, 27]. MGx treatment in cells functionally activated expression of the downstream NRF2 target genes NQO1 and HMOX1 (FIG. 2d). Targeted LC-MS measurement of derivatized methylglyoxal confirmed that CBR-470-1 treatment resulted in significant elevation of cellular MGx levels in the first few hours of treatment (FIG. 2e; FIG. 8a-c), which was sensitive to GSH treatment (FIG. 8d). To further test the involvement of MGx in KEAP1-NRF2 signaling, MGx degradation was perturbed, which is mediated by GSH and glyoxylase 1 (GLO1). Knockdown of GLO1 by shRNA resulted in ARE-LUC reporter activation (FIG. 2f). Collectively, these metabolomic, proteomic and transcriptomic data established shared kinetics between MGx accumulation, HMW-KEAP1 formation and NRF2 pathway activation, suggesting the existence of a direct link between glycolysis and the KEAP1-NRF2 signaling pathway mediated by the direct modification of KEAP1 by MGx.

Figure 9A:
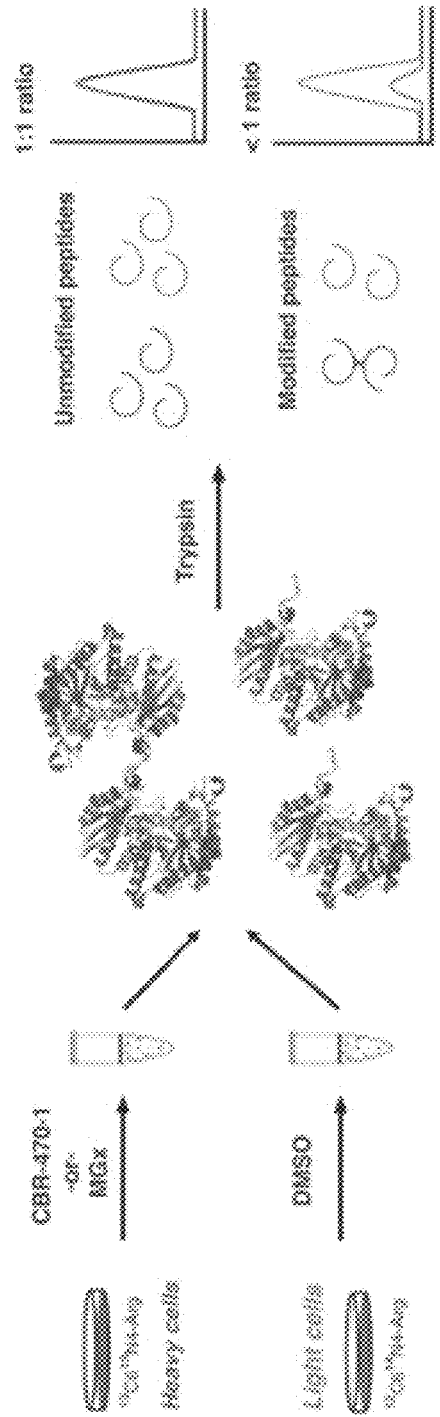
Figure 9C:
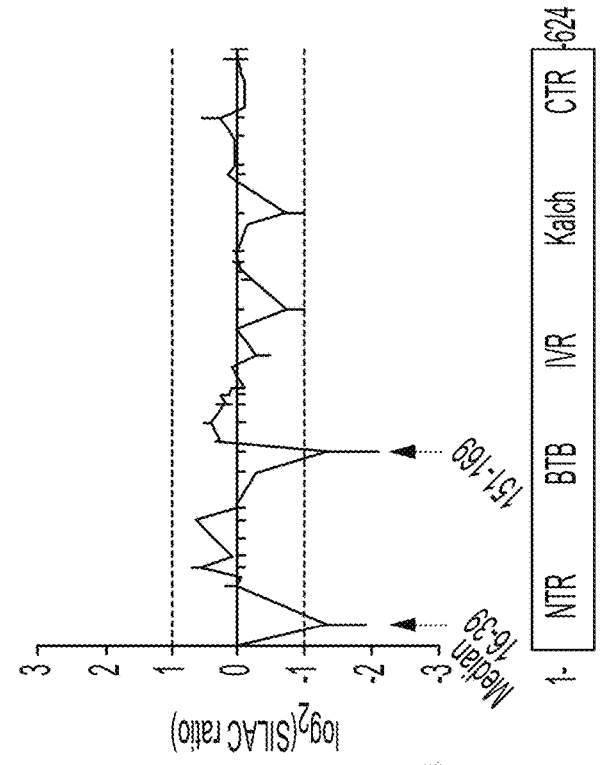
Figure 9B:
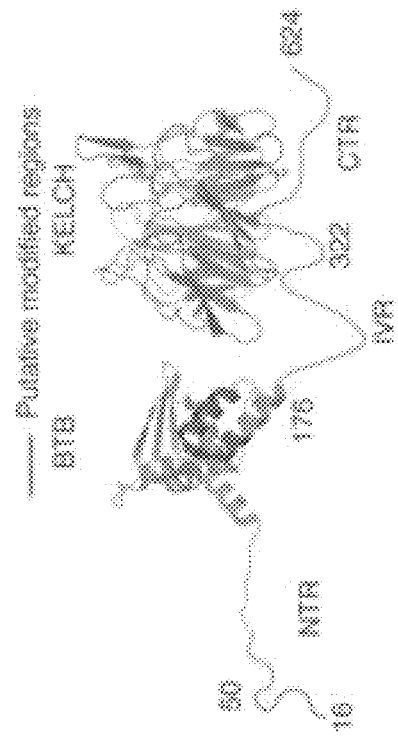

A SILAC-based quantitative proteomic approach (FIG. 9a) suggested the NTR (N-terminal region, amino acids 1-50 of KEAP1 (SEQ ID NO:1) (one example of a KEAP1 protein has amino acids MQPDPRPSGAGAC-CRFLPLQSQCPEGAGDAVMYASTECKAEVTP-SQHGNRTFSYTL EDHTKQAFGIMNELRLSQQLCD-VTLQVKYQDAPAAQFMAHKVVLASSSPVFKAMF TNGLREQGMEVVSIEGIHPKVMERLIEFAYTA-SISMGEKCVLHVMNGAVMYQIDSV VRACSD-FLVQQLDPSNAIGIANFAEQIGCVELHQRAR-EYIYMHFGEVAKQEEFFNLS HCQLVTLISRDDLNVRCESEVFHACINWV-KYDCEQRRFYVQALLRAVRCHSLTPNFL QMQLQK-CEILQSDSRCKDYLVKI-FEELTLHKPTQVMPCRAPKVGRLIYTAGGYFRQS LSYLEAYNPSDGTWLRLADLQVPRSGLAGCVVGGL-LYAVGGRNNSPDGNTDSSALD CYNPMTNQWSP-CAPMSVPRNRIGVGVIDGHIYAVGGSHGCIHHNSV-ERYEPERDEW HLVAPMLTRRIGVGVAVLNRLLYAVGGFDGTNRLN-SAECYYPERNEWRMITAMNTI RSGAGVCVLHNCI-YAAGGYDGQDQLNSVERYDVETETWTFVAPM-KHRRSALGITV HQGRIYVLGGYDGHTFLDSVECYDPDTDTW-SEVTRMTSGRSGVGVAVTMEPCRKQI DQQNCTC (SEQ ID NO:1)) and BTB domains (amino acids 95-596 of (SEQ ID NO:1) NCBI Reference Sequence: XP_011526754.1, which is incorporated herein by reference in its entirety) as candidate domains and residues that could be involved in HMW-KEAP1 formation in response to CBR-470-1-induced MGx elevation (FIGS. 9b and c). More than a dozen C-to-S, K-to-M/R, and R-to-A mutations within these domains were examined, as well as other known functional residues in KEAP1, for their effect on HMW-KEAP1 formation. Two arginine residues (R15 of the NTR domain and R135 of the BTB domain) significantly, but incompletely, reduced the formation of HMW-KEAP1 (FIG. 3a). More striking was the near complete inhibition of HMW-KEAP1 formation of the C151S mutant in the BTB domain (FIG. 3a). Consistent with this effect, C151-containing tryptic peptide levels were reduced by MGx treatment, and pre-treatment of cells with bardoxolone methyl, which alkylates C151, inhibited HMW-KEAP1 formation (FIG. 9c). C151 lies in an exposed region of the BTB domain that is predicted to mediate the homodimeric interface between two KEAP1 monomers, which is necessary for proper NRF2 binding and ubiquitination[8, 23]. Therefore, the strong abrogation of HMW-KEAP1 formation through mutation of C151 and proximal arginines suggested that MGx may be mediating an uncharacterized modification between these residues.

Figure 10A:
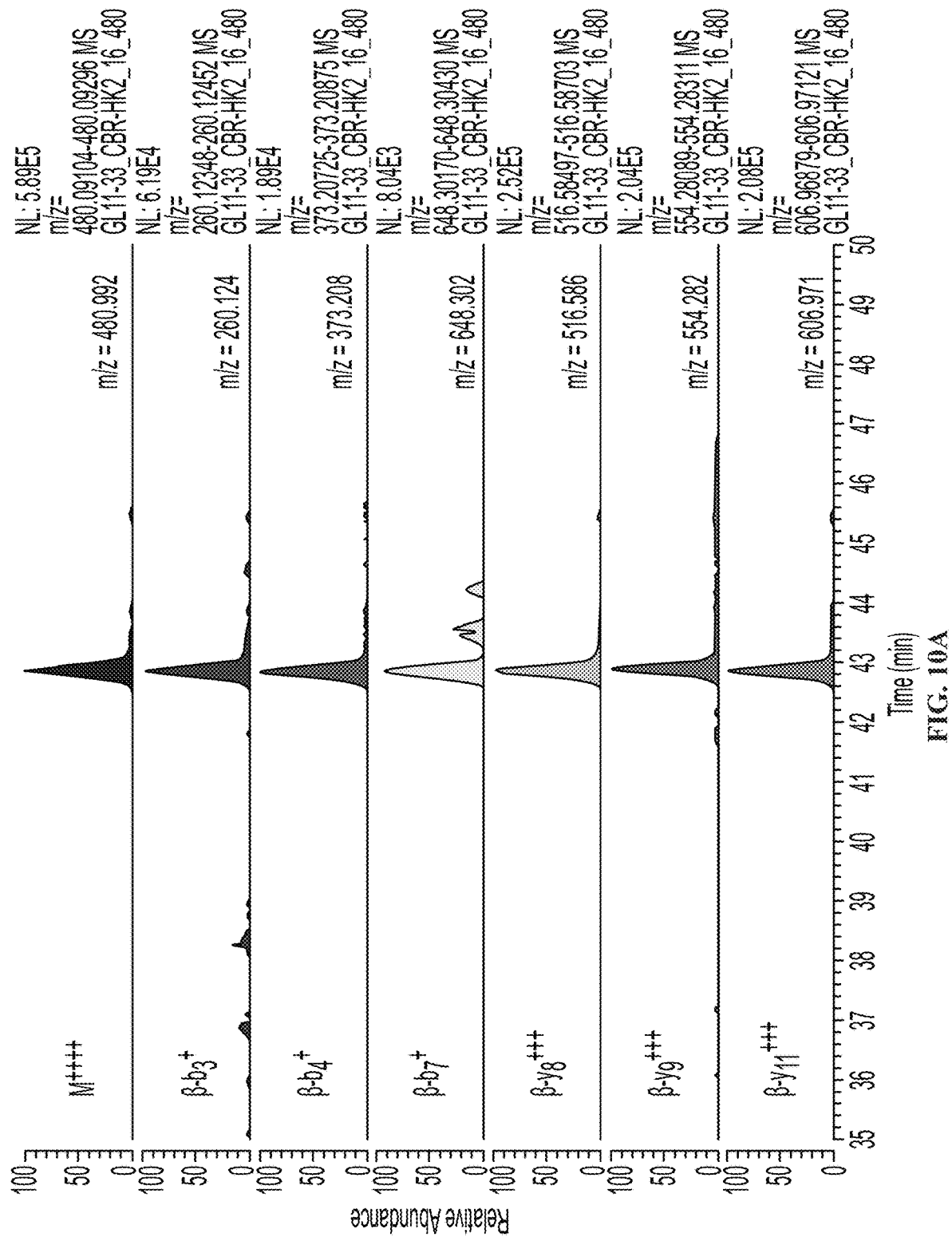
FIG. 10A-B. MS2 analysis of CR-MGx crosslinked KEAP1 peptide. (a) Targeted Parallel reaction monitoring (PRM) transitions (n=6). (b) Annotated MS2 spectrum from the crosslinked C151-R135 KEAP1 peptide.
Figure 10A:
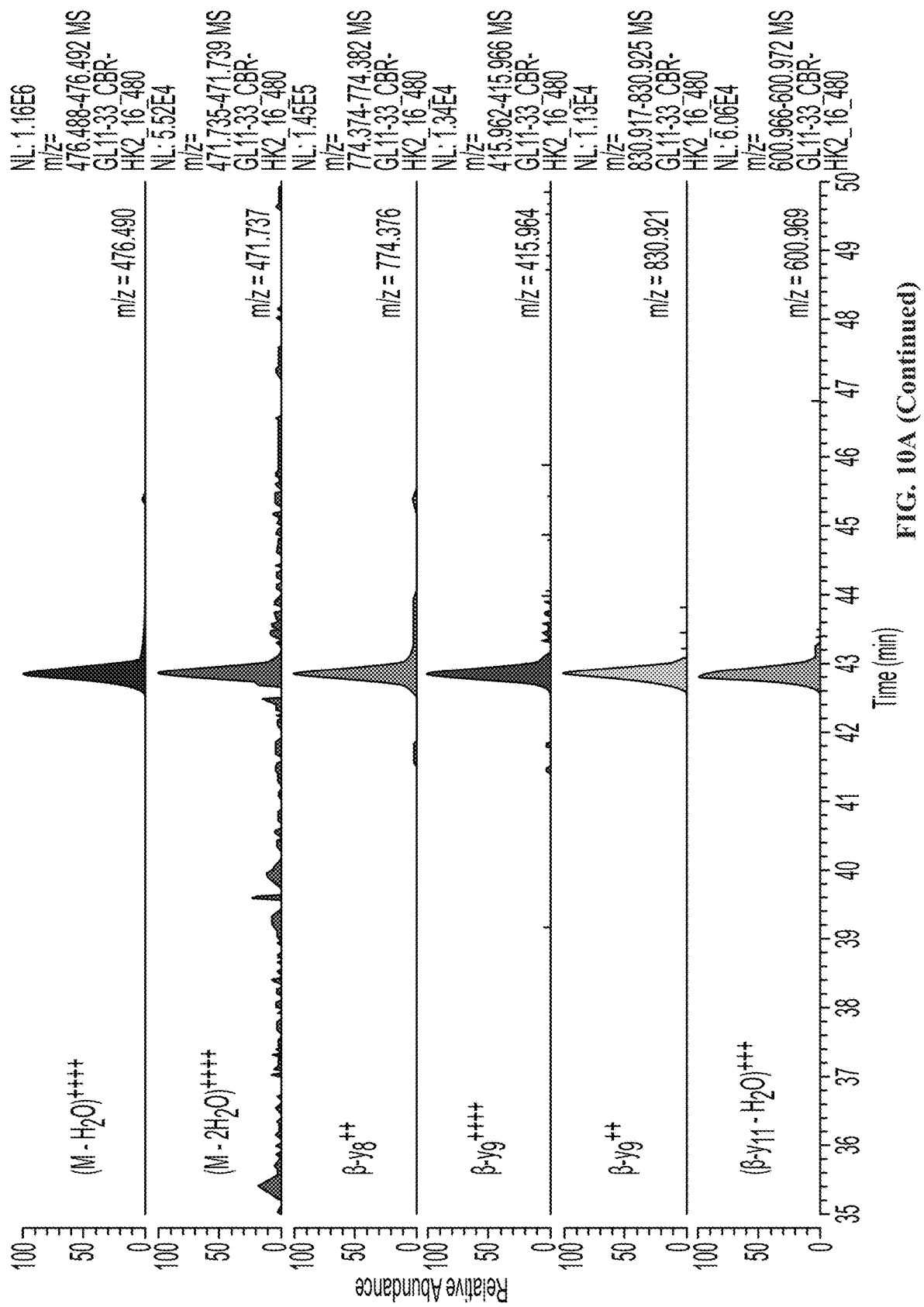
Figure 10B:
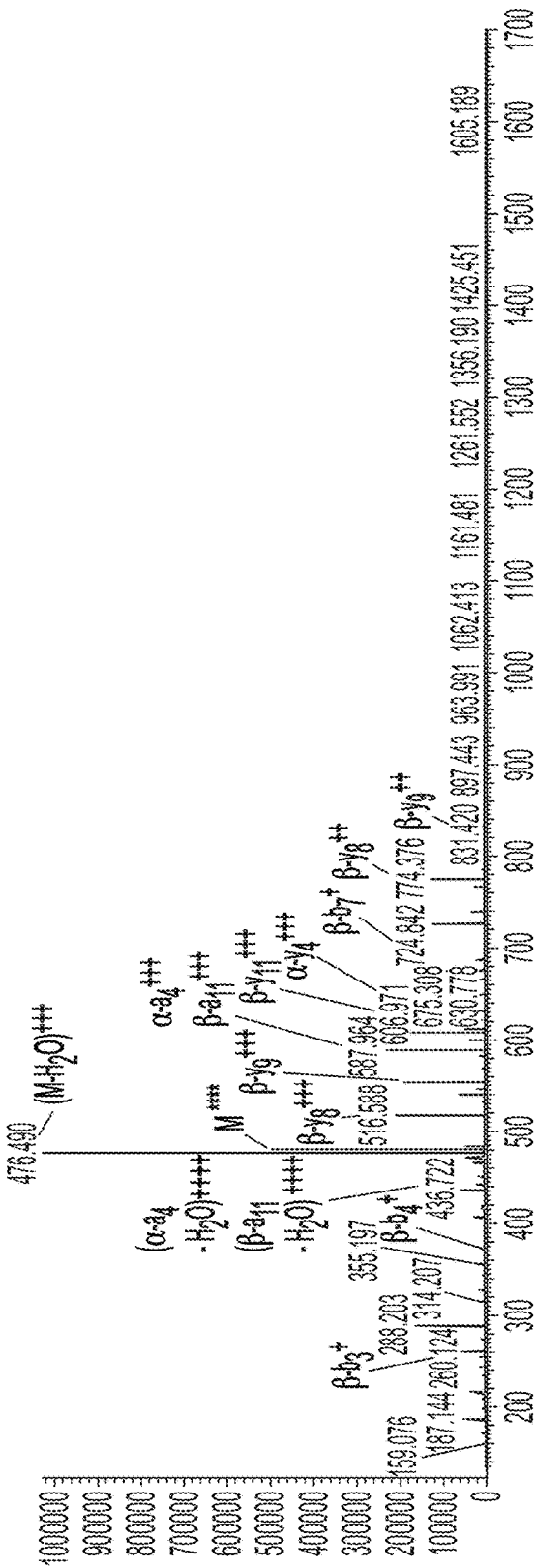
Figure 11:
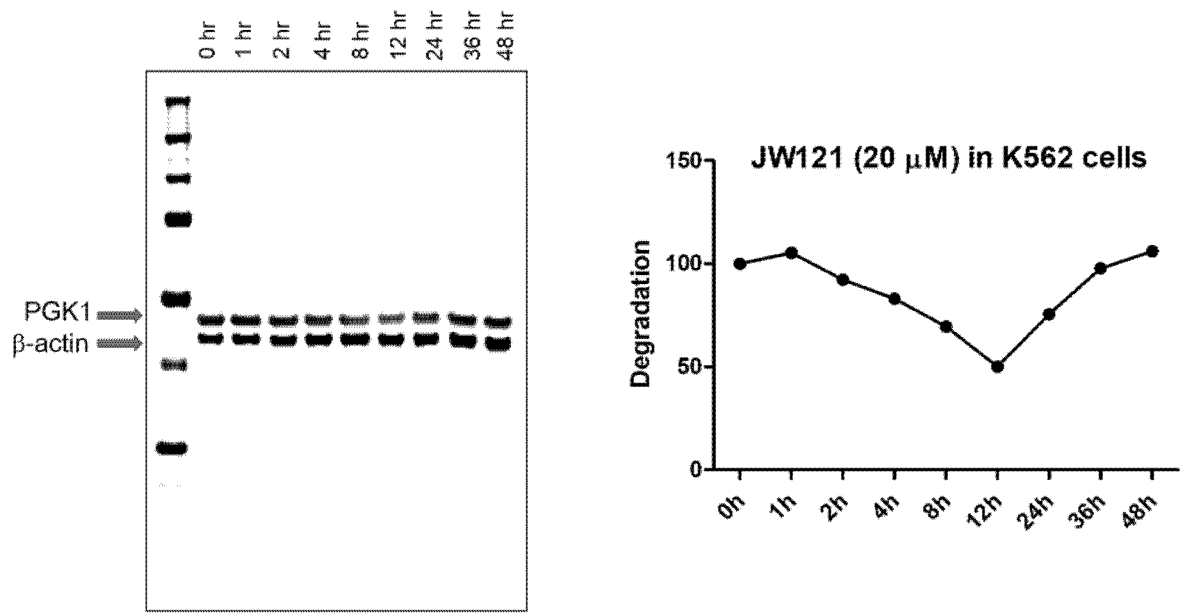
FIG. 11. (a) Western blot time course of PGK1. (b) PGK1 levels (PGK1 stability) in K562 cells in the presence of JW121.
Figure 12:
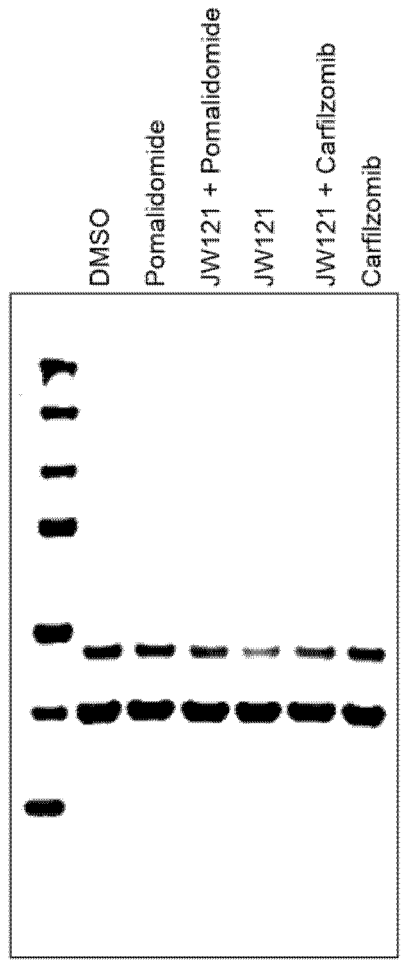
FIG. 12. PGK1 levels in the presence of JW121, Anti-angiogenic pomalidomide, proteasome inhibitor carfilzomib, and combinations thereof.
Figure 13A:
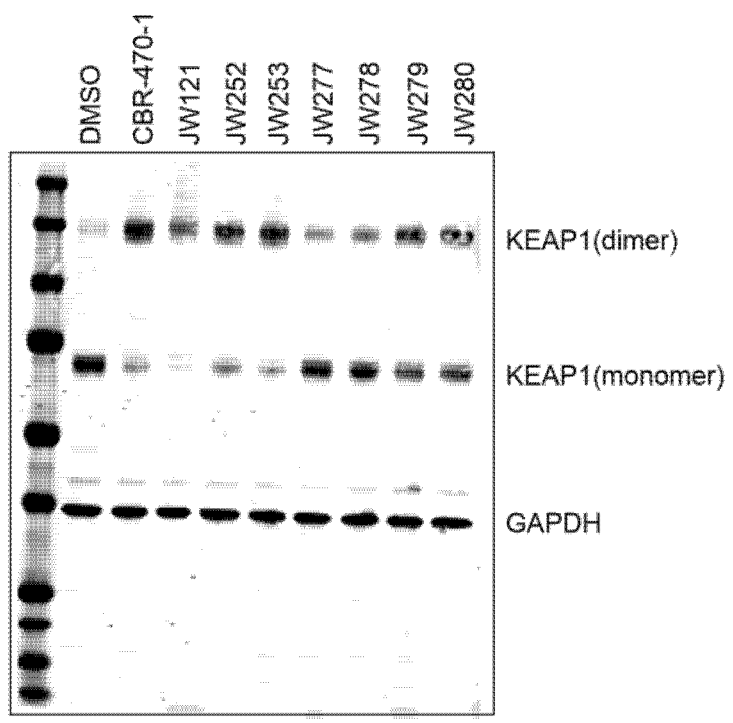
FIG. 13A-B. (a) Western blot of KEAP1 monomer and dimer when treated with DMSO, CBR 470-1, JW121, JW252, JW253, JW277, JW278, JW279, or JW280. (b) Western blot of PGK1 when treated with DMSO, CBR 470-1, JW121, JW252, JW253, JW277, JW278, JW279, or JW280.
Figure 13B:
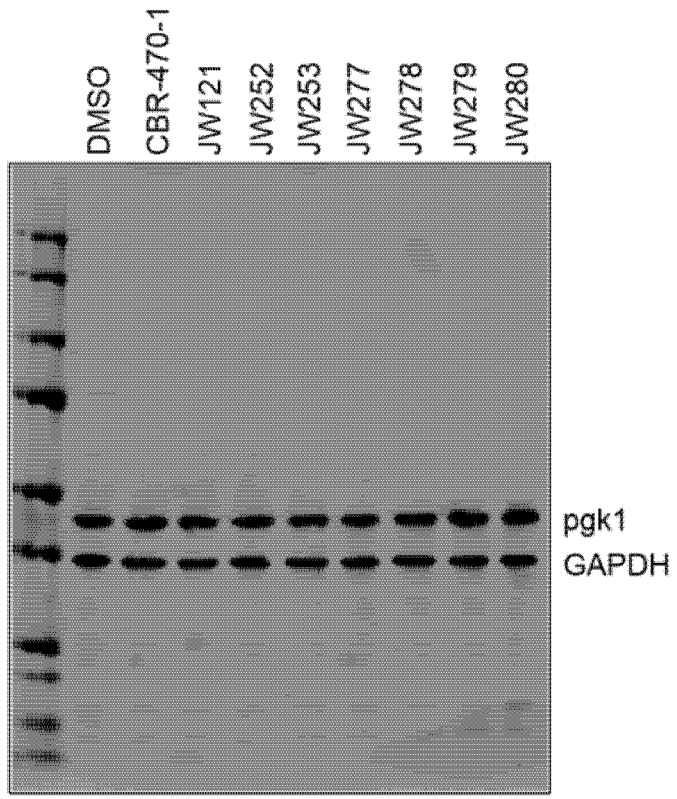
Figure 14A:
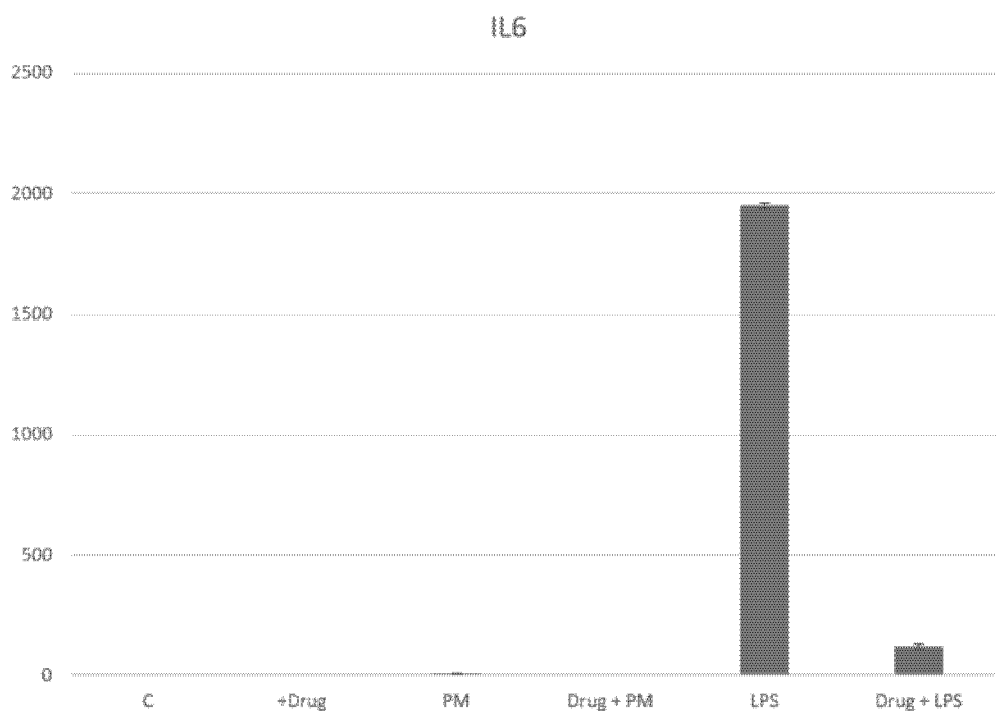
FIG. 14A-B. MHS cells (a murine alveolar macrophage cell line) were treated with particulate matter (PM) or LPS and vehicle control (media) in the absence or presence of CBR-470-1 (pretreated 4 hours prior to PM/LPS) and measured IL-6 mRNA 4 hours later. CBR-470-1 pretreatment abolished PM- and LPS-induced il6 mRNA expression in murine macrophages.
Figure 14B:
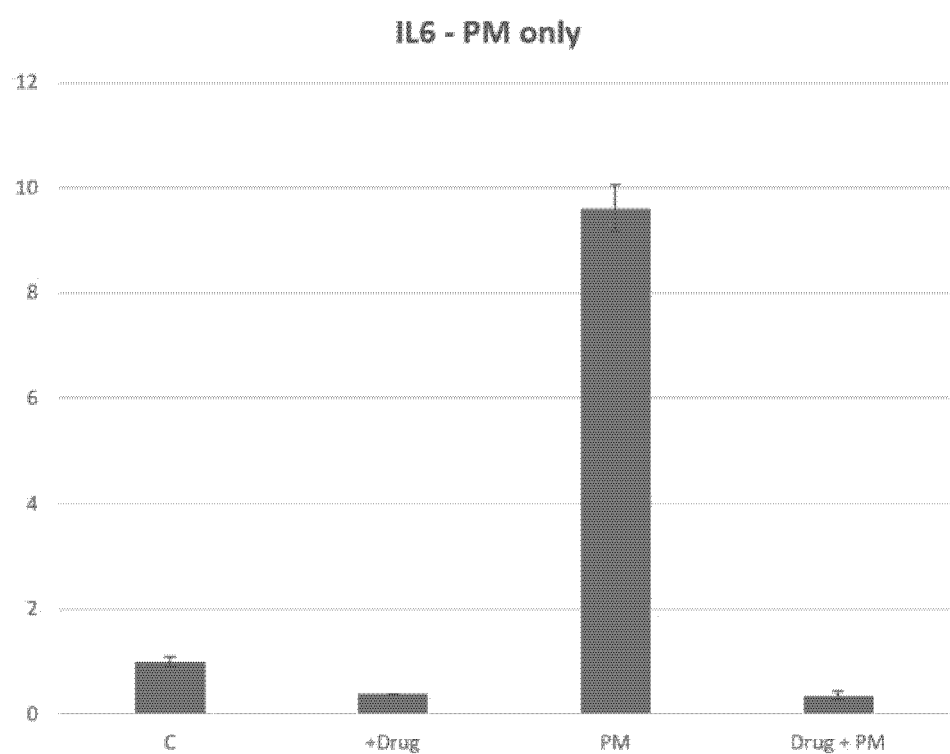
Figure 15A:
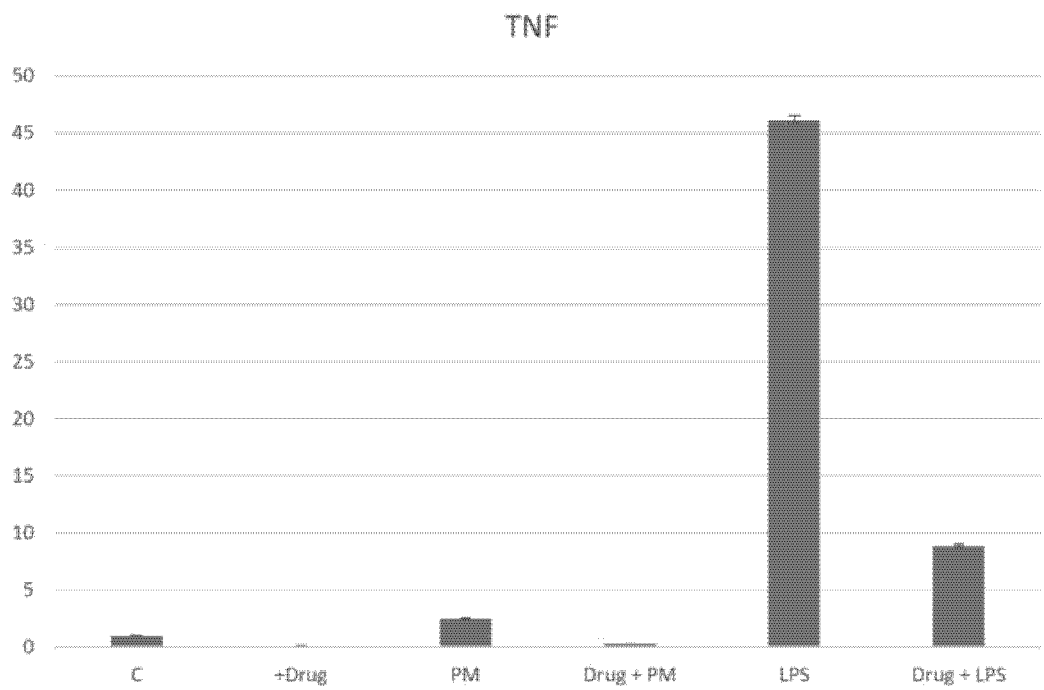
FIG. 15A-B. MHS cells were treated with particulate matter (PM) or LPS and vehicle control (media) in the absence or presence of CBR-470-1 (also noted as Drug in the figure) (pretreated 4 hours prior to PM/LPS) and measured TNFa and NQO1 mRNA 4 hours later. CBR-470-1 pretreatment abolished PM- and LPS-induced TNFa mRNA expression in murine macrophages. CBR-470-1 induced NQO1 (Nrf2 target gene) under both PM and LPS. NQO1 (NAD(P)H:quinone oxidoreductase), also known as DT-diaphorase, is a major regulator of oxidative stress and activator of mitomycins. ROS produced during metabolic processes are normally converted into harmless products by antioxidant enzymes such as NQO1.
Figure 15B:
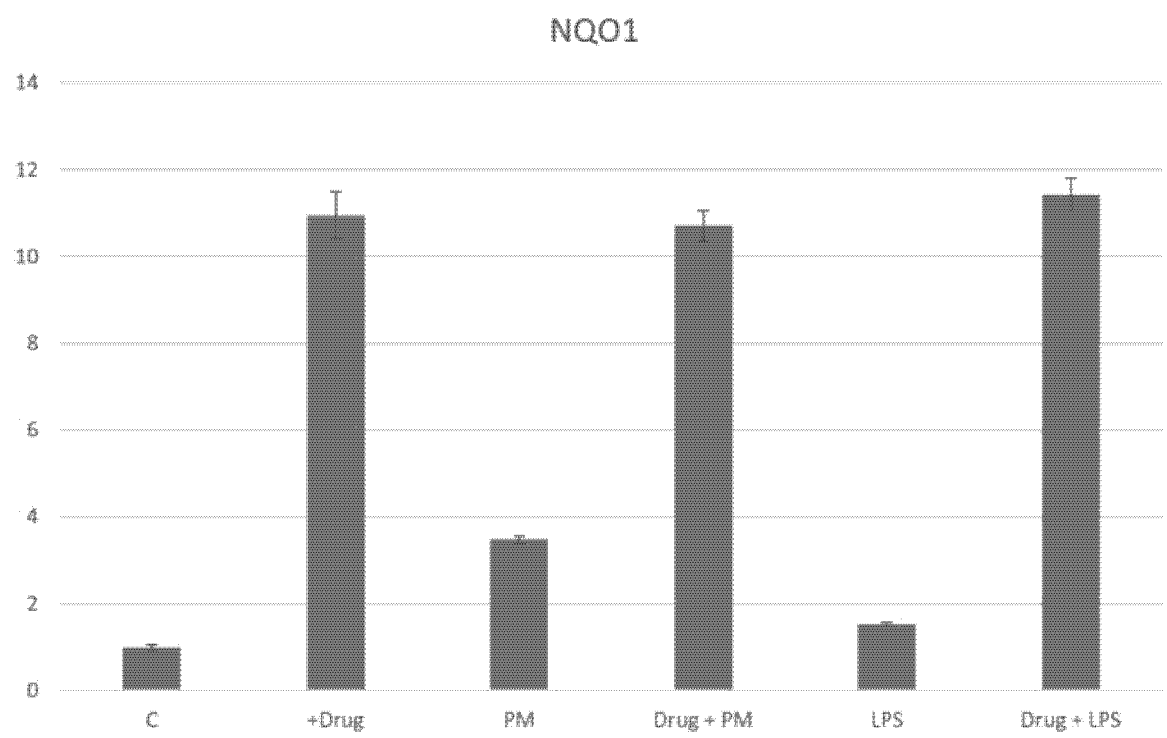
Figure 16A:
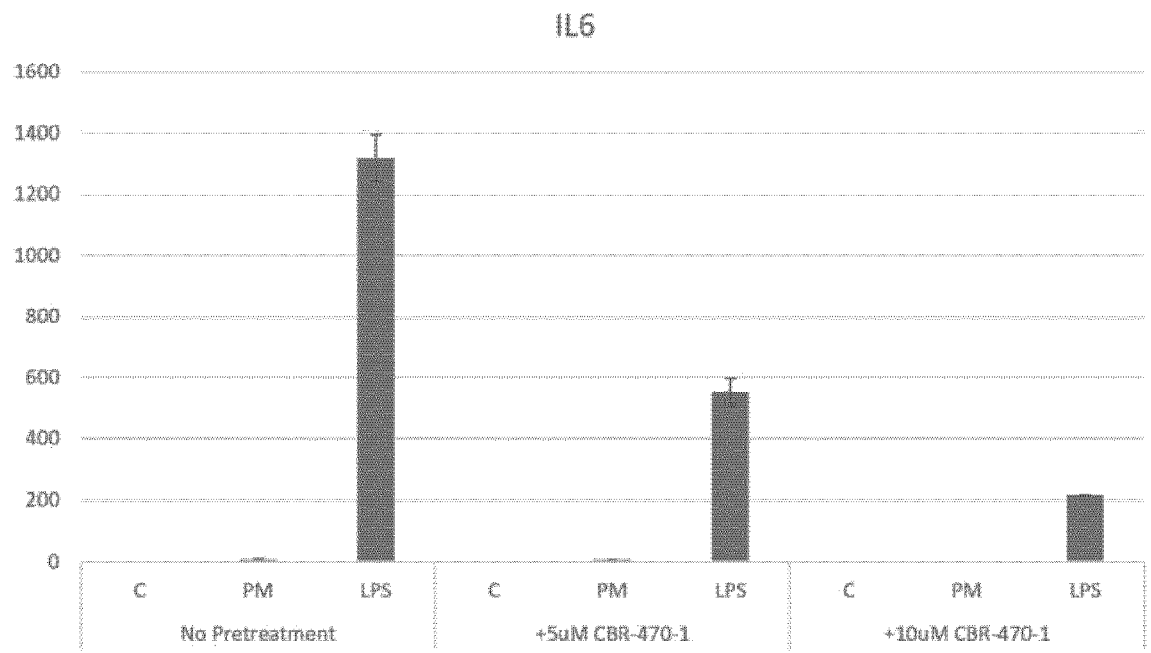
FIG. 16A-B. MHS cells were treated with particulate matter (PM) or LPS and vehicle control (media) in the absence or presence of different doses of CBR-470 (pretreated 4 hours prior to PM/LPS) and measured IL-6 mRNA 4 hours later. CBR-470 pretreatment decreased PM- and LPS-induced IL-6 mRNA expression in murine macrophages in a dose-dependent manner.
Figure 16B:
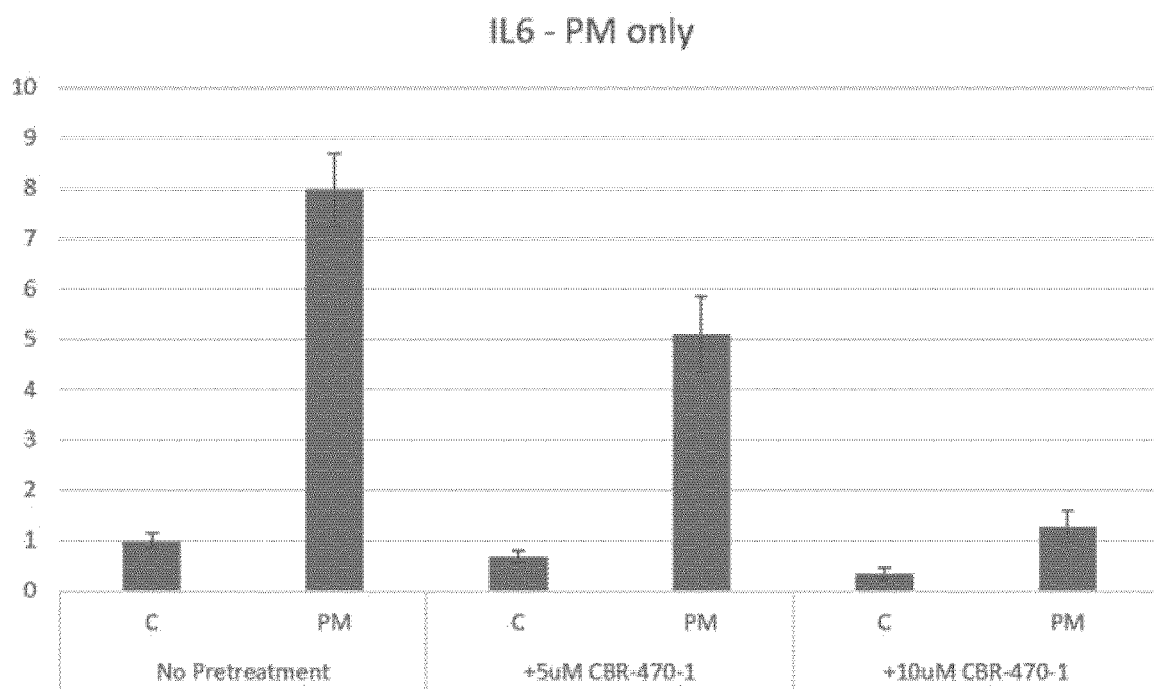
Figure 17A:
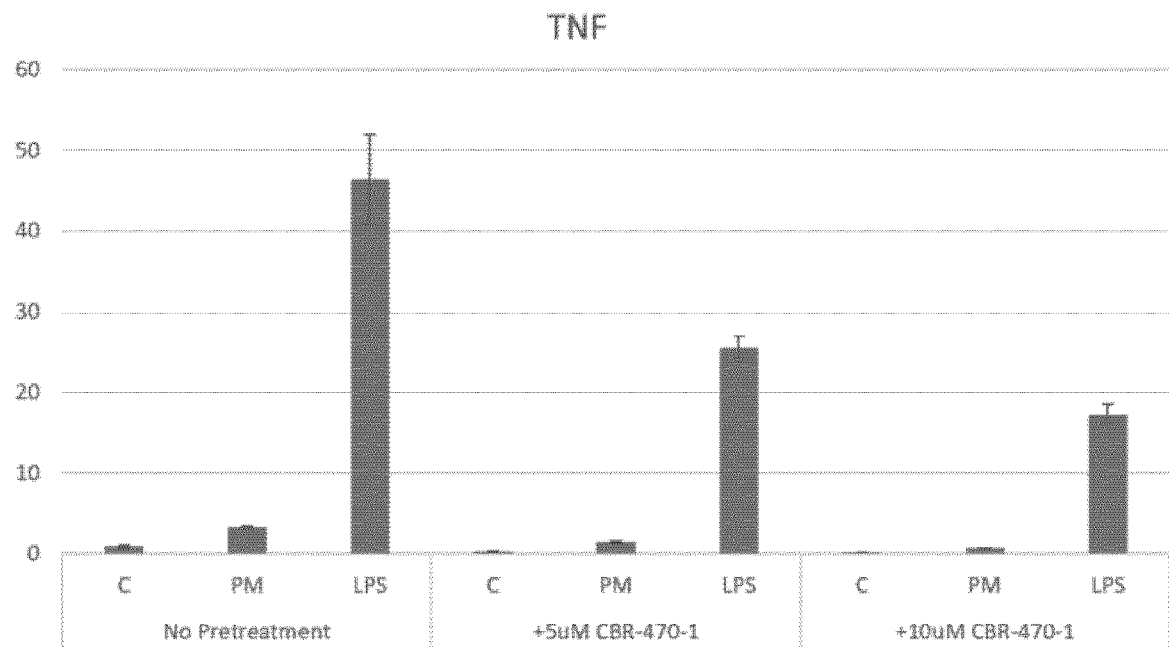
FIG. 17A-B. MHS cells were treated with particulate matter (PM) or LPS and vehicle control (media) in the absence or presence of different doses of CBR-470-1 (pretreated 4 hours prior to PM/LPS) and measured TNFa and NQO1 mRNA 4 hours later. CBR-470-1 pretreatment attenuated PM- and LPS-induced TNFa mRNA expression and induced NQO1 (Nrf2 target gene) under both PM and LPS in a dose dependent manner.
Figure 17B:
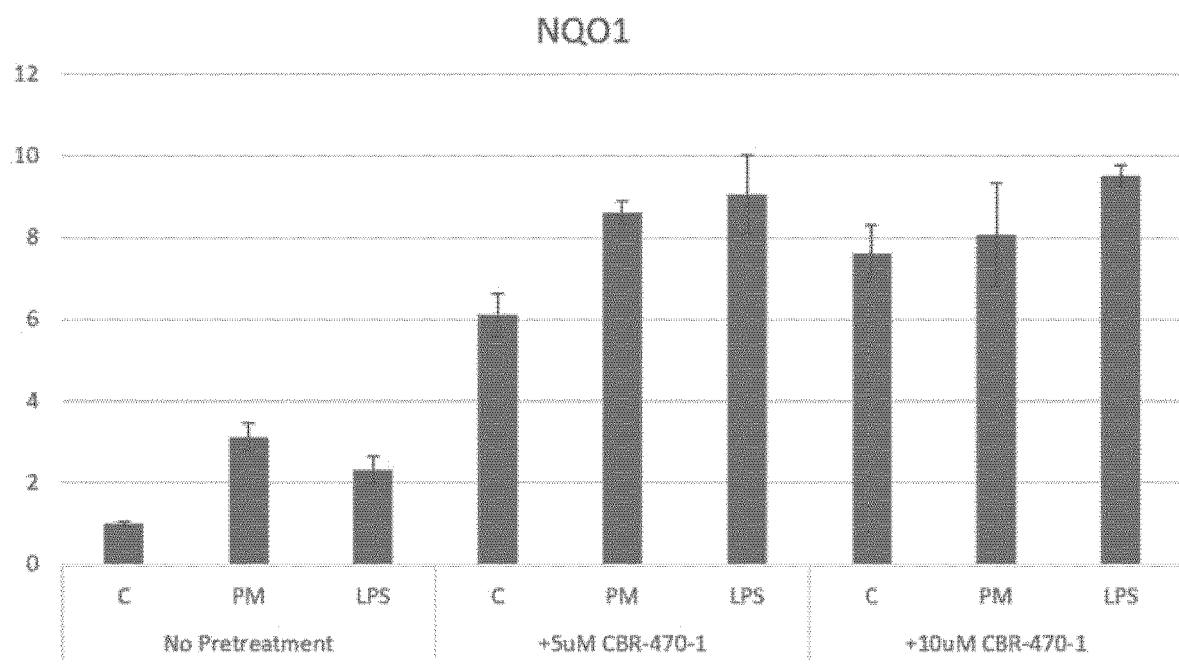
Figure 18A:
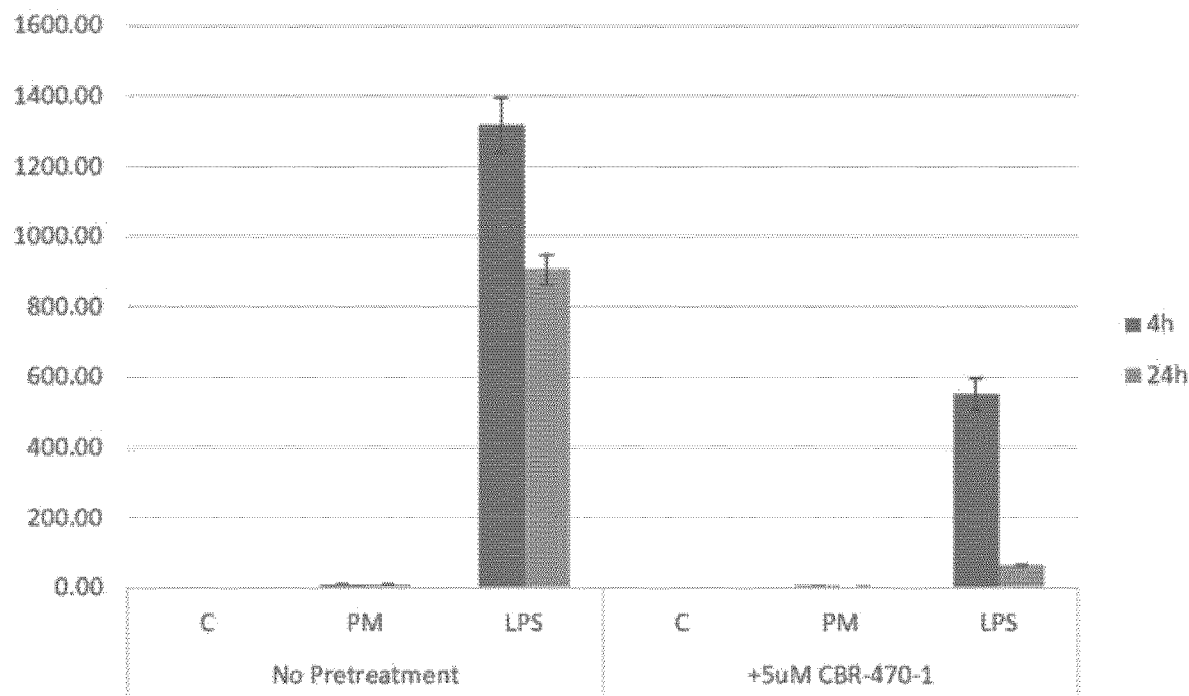
FIG. 18A-C. MHS cells were treated with particulate matter (PM) or LPS and vehicle control (media) in the absence or presence of CBR-470-1 (5 uM, pretreated 4 hours prior to PM/LPS) and measured IL-6, TNFa and NQO1 mRNA 4 hours and 24 hours later. CBR-470 pretreatment attenuated PM- and LPS-induced IL-6 and TNFa mRNA expression and induced NQO1 (Nrf2 target gene) under both PM and LPS in a dose dependent manner at both time points.
Figure 18B:
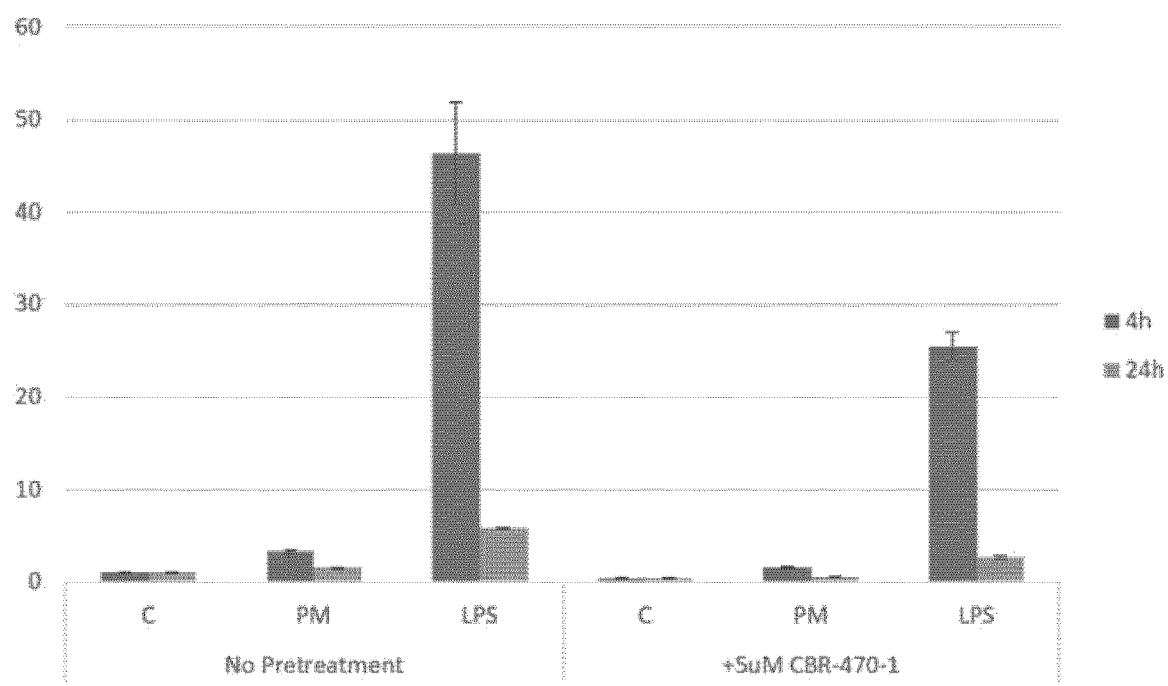
Figure 18C:
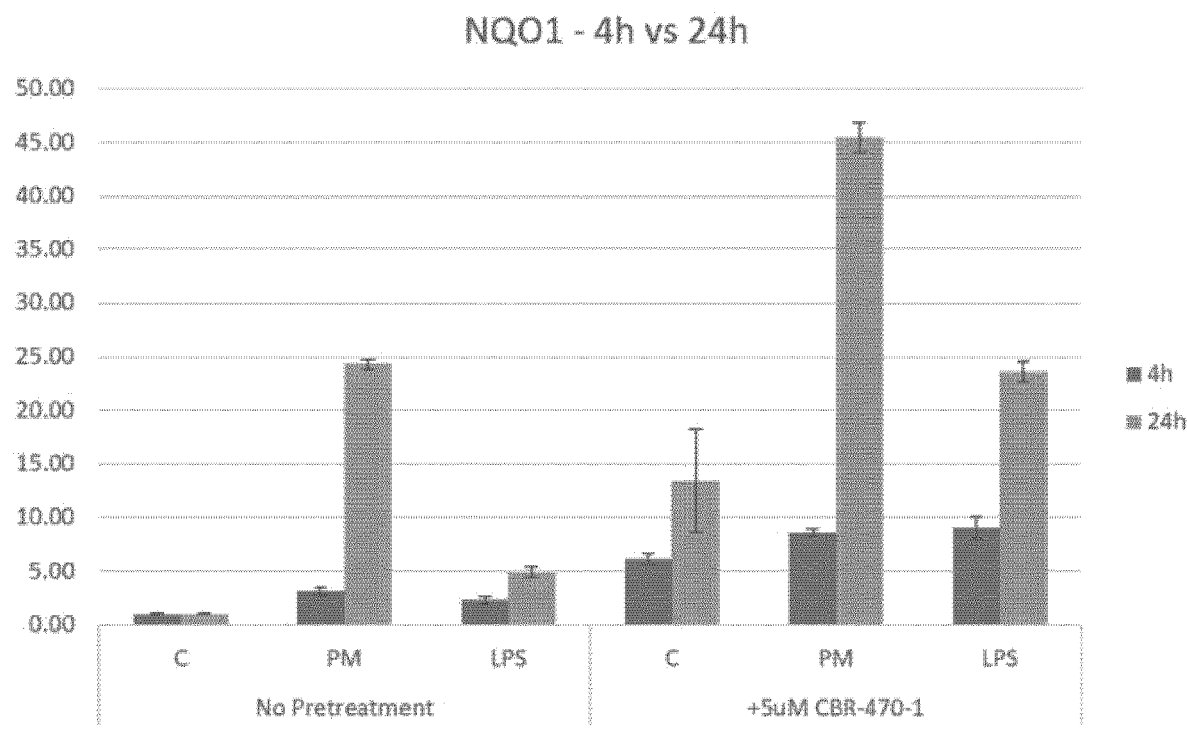
Figure 19A:
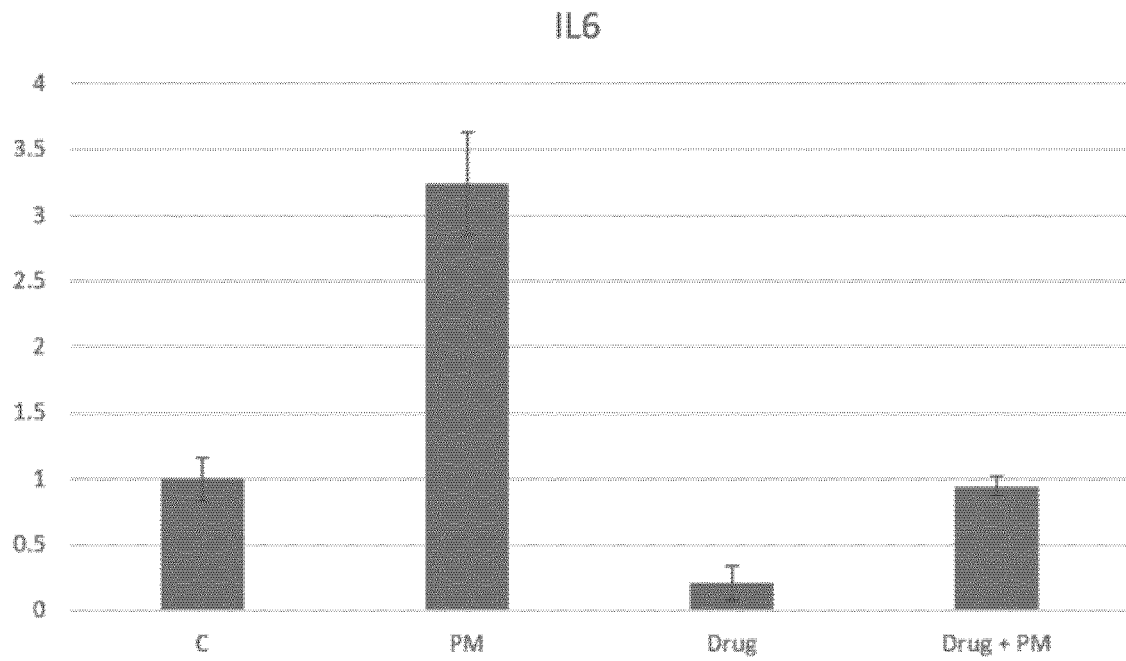
FIG. 19A-C. Primary murine alveolar macrophages were treated with PM or vehicle control (media) in the absence or presence of CBR-470-1 (pretreated 4 hours prior to PM) and measured IL-6, TNFa and NQO1 mRNA 4 hours later. CBR-470-1 pretreatment attenuated PM-induced 16 and TNFa mRNA expression and induced NQO1 (Nrf2 target gene).
Figure 19B:
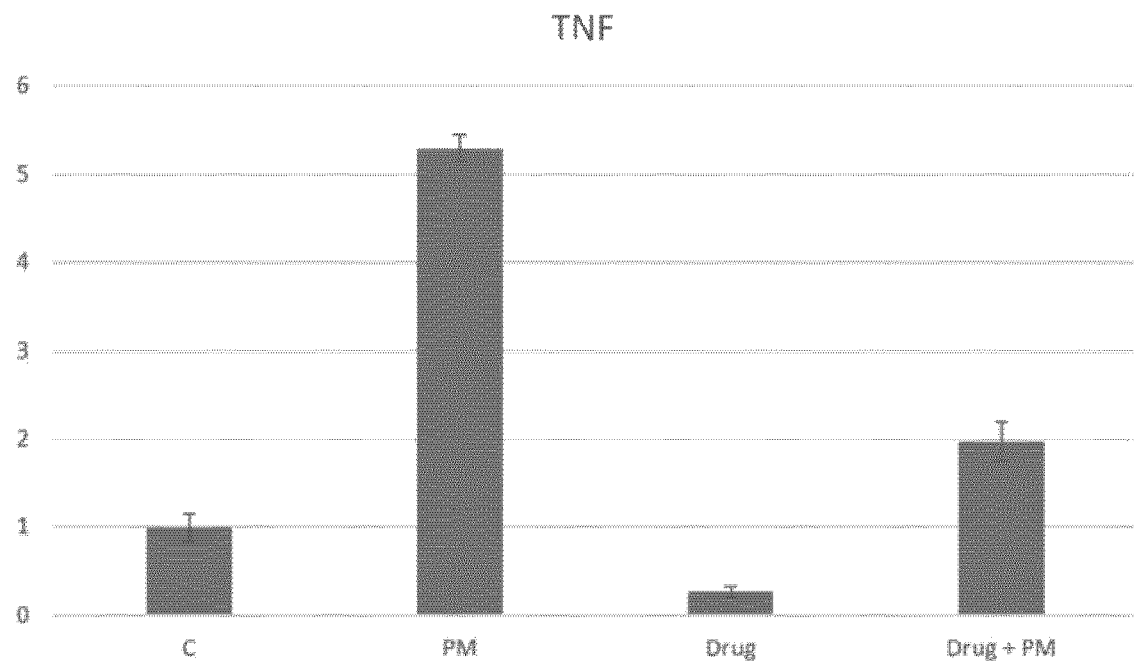
Figure 19C:
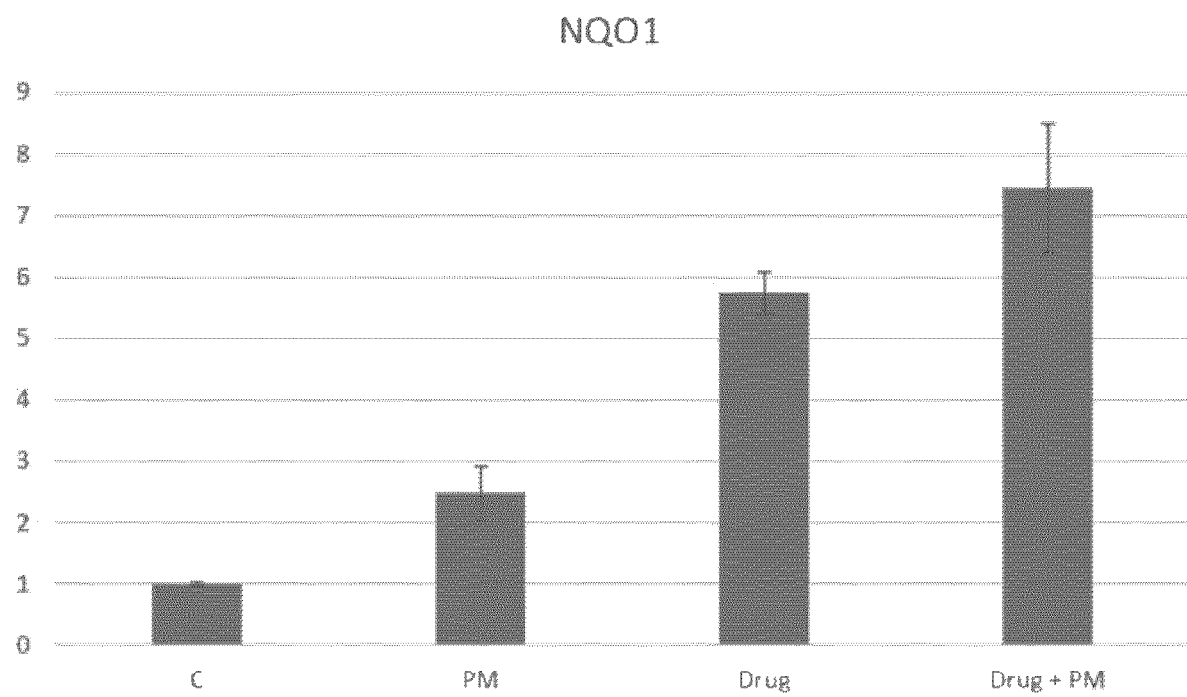
Figure 20:
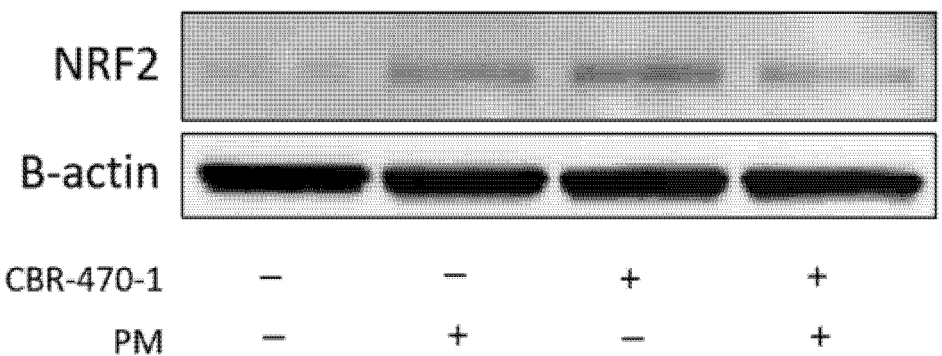
FIG. 20. MHS cells were treated with PM or vehicle control (media) in the absence or presence of CBR-470-1 (pretreated 4 hours prior to PM/LPS) and measured protein expression of NQO1 (Nrf2 target gene) at 4 hours.
Figure 21:
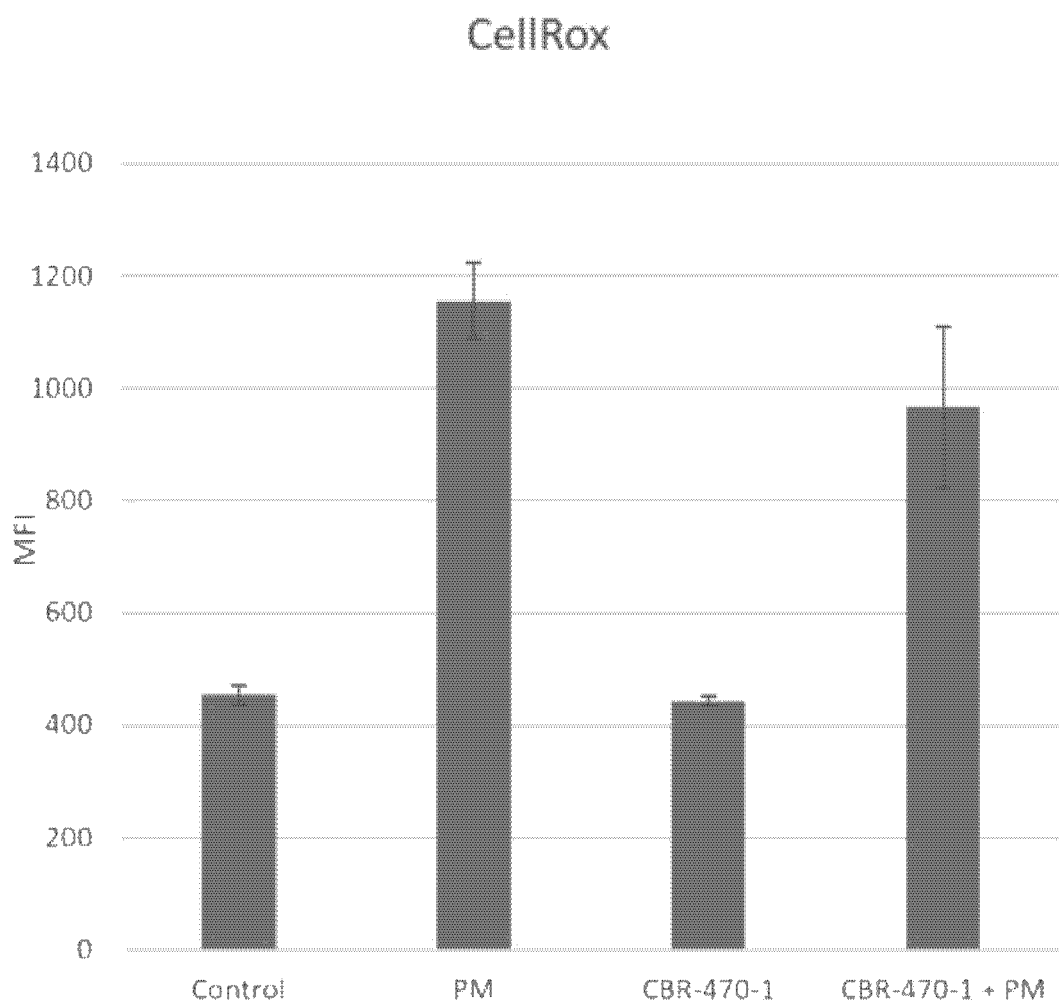
FIG. 21. ROS generation using CellRox in MHS cells treated with PM in the absence or presence of CBR-470-1 (pretreated 4 hours before PM). While PM induced ROS at 30 minutes, CBR-470 did not increase ROS in control cells or affect the PM-induced ROS generation. ROS levels expressed as mean fluorescent intensity.

In an effort to identify this modification, a model peptide containing cysteine and arginine separated by a glycine linker was synthesized, which was intended to mimic high inter- or intramolecular Cys/Arg proximity, and treated it with MGx at physiologic temperature and pH overnight (FIG. 3b). LC-MS analysis revealed a new peak, which corresponded to a mass increase of 36 Da, consistent with a mercaptomethylimidazole crosslink (FIG. 3c-d) formed by nucleophilic attack of the dicarbonyl by the side chains of cysteine and arginine, followed by dehydration-mediated cyclization and formation of a novel methylimidazole (MICA) posttranslational modification. The structure of the purified produced was confirmed by a series of one- and two-dimensional NMR experiments (FIG. 3d; FIG. 6d-g). To determine whether MICA modification occurs within KEAP1 protein, cells were treated with CBR-470-1 or MGx, isolated HMW-KEAP1 and monomeric KEAP1 by gel, and then digested these discrete populations for LC-MS/MS analyses. A peptide bearing a MICA crosslink between C151 and R135 was identified in isolated HMW-KEAP1 from both CBR-470-1 and MGx treatment, but not in the isolated monomeric KEAP1 (FIG. 3e). Furthermore, parallel-reaction monitoring (PRM) confirmed the presence and co-elution of more than a dozen parent-to-daughter ion transitions that were uniquely present in HMW-KEAP1 (FIG. 3f, FIG. 10a-b). These studies suggest a model where glycolytic metabolic status is coupled to NRF2-dependent gene expression through the direct interaction of a reactive glycolytic metabolite, MGx, and the sentinel protein KEAP1 via the formation of a stable and mechanistically novel protein PTM (FIG. 3g).

While it has been reported that MGx can form covalent modifications on diverse proteins, the compositions, sites and functions of these modifications have remained enigmatic. Likewise, several recent reports have implicated MGx in the pathogenesis of diseases such as diabetes[28] and aging[29], yet the discrete molecular targets of MGx in these contexts are unknown. Here it was found that inhibition of PGK1 increases triosephosphate levels, which results in elevated levels of cellular MGx and the formation of a HMW-KEAP1 species leading to NRF2-dependent gene expression. Formation of the HMW-KEAP1 species involves a novel PTM, MICA, that is dependent on MGx and serves to form a covalent linkage between proximal cysteine and arginine residues. These results raise intriguing questions about the general reactivity of MGx, its potential role as a signaling metabolite in other cellular processes, and the specific modifications involved in oft-cited advanced glycated end products as biomarkers of disease pathology. Both cellular and lysate treatment with MGx showed selective modification of C151 in KEAP1, likely due to the intrinsic hyperreactivity of this residue, and the presence of properly oriented arginine(s) that enables formation of the MICA modification. Additional factors such local metabolite concentration gradients may also contribute to MICA formation in KEAP1.

The direct connection between glucose metabolism and the KEAP1-NRF2 axis by MGx adds an additional layer of regulation to both pathways and global metabolic status. First, this connection highlights the role of glycolysis in regulating cellular redox status beyond the contribution to NADPH and glutathione production. These reducing equivalents are critical for the regulation of a wide range of reactive species in the cell, and when these levels are deregulated, the KEAP1-NRF2 pathway is poised to respond and limit cellular damage. Recent studies have also implicated the output of NRF2 transcriptional program in the direct detoxification of MGx through increased glutathione synthesis[30], GLO1 transcription, as well as redirection of glucose carbon away from central metabolites (e.g. MGx) and into the pentose phosphate pathway[31]. Therefore, the direct coupling of glucose metabolism with KEAP1 function through MGx creates an intrinsic feedback loop to sense and respond to changing metabolic demands in the cell. A final aspect of this study is the notion that modulation of endogenous reactive metabolite levels using small molecules may represent an alternative approach toward activating the ARE pathway for treatment of a number of diseases involving metabolic stress.

B. Methods

Chemicals. TBHQ, 2DG, MGx and GSH were obtained from Sigma Aldrich. The synthesis of AI-1 has been described previously[32]. The GLO1 inhibitor (CAS No. 174568-92-4) was from MedChemExpress. CBR-470-0 and CBR-581-9 were from ChemDiv. CBR-470-1 (initially from ChemDiv as D470-2172) and related analogs were synthesized in house according to full methods described in the Supplementary Information. All commercially obtained chemicals were dissolved in DMSO and used without further purification with the exception of 2DG, MGx and GSH, which were delivered as aqueous solutions.

Cell Culture. IMR32, SH-SY5Y, HeLa, and HEK293T cell lines were purchased from ATCC. Human lung fibroblasts (HLF) and mouse dermal fibroblasts (MDFs, C57BL/6-derived) were obtained from Sciencell and used before passage 3. IMR32, HLF, SH-SY5Y, HeLa, and HEK293T cells were propagated in DMEM (Corning) supplemented with 10% fetal bovine serum (FBS, Corning) and Anti-anti (Gibco). MDFs were propagated in fibroblast medium 2 from Sciencell. Mouse epidermal keratinocytes (MPEK-BL6) were obtained from Zen Bio and propagated in epidermal keratinocyte medium (Zen Bio).

High throughput screening and ARE-LUC reporter assay. For high throughput screening, IMR32 cells were plated at $5 \times 10^3$ cells per well in white 384-well plates in 40 µL of growth medium. The next day 100 ng of pTI-ARE-LUC reporter plasmid in 10 µL of Optimem medium (Gibco) was transfected into each well using Fugene HD at a dilution of 1 µg plasmid DNA: 4 µL of Fugene. 24 hours later, compounds were transferred using a 100 nL pintool head affixed to PerkinElmer FX instrument such that the final screening concentration was 2 µM. After 24 hour incubation, ARE-LUC luminance values were recorded on an Envision instrument after the addition of 30 µL of Bright Glo reagent solution (Promega, diluted 1:3 in water). Compounds which increased ARE-LUC signal greater than 4 Z-scores from plate mean were deemed hits. For overexpression and knockdown experiments in HEK293T with ARE-LUC reporter readouts, $5 \times 10^5$ cells were plated on poly-d-lysine coated plates and transfected with 1.5 µg of overexpression or shRNA plasmid and 500 ng of pTI-ARE-LUC using Optimem medium and Fugene in the same mode as above. 24 hours later, $10^3$ transfected cells were plated in 50 µL of growth medium in white 96-well plates. After a 24 hour incubation, an additional 50 µL of growth medium with compound at the indicated concentrated was added to each well. ARE-LUC luminance values were recorded on an Envision plate reader 24 hours later by the addition of 75 μL of Bright Glo reagent solution (1:3 in water).

Peroxide stress model. 104 SH-SY5Y cells were plated in 100 μL of growth medium in white 96-well plates. After 48 hours of compound treatment, 20 μL of tert-butyl peroxide diluted to the indicated concentrations was added to each well. After an 8 hour incubation, cell viability measurements were recorded on an Envision plate reader after the addition of 50 μL of a Cell Titer Glo solution (Promega, diluted 1:6 in water). Relative viabilities are reported as a fraction relative to the same dose of compound treatment without TBHP.

shRNA knockdown studies. PGK1-targeting shRNA vectors sh10 and sh47 refer to Sigma Mission shRNA lentiviral clones NM_000291.2-338s1c1 and NM_000291.2-935s1c1 respectively. GLO1-targeting shRNA vectors sh29 and sh30 refer to Sigma Mission shRNA lentiviral clones NM_006708.1-195s1c1 and NM_006708.1-292s1c1 respectively. The non-targeting scrambled control vector refers to SHC002 (Sigma). Lentiviruses were generated in HEK293T cells by transient expression of the above vectors with pSPAX2 and pMD2.G packaging vectors (Addgene plasmids 11260 and 12259). Viral supernatants were collected after 48 hours of expression and passed through a 70 μm syringe filter before exposure to target cells.

Quantitative RT-PCR. Cells were collected by trypsinization and subsequent centrifugation at 500 g. RNA was isolated using RNeasy kits from Qiagen and concentrations obtained using a NanoDrop instrument. 500 ng-5 μg of RNA was then reverse transcribed with oligo dT DNA primers using a SuperScript III First-Strand Synthesis kit from Invitrogen. Quantitative RT-PCR reactions were measured on a Viia 7 Real-Time PCR system (Thermo) using a Clontech SYBR green-based master mix. Gene specific primer sets are provided in Table 1a and 1b. Reactions were normalized to TUBG1 levels for each biological replicate and relative transcript abundance calculated using the comparative $C_t$ method.

TABLE 1a

| Gene | Forward Primer Sequence | Reverse Primer Sequence |
|---|---|---|
| NQO1 | GCCTCCTTCATGGCATAGTT | GGACTGCACCAGAGCCAT |
| HMOX1 | GAGTGTAAGGACCCATCGGA | GCCAGCAACAAAGTGCAAG |
| ME1 | GGAGACGAAATGCATTCACA | ACGAATTCATGGAGGCAGTT |
| GCLM | GCTTCTTGGAAACTTGCTTCA | CTGTGTGATGCCACCAGATT |
| TX-NRD1 | TCAGGGCCGTTCATTTTTAG | GATCTGCCCGTTGTGTTTG |
| FTH1 | GGCAAAGTTCTTCAAAGCCA | CATCAACCGCCAGATCAAC |
| GSR | TTGGAAAGCCATAATCAGCA | CAAGCTGGGTGGCACTTG |
| EPHX1 | CTTCACGTGGATGAAGTGGA | CTGGCGGAATGAATTTGACT |
| ABCC2 | GGGATCTCTTCCACACTGGAT | CATACAGGCCCTGAAGAGGA |
| PRDX1 | GGGCACACAAAGGTGAAGTC | GCTGTTATGCCAGATGGTCAG |
| NQO2 | TGCGTAGTCTCTCTTCAGCG | GCAACTCCTAGAGCGGTCCT |
| GSTM3 | GGGTGATCTTGTTCTTCCCA | GGGGAAGCTCCTGACTATGA |

TABLE 1a-continued

| Gene | Forward Primer Sequence | Reverse Primer Sequence |
|---|---|---|
| SOD1 | CCACACCTTCACTGGTCCAT | CTAGCGAGTTATGGCGACG |
| TX-NRD1 | TCAGGGCCGTTCATTTTTAG | GATCTGCCCGTTGTGTTTG |
| GSTP1 | CTCAAAAGGCTTCAGTTGCC | ACCTCCGCTGCAAATACATC |
| GCLC | CTTTCTCCCCAGACAGGACC | CAAGGACGTTCTCAAGTGGG |
| GLO1 | TGGATTAGCGTCATTCCAAG | GCGGACCCCAGTACCAAG |
| PGK1 | CTTGGGACAGCAGCCTTAAT | CAAGCTGGACGTTAAAGGGA |
| TUBG1 | ATCTGCCTCCCGGTCTATG | TACCTGTCGGAACATGGAGG |

TABLE 1b

| Mutation | Primer (Forward) | Primer (Reverse) |
|---|---|---|
| C23S | 5'-/5Phos/ TGA ACG GTG CTG TCA TGT ACC AGA TC-3' | 5'-/5Phos/ CCC CTC AGG AGA CTG TGA CTG CAG GGG C-3' |
| C38S | 5'-/5Phos/GCC CTC CCA GCA TGG CAA 3' | 5'-/5Phos/ GTC ACC TCC GCC TTG GAC TCA GT-3' |
| C151S | 5'-/5Phos/ TGA ACG GTG CTG TCA TGT ACC AGA TC-3' | 5'-/5Phos/ TGA CGT GGA GGA CAG ACT TC TCGC-3' |
| C273S | 5'-/5Phos/ CCG A AC TTC CTG CAG CT-3' | 5'-/5Phos/ CGT CAA CGA GTG GGA GCG CAC G-3' |
| C288S | 5'-/5Phos/ GTC CGA CTC CCG CTG CAA GGA CT-3' | 5-/5Phos/ TGC AGG ATC TCG GAC TTC TGC AGCT T-3' |
| C396S | 5'-/5Phos/ GAC CAA TCA GTG GTC GCC CTG-3' | 5-/5Phos/ ATG GGG TTG TAA GAG TCC AGG GC-3' |
| C405S | 5-/5Phos/ CGT GCC CCG TAA CCG CAT CG-3' | 5'-/5Phos/ CTC ATG GGG GCG CTG GCG G-3' |
| K39R | 5'-/5Phos/ GCC CTC CCA GCA TGG CAA-3' | 5'-/5Phos/ GTC ACC TCC GCC CTG CAC TCA GT-3' |
| K39M | 5'-/5Phos/ GCC CTC CCA GCA TGG CAA-3' | 5'-GTC ACC TCC GCC ATG CAC TCA GT-3' |
| C38S/K39M | 5'-/5Phos/ GCC CTC CCA GCA TGG CAA-3' | 5-GTC ACC TCC GCC ATG GAC TCA GT-3' |
| K150M | 5'-/5Phos/ TGA ACG GTG | 5'-TGA CGT GGA GGA CAC ACA |

TABLE 1b-continued

| Mutation | Primer (Forward) | Primer (Reverse) |
|---|---|---|
|  | CTG TCA TGT ACC AGA TC-3' | TCT CGC C-3' |
| R6A | 5'-GCA GCC AGA TCC CGC GCC TAG CGG GGC TG-3' | 5'-CAG CCC CGC TAG GCG CGG GAT CTG GCTGC-3' |
| R15A | 5'-GGG CCT GCT GCG CAT TCC TGC CCC TGC A-3' | 5'-TGC AGG GGC AGG AAT GCG CAG CAG GCCC-3' |
| R50A | 5'-CTC CCA GCA TGG CAA CGC CAC CTT CAG CTA CAC-3' | 5'-GTG TAG CTG AAG GTG GCG TTG CCA TGC TGG GAG-3' |
| R135A | CCC AAG GTC ATG GAG GCC CTC ATT GAA TTC GCC T-3' | 5'-AGG CGA ATT CAA TGA GGG CCT CCA TGA CCT TGG G-3' |

Gene set enrichment analyses (GSEA). Total RNA was extracted from IMR32 cells treated for 24 hours with either DMSO or 5 µM CBR-470-1 (3 biological replicates per condition) using a RNeasy kit (Qiagen). RNA-seq experiments were performed by the Scripps Next Generation Sequencing Core according to established in house methods. Gene set enrichment analyses and leading edge heatmaps were generated with TPM values from the above experiment using the java GSEA package. "NFE2L2 targets" gene set refers to Molecular Signature Database (http://software-.broadinstitute.org/gsea/msigdb) gene set ID M2662.

Quantitative Metabolomic Profiling. For polar metabolite profiling experiments, cells were grown in 15 cm plates and cultured in RPMI supplemented with 10% FBS, 2 mM L-glutamine and 1% P/S prior to media replacement containing either vehicle (DMSO) or the indicated dose of CBR-470-1. Following incubation for the appropriate time, cells were scraped into ice-cold PBS and isolated by centrifugation at 1,400 g at 4° C. Cell pellets were resuspended in 300 µl of an 80:20 mixture of cold MeOH/H2O, an internal standard was added (10 nmol d3-serine; Sigma Aldrich), and the suspension was sonicated (Fisher Scientific FB-505) for 5 seconds followed by a 10 minute centrifugation at 16,000 g. The supernatant was collected, dried under $N_2$ gas and resulting dried metabolites resuspended in 30 µl of 40% MeOH/H2O for analysis on an Agilent triple quadrupole LC-MS/MS (Agilent Technologies 6460 QQQ). For negative mode operation, metabolites were separated by hydrophilic interaction chromatography with a Luna-$NH_2$ column (Phenomenex) running mobile phase A ($CH_3CN$ supplemented with 0.2% $NH_4OH$) and B (95:5 v/v $H_2O$: $CH_3CN$ supplemented with 50 mM $NH_4OAc$ and 0.2% $NH_4OH$) and the following gradient: 0% B for 3 min; linear increase to 100% B for 27 min at a flow rate of 0.4 ml/min, followed by an isocratic flow of 100% B for 3 min. The spectrometer settings were: capillary voltage=4.0 kV, drying gas temperature=350° C. at 10 L/min, and the nebulizer pressure was 45 psi. Metabolite peak transitions and retention times are listed in Table 2 and were confirmed by running standards for measured glycolytic, PPP, CAC and co-factor metabolites. 2-phosphoglycerate and 3-phosphoglycerate isomers were quantified in aggregate (2PG/3PG). Relative metabolite abundance was quantified by integrated peak area for the given MRM-transition, and all metabolite levels were normalized to internal standard extracted ion intensity values for $d_3$-serine. These parameters were used to quantify all metabolites, with the exception of 1,3-BPG and MGx, which required chemical derivitization to stable intermediates prior to LC-MS/MS quantification, as previously reported[20,33]. MGx deviated from all other metabolites, as it was separated on a Gemini reverse-phase C18 column (5 mm, 4.6 mm×50 mm; Phenomenex) together with a pre-column (C18, 3.5 mm, 2 mm×20 mm) and detected in positive mode analysis, with mobile phase A ($H_2O$) and B (50:50 v/v $H_2O$:$CH_3CN$) supplemented with 0.1% TFA. The gradient started with 0% B for 2 min and increased linearly to 100% B over 10 min with a flow rate of 0.4 ml/min, followed by an isocratic gradient of 100% B for 5 min at 0.4 ml/min. The QQQ settings were the same as above.

TABLE 2

| Metabolite | Precursor mass | MS1 Resolution | MS2 Production | MS2 Resolution | Dwell | Fragmentor | Collision Energy | Polarity | Retention time (min) |
|---|---|---|---|---|---|---|---|---|---|
| Glucose | 179.05 | Wide | 89.2 | Unit | 5 | 68 | 12 | Neg | 12.2 |
| G6P | 258.9 | Wide | 138.9 | Unit | 100 | 100 | 5 | Neg | 22.3 |
| FBP | 339.1 | Wide | 96.9 | Unit | 100 | 100 | 20 | Neg | 26.8 |
| GAP | 169 | Wide | 96.9 | Unit | 100 | 100 | 5 | Neg | 22.1 |
| BPG | 264.9 | Wide | 96.9 | Unit | 5 | 86 | 21 | Neg | 30.9 |
| 2/3.PG | 184.98 | Wide | 78.9 | Unit | 5 | 86 | 21 | Neg | 24.6 |
| PEP | 166.97 | Wide | 79 | Unit | 5 | 78 | 9 | Neg | 25.4 |
| Pyruvate | 87.1 | Wide | 43 | Unit | 100 | 100 | 10 | Neg | 14.8 |
| Lac | 89.1 | Wide | 43 | Unit | 100 | 100 | 20 | Neg | 13.5 |
| D3-Serine | 107.05 | Wide | 75.1 | Unit | 5 | 18 | 9 | Neg | 13.9 |
| R5P | 228.7 | Wide | 78.8 | Unit | 100 | 100 | 35 | Neg | 19.9 |
| Serine | 104.2 | Wide | 73.8 | Unit | 5 | 100 | 5 | Neg | 13.9 |
| GSH | 305.7 | Wide | 143.0 | Unit | 100 | 100 | 15 | Neg | 16.7 |
| GSSG | 610.7 | Wide | 305.9 | Unit | 100 | 100 | 15 | Neg | 20.5 |
| Succ | 117 | Wide | 73.1 | Unit | 100 | 100 | 5 | Neg | 18.8 |
| Glu | 146.1 | Wide | 102.1 | Unit | 100 | 100 | 5 | Neg | 15.9 |
| Cit | 191 | Wide | 111 | Unit | 5 | 100 | 5 | Neg | 24.4 |
| NAD* | 662.1 | Wide | 540 | Unit | 100 | 100 | 15 | Neg | 16.1 |
| NADH | 743.5 | Wide | 407.9 | Unit | 100 | 100 | 35 | Neg | 16.1 |
| NADP* | 742 | Wide | 619.9 | Unit | 100 | 100 | 25 | Neg | 24.1 |
| NADPH | 743.5 | Wide | 407.8 | Unit | 100 | 100 | 25 | Neg | 24.1 |
| ATP | 506 | Wide | 159 | Unit | 100 | 100 | 25 | Neg | 27.5 |
| ADP | 425.8 | Wide | 134 | Unit | 100 | 100 | 15 | Neg | 26.5 |

TABLE 2-continued

| Metabolite | Precursor mass | MS1 Resolution | MS2 Production | MS2 Resolution | Dwell | Fragmentor | Collision Energy | Polarity | Retention time (min) |
|---|---|---|---|---|---|---|---|---|---|
| 3PGha | 199.98 | Wide | 199.98 | Unit | 5 | 116 | 0 | Neg | 22.4 |
| 3PGha | 199.98 | Wide | 79 | Unit | 5 | 116 | 15 | Neg | 22.4 |
| 2MQ | 145.1 | Wide | 77.1 | Unit | 5 | 100 | 24 | Pos | 8.5 |
| 2MQ | 145.1 | Wide | 92.1 | Unit | 5 | 100 | 20 | Pos | 8.5 |
| D3-Serine | 109.07 | Wide | 63.1 | Unit | 5 | 40 | 12 | Pos | 4.3 |

FLAG-tagged Protein Expression and Western Blotting. Full-length, human PGK1 (NM_000291, Origene) transiently expressed from a pCMV6 entry vector with a C-terminal Myc-DDK tag; full-length, human KEAP1 (28023, Addgene) was transiently expressed from a pcDNA/FRT/TO plasmid with a C-terminal 3×FLAG tag. All references to FLAG-PGK1 or FLAG-KEAP1 represent the proteins in the aforementioned vectors, respectively. Transient protein expression was performed in confluent 10 cm plates of HEK293T cells by transfection of 1 µg plasmid with Lipofectamine 2000 (Invitrogen) according to manufacturer's protocol. For in situ compound or metabolite treatment experiments, compounds were added approximately 24 hours after transfection, and incubated for the indicated duration. For FLAG-KEAP1 western blotting and immunoprecipitation experiments, cells were harvested by scraping, pelleted by centrifugation, washed twice with PBS and lysed in 8 M urea, 50 mM NH4HCO3, phosphatase inhibitor cocktail (Sigma Aldrich), and EDTA-free complete protease inhibitor (Roche), pH 8.0, at 4° C. Lysate was sonicated (Fisher Scientific FB-505), insoluble debris cleared by centrifugation, and the supernatant was diluted into 4× Laemmli buffer containing 50 mM dithiothreitol (DTT) as a reducing agent. Samples were prepared for SDS-PAGE by heating to 95° C. for 5 minutes, cooled to room temperature, resolved on NuPAGE Novex 4-12% Bis-Tris Protein Gels (Invitrogen), and transferred onto nitrocellulose membranes by standard western blotting methods. Membranes were blocked in 2% BSA in TBS containing 0.1% tween-20 (TBST) and probed with primary and secondary antibodies. Primary antibodies used in this study include: anti-FLAG-M2 (1:1000, F1804, Sigma Aldrich), anti-KEAP1 (1:500, SC-15246, Santa Cruz), anti-HSPA1A (1:1000, 4872, Cell Signaling), anti-ACTB (1:1000, 4790, Cell Signaling), anti-GAPDH (1:1000, 2118S, Cell Signaling) and TUBG (1:1000, 5886, Cell Signaling). Rabbit polyclonal anti-pgK antibody was generated using pgK-modified KLH and affinity purification as described[4] at a 1:400 dilution of a 0.33 mg/mL stock in 10 mM sodium HEPES (pH 7.5), 150 mM NaCl, 30% glycerol and 0.02% sodium azide. Secondary donkey anti-rabbit, donkey anti-goat, and donkey anti-mouse (Licor), were used at 1:10,000 dilution in 2% BSA-containing TBST and incubated for 1 hour prior to washing and imaging on a Licor infrared scanner. Densitometry measurements were performed with ImageJ software.

Time- and dose-dependent CBR-470-1 treatment studies were performed in HEK293T cells 24 hours after transient transfection of FLAG-KEAP1, or in IMR32 cells for endogenous KEAP1. Fresh RPMI media with 10% FBS, 2 mM L-glutamine, 1% P/S and the indicated concentration of CBR470-1 (20 µM for time-dependent experiments) or equivalent DMSO was added to cells in 10 cm dishes. Following the indicated incubation time cells were lysed in lysis buffer [50 mM Tris, 150 mM NaCl, 1% Triton-X 100, phosphatase inhibitor cocktail (Sigma Aldrich), and EDTA-free complete protease inhibitor (Roche), pH 7.4] and processed for western blot as indicated above.

Target identification studies with CBR-470-PAP. 10 cm dishes of confluent IMR32 cells were exposed to 5 µM CBR-470-PAP with the addition of either DMSO or a 50-fold molar excess of CBR-470-1 (250 µM) for 1 hour at 37° C. Samples were then UV crosslinked using a Stratalinker 2400 instrument for 10 minutes. RIPA extracted lysates were then fractionated with ammonium sulfate with percent increments of 20. These fractions were then separated via SDS-PAGE and relevant probe-labeling was determined by anti-biotin (1:500, ab1227, Abcam) western blotting as above. A parallel gel was silver stained using the Pierce silver stain kit. Relevant gel slices from the 80 percent fraction were excised and PGK1 identity was determined by LC-MS/MS by the Scripps Center for Metabolomics and Mass Spectrometry. Follow up shRNA knock down studies confirmed PGK1 as the target within this fraction.

Dye-based thermal denaturation assay. Thermal denaturation experiments were performed using a Protein Thermal Shift Dye Kit (ThermoFisher, 4461146). Reactions contained 2 µM recombinant PGK1 with the indicated dose of aqueously-delivered CBR-470-1 with 1× supplied thermal shift dye and reaction buffer in 20 uL reaction volumes. Fluorescence values were recorded using a Viia7 Real-Time PCR instrument according to supplied instructions.

Recombinant PGK1 assay. PGK1 enzymatic activity in the forward direction was measured with a coupled enzymatic assay[34]. Three PGK1 conditions were prepared by dissolving recombinant PGK1 in potassium phosphate buffer (10 mM $KH_2PO_4$, 10 mM $MgSO_4$, pH 7.0), and transferring the aliquots of PGK1 solution to the microtubes being treated with same amount of DMSO and indicated concentrations of CBR-470-1. Final concentration of PGK1 is 20 ng/mL and DMSO is 1% for each sample. Two blank conditions, 0 µM and 100 µM of CBR-470-1 with no PGK1, were also prepared for the control measurements. All PGK1 samples and blank samples were pre-incubated for 20 minutes and then transferred to the UV-transparent 96 well plate (Corning). The assay solution (10 mM $KH_2PO_4$, 2 mM G3P, 0.6 mM $NAD^+$, 200 mM Glycine, 0.4 mM ADP, pH 7.0) was activated by adding GAPDH with 10 µg/mL final concentration, and then the assay solution was added to the wells containing PGK1 samples and blank samples. The change in absorbance at 340 nm at room temperature was measured every 20 seconds for 45 minutes, by Tecan Infinite M200 plate reader. Each condition was performed with three independent replications.

Isothermal dose response profiling of PGK1. In-vitro thermal profiling assay for recombinant proteins was performed by dissolving pure recombinant PGK1 and GAPDH into PBS and dividing equal amount of mixture into 9 aliquots. Each aliquot was transferred to 0.2 mL PCR microtubes being treated with different amounts of CBR-470-1 added from DMSO stock, and equal amount of DMSO for the control. Each microtube contains 50 μL of mixture with final concentration of 45 μg/mL for each protein and DMSO concentration 1% with following final concentrations of CBR-470-1; 0 μM, 0.1 μM, 0.3 μM, 1 μM, 3 μM, 10 μM, 33 μM, 100 μM, 333 μM. After 30 minutes incubation at 25° C., samples were heated at 57° C. for 3 minutes followed by cooling at 25° C. for 3 minutes using Thermal Cycler. The heated samples were centrifuged at 17,000 g for 20 minutes at 4° C., and the supernatants were transferred to new Eppendorf tubes. Control experiments were performed with heating at 25° C. for 3 minutes, instead of 57° C. Samples were analyzed by SDS-PAGE and Western blot.

Metabolite Treatments and HMW-KEAP1 screening. For in vitro screening of glycolytic metabolites, HEK293T cells expressing FLAG-KEAP1 were lysed by snap-freeze-thaw cycles (3×) in PBS, pH 7.4, containing EDTA-free complete protease inhibitor (Roche). Lysates were cleared by centrifugation and the supernatants normalized for concentration by Bradford reagent (2 mg/mL). Concentrated stocks of each metabolite were made in PBS, which were added to the lysate samples for the final indicated concentrations and incubated at 37° C. for 2.5 hours with shaking. Following incubation, samples were denatured with 6 M urea and processed for SDS-PAGE and western blotting. Methylglyoxal (40% v/v with $H_2O$), glyceraldehyde 3-phosphate (GAP), dihydroxyacetone phosphate (DHAP), and 2,3-bisphosphoglycerate (2,3-BPG) were all obtained from Sigma Aldrich and used as PBS stocks. In situ metabolite treatments were performed in HEK293T cells 24 hours after transfection of FLAG-KEAP1, treated with MGx (1 or 5 mM) in $H_2O$ (Sigma) or equivalent vehicle alone for 8 hours. Cells were collected by scraping, washed in PBS and centrifuged, and lysed in urea lysis buffer and analysis by SDS-PAGE and western blot. Dose-response experiments were performed with high purity MGx was prepared by acidic hydrolysis of MG-1,1-dimethylacetal (Sigma Aldrich) followed by fractional distillation under reduced pressure and colorimetric calibration of the distillates, as previously reported[33]. For in vitro MGx dose-response dimerization of KEAP1, HEK293T cells expressing FLAG-KEAP1 were lysed in PBS as indicated above, then serial dilutions of high purity MGx in 50 mM Sodium Phosphate, pH 7.4, were added to the equal volume of lysate aliquots with final protein concentration of 1 mg/mL. Each mixture was incubated at 37° C. for 8 hours with rotating, HMW-KEAP1 formation was analyzed by SDS-PAGE and western blot.

For studies with recombinant KEAP1, FLAG-KEAP1 was expressed in HEK293T cells from transient transfection of the Flag-Keap1 plasmid (Addgene plasmid #28023). FLAG-KEAP1 protein was immunopurified after overnight incubation at 4 degrees with anti-FLAG M2 magnetic beads (Sigma) in RIPA buffer in the presence of protease inhibitors, eluted with 3×FLAG peptide (150 ng/mL) in PBS, and desalted completely into PBS. 500 ng of purified FLAG-KEAP1 protein was then subjected to reducing conditions with the addition of either TCEP (0.1 mM) or DTT (1 mM) for 10 minutes at 37 degrees. MGx was then added to a final concentration of 5 mM and incubated for 2 hours at 37 degrees. Reactions were quenched by the addition of 50 μL of 4× sample buffer and subsequent boiling for 10 minutes. 12 μL of this reaction was then separated by SDS-PAGE and the presence of HMW-KEAP1 evaluated by anti-FLAG Western blotting as described or by silver staining using the Pierce Silver Stain Kit (ThermoFisher Scientific).

Site-directed Mutagenesis of KEAP1. KEAP1 mutants were generated with PCR primers in Table 1 according to the Phusion site-directed mutagenesis kit protocol (F-541, Thermo Scientific) and the QuikChange site-directed mutagenesis kit protocol (200523, Agilent). Mutant KEAP1 plasmids were verified by sequencing [CMV (forward), wild-type primers in the middle of KEAP1 sequence (forward) and BGH (reverse)], and were transiently expressed in HEK293T cells in the same manner as wild type KEAP1. Screening of CBR-470-1-induced HMW-KEAP1 formation with mutant constructs was performed just as with wild type KEAP1, after 8 hour CBR-470-1 treatment (20 μM). Following treatment, cells were harvested and prepared for SDS-PAGE and western blotting as indicated above.

SILAC cell culture methods and proteomic sample preparation. SILAC labeling was performed by growing cells for at least five passages in lysine- and arginine-free SILAC medium (RPMI, Invitrogen) supplemented with 10% dialyzed fetal calf serum, 2 mM L-glutamine and 1% P/S. "Light" and "heavy" media were supplemented with natural lysine and arginine (0.1 mg/mL), and $^{13}C$-, $^{15}N$-labeled lysine and arginine (0.1 mg/mL), respectively.

General protein digestion for LC-MS/MS analysis was performed by dissolving protein (e.g. whole lysate or enriched proteins) in digestion buffer (8 M urea, 50 mM $NH_4HCO_3$, pH 8.0), followed by disulfide reduction with DTT (10 mM, 40 minutes, 50° C.), alkylation (iodoacetamide, 15 mM, 30 min, room temperature, protected from light) and quenching (DTT, 5 mM, 10 minutes, room temperature). The proteome solution was diluted 4-fold with ammonium bicarbonate solution (50 mM, pH 8.0), CaCl2) added (1 mM) and digested with sequencing grade trypsin (~1:100 enzyme/protein ratio; Promega) at 37° C. while rotating overnight. Peptide digestion reactions were stopped by acidification to pH 2-3 with 1% formic acid, and peptides were then desalted on ZipTip C18 tips (100 μL, Millipore), dried under vacuum, resuspended with LC-MS grade water (Sigma Aldrich), and then lyophilized. Lyophilized peptides were dissolved in LC-MS/MS Buffer A ($H_2O$ with 0.1% formic acid, LC-MS grade, Sigma Aldrich) for proteomic analysis.

Proteomic LC-MS/MS and Data Analysis. LC-MS/MS experiments were performed with an Easy-nLC 1000 ultra-high pressure LC system (ThermoFisher) using a PepMap RSLC C18 column heated to 40° C. (column: 75 μm×15 cm; 3 μm, 100 Å) coupled to a Q Exactive HF orbitrap and Easy-Spray nanosource (ThermoFisher). Digested peptides (500 ng) in MS/MS Buffer A were injected onto the column and separated using the following gradient of buffer B (0.1% Formic acid acetonitrile) at 300 nL/min: 0-2% buffer B over 10 minutes, 2-40% buffer B over 120 minutes, 40-70% buffer B over 10 minutes, and 70-100% buffer B over 5 minutes. MS/MS spectra were collected from 0 to 150 minutes using a data-dependent, top-20 ion setting with the following settings: full MS scans were acquired at a resolution of 120,000, scan range of 400-1600 m/z, maximum IT of 50 ms, AGC target of 1e6, and data collection in profile mode. MS2 scans was performed by HCD fragmentation with a resolution of 15,000, AGC target of 1e5, maximum IT of 30 ms, NCE of 26, and data type in centroid mode. Isolation window for precursor ions was set to 1.5 m/z with an underfill ratio of 0.5%. Peptides with charge state >5, 1 and undefined were excluded and dynamic exclusion was set to eight seconds. Furthermore, S-lens RF level was set to 60 with a spray voltage value of 2.60 kV and ionization chamber temperature of 300° C. MS2 files were generated and searched using the ProLuCID algorithm in the Integrated Proteomics Pipeline (IP2) software platform. Human proteome data were searched using a concatenated target/decoy UniProt database (UniProt_Human_reviewed_04-10-2017.fasta). Basic searches were performed with the following search parameters: HCD fragmentation method; monoisotopic precursor ions; high resolution mode (3 isotopic peaks); precursor mass range 600-6,000 and initial fragment tolerance at 600 p.p.m.; enzyme cleavage specificity at C-terminal lysine and arginine residues with 3 missed cleavage sites permitted; static modification of +57.02146 on cysteine (carboxyamidomethylation); two total differential modification sites per peptide, including oxidized methionine (+15.9949); primary scoring type by XCorr and secondary by Zscore; minimum peptide length of six residues with a candidate peptide threshold of 500. A minimum of one peptide per protein and half-tryptic peptide specificity were required. Starting statistics were performed with a Δmass cutoff=15 p.p.m. with modstat, and trypstat settings. False-discovery rates of peptide (sfp) were set to 1%, peptide modification requirement (−m) was set to 1, and spectra display mode (−t) was set to 1. SILAC searchers were performed as above with "light" and "heavy" database searches of MS1 and MS2 files by including static modification of +8.014168 for lysine and +10.0083 for arginine in a parallel heavy search. SILAC quantification was performed using the QuantCompare algorithm, with a mass tolerance of 10 p.p.m. or less in cases where co-eluting peptide interfere. In general all quantified peptides has mass error within 3 p.p.m.

Quantitative Proteomic Detection of Potential KEAP1 Modification Sites. Quantitative surface mapping with SILAC quantitative proteomics was performed with "heavy" and "light" labeled HEK293T cells expressing FLAG-KEAP1. Cells were incubated with DMSO alone (light cells) or CBR-470-1 (20 μM, heavy cells) for 8 hours. After incubation cells were scraped, washed with PBS (3×) and combined prior to lysis in Urea lysis buffer [8 M Urea, 50 mM NH4HCO3, nicotinamide (1 mM), phosphatase inhibitor cocktail (Sigma Aldrich), and EDTA-free complete protease inhibitor (Roche), pH 8.0] by sonication at 4° C. After sonication insoluble debris was cleared by centrifugation (17,000 g, 10 min), diluted with Milli-Q water to give 1 M urea, and lysate was incubated with Anti-FLAG M2 resin (100 μL slurry, A2220, Sigma Aldrich) at 4° C. overnight while rotating. For SILAC label-swap experiments, "light" HEK293T cells were incubated with CBR-470-1 and "heavy" cells were incubated with DMSO and processed as above. FLAG resin was washed with PBS (7×1 mL), FLAG-KEAP1 protein eluted with glycine-HCl buffer (0.1 M glycine, pH 3.5, 2×500 μL), followed by 8 M urea (2×100 μL). The combined eluent was brought up to 8 M urea total concentration and processed for trypsin digestion and LC-MS/MS analysis as indicated above.

The SILAC maps were generated by comparing SILAC ratios for each peptide, relative to the median value for all KEAP1 peptides. SILAC ratios were converted to Log 2 values and plotted to visualize peptides that are significantly perturbed, for example by modification, relative to the rest of the protein. A minimum of three SILAC ratios for each peptide was required for inclusion in KEAP1 surface maps, which allowed for ~85-90% coverage of the KEAP1 protein. Missing sequences were caused by the lack or close spacing of tryptic sites, resulting in inadequate peptides for MS/MS detection.

In vitro MGx-Peptide Reactions. 'CR' peptide was synthesized using standard solid phase peptide synthesis with FMOC-protected amino acids on MBHA rink amide resin. Peptides were cleaved in a solution of 94% trifluoroacetic acid, 2.5% triisopropyl silane, 2.5% H2O, 1% β-mercaptoethanol (βME) and precipitated with ether. Peptide identity was confirmed using an Agilent 1100 series LC-MS. Peptides were purified via reverse phase HPLC on an Agilent Zorbax SB-C18 250 mm column and dried via lyophilization. For methylglyoxal reactions CR peptide (1 mM) was incubated with 12.5 mM methylglyoxal (diluted from 40% solution in water; Sigma Aldrich) or equivalent amount of water (mock) in 1×PBS pH 7.4 at 37° C. overnight. Reactions were diluted 1:25 in 95/5 H2O/Acetonitrile+0.1% trifluoroacetic acid and analyzed by LC-MS.

For NMR experiments, approximately 1.5 mg of the CR or CR-MGx crosslinked peptide was purified by reverse phase HPLC, lyophilized and dissolved in 700 μL d6-DMSO. The peptides was dried via lyophilization. All NMR experiments were performed on a Bruker Avance II+ 500 MHz 11.7 Tesla NMR. Data was processed and plotted in Bruker Topspin 3.5. CR peptide NMR experiments were run with a spectral width of 8.5 for 2D experiments (in both dimensions) and 15 for 1D proton NMR with a pulse width of 13.5 μs and an interscan delay of 3 s. For the proton NMR, 256 scans were taken. For the COSY-DQF experiment, 128 and 2048 complex points were acquired in the F1 and F2 dimensions respectively, with 8 scans per point. For the TOCSY experiment, a mixing time of 60 μs was used, and 256 and 1024 complex points were acquired with 8 scans per point. All CR-MGx peptide NMR experiments were run with a spectral width of 13 (in both dimensions) with a pulse width of 11.5 μs and an interscan delay of 2.2 s. For the proton NMR, 256 scans were taken. For the COSY-DQF experiment, 128 and 2048 complex points were acquired in the F1 and F2 dimensions respectively, with 8 scans per point. For the TOCSY experiment, a mixing time of 80 μs was used, and 256 and 1024 complex points were acquired with 8 scans per point.

In-gel digestion of KEAP1 Targeted proteomic analyses of KEAP1 protein were performed by running anti-FLAG enriched HMW-KEAP1 and LMW-KEAP1 (from both CBR-470-1 or MGx treatments as above) on SDS-PAGE gels, and isolated gel pieces were digested in-gel with sequencing grade trypsin (Promega), as previously reported[35]. Tryptic peptides from in-gel tryptic digestions were dissolved in 100 mM Tris-HCl, pH 8.0, with 2 mM of CaCl2), and further digested with mass spectrometry-grade chymotrypsin (Thermo Scientific) according to manufacturer's protocol. Chymotryptic digestion reactions were stopped by acidification, and desalted on Ziptip C18 tips.

Targeted proteomic analysis of crosslinked KEAP1 peptides. Double digested KEAP1 peptides from isolated HMW-KEAP1 and monomeric KEAP1 were analyzed by LC-MS/MS on an Easy-nLC 1000 ultra-high pressure LC system coupled to a Q Exactive HF orbitrap and Easy-Spray nanosource as indicated above. Candidate peptides were initially searched by manual inspection of chromatograms and MS1 spectra for m/z values of peptide candidates from predicted digestion sites, crosslink sites and differential presence in HMW- and monomeric KEAP1 from both CBR-470-1 and MGx treated samples. Extracted MS1 ions of the candidates were present in HMW-KEAP1 digests but not in LMW-KEAP1 digests. MS/MS spectra and PRM experiments were collected on the same instrument using the following settings: Global and general settings included lock masses of off, chromatography peak width of 15 seconds, polarity of positive, in-source CID of 0.0 eV, inclusion list set to 'on,' and an m/z value of the target parent ion with its charge state in the inclusion list. MS2 scans were performed by HCD fragmentation with microscans of 1, resolution of 120,000, AGC target of 5e5, maximum IT of 200 ms, loop count of 1, MSX count of 1, isolation window of 2.0 m/z, isolation offset of 0.0 m/z, NCE of 16, and spectrum data type in profile mode. Furthermore, S-lens RF level was set to 60 with a spray voltage value of 2.20 kV and ionization chamber temperature of 275° C. Targeted PRM experiments were performed on CBR-470-1-, MGx-induced HMW-KEAP1 and monomeric KEAP1 samples.

UVB Skin Damage Model. 32 5-week old Balb/c male mice were randomized into 4 groups of 8 animals such that each group had similar body weight means. Mice were prepared for removal of hair from their entire back two days prior to UVB exposure (day 3) by using an electric shaver and depilatory cream. On day 5, mice received exposure to UVB (200 mJ/cm$^2$) produced by a broad band UVB lamp (Dermapal UVB Rev 2) powered by a Kernel UV Phototherapy system. UVB exposure was confined to a rectangular area of ~8 cm$^2$ by a lead shielding mask. UVB doses were confirmed by dosimeter measurements (Daavlin X96). Sham animals were shaved but received no UVB treatment. Mice were dosed from day 0 to study end at day 10 via oral gavage twice daily (CBR-470-2, 50 mg/kg BID PO; BARD, 3 mg/kg PO; Vehicle, 0.5% methyl cellulose/0.5% Tween80). Mice were monitored daily for body weight changes and erythema scoring from days 5 to 10. Mice were sacrificed at day 10 and specimens collected for histological analysis from the wounded area. These studies were performed at Biomodels, LLC (Watertown, MA). Blinded erythema scores were recorded by a blinded, trained investigator according to established in house scale. In short, a scale of 0 to 4 was generated with a score of 0 referring to normal skin and a score of 4 indicating severe ulceration.

Percent wounded area measurements. Photographs of animals on day 10 of the study were taken such that the distance from camera, aperture, and exposure settings were identical. Images were then cropped such that only the shaved, wounded area encompassed the imaging field. These images were then processed with a custom ImageJ macro which first performed a three color image deconvolution to separate the red content of the image[36]. The thresholding function within ImageJ software was then used to separate clear sites of wounding from red background present in normal skin. Red content corresponding to wounds was then quantified as a fraction of the whole imaging field and reported as percent wounded area.

Epidermal thickness measurements. H&E stained skin sections corresponding to the wounded area were generated by Histotox Labs and accessed via pathxl software. 24 individual measurements of epidermal thickness from 8 sections spanning a 400 μm step distance were recorded per animal by a non-blinded, trained investigator. These measurements were then averaged to generate a mean epidermal thickness measurement per animal.

Example 2

Figure 24A:
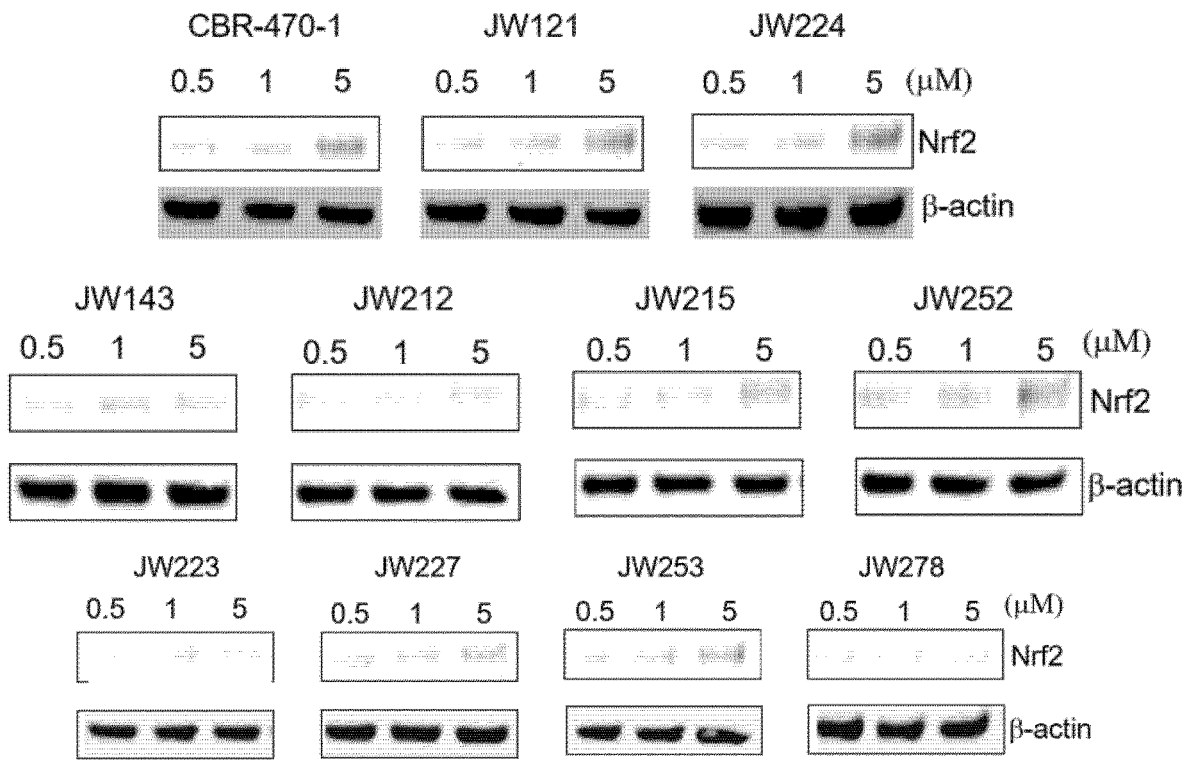
FIG. 24A-B. Western blot of NRF2 levels as a function of increasing concentration of (a) CBR 470-1, JW121, JW224, JW143, JW212, JW215, JW252, JW223, JW227, JW253, JW278. (b) illustrates the relative NRF2 activation as a function of concentration for CBR 470-1, JW121, and JW224.
Figure 24B:
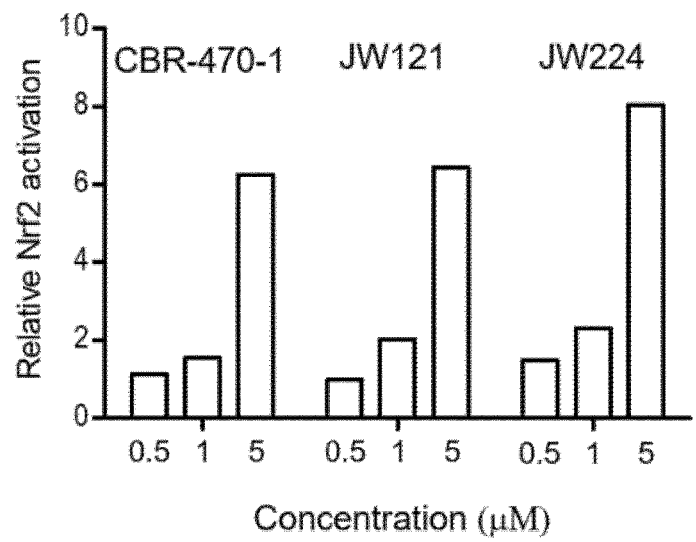
Figure 25:
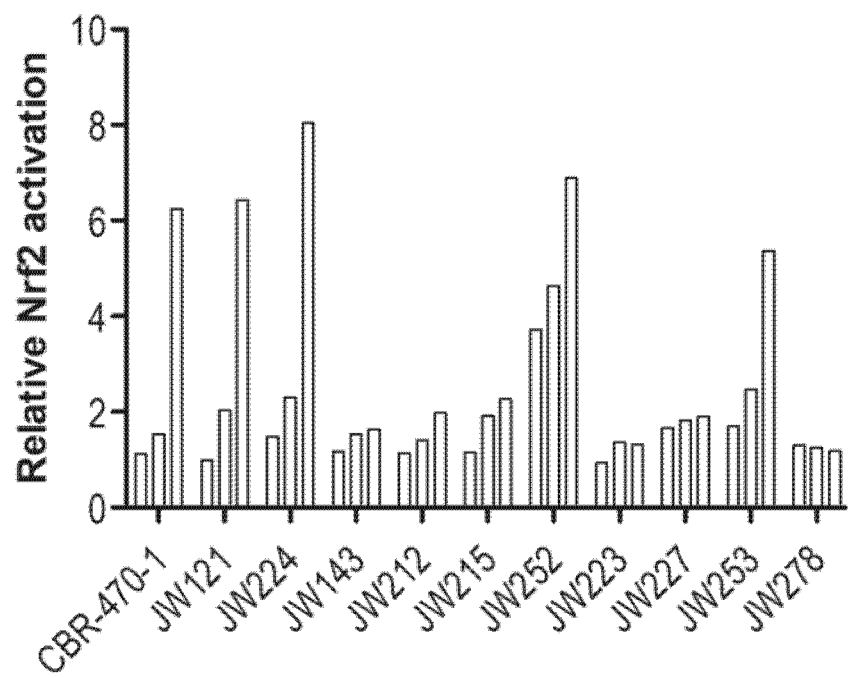
FIG. 25. Relative NRF2 activation as a function of concentration for CBR 470-1, JW121, JW224, JW143, JW212, JW215, JW252, JW223, JW227, JW253, and JW278.
Figure 26:
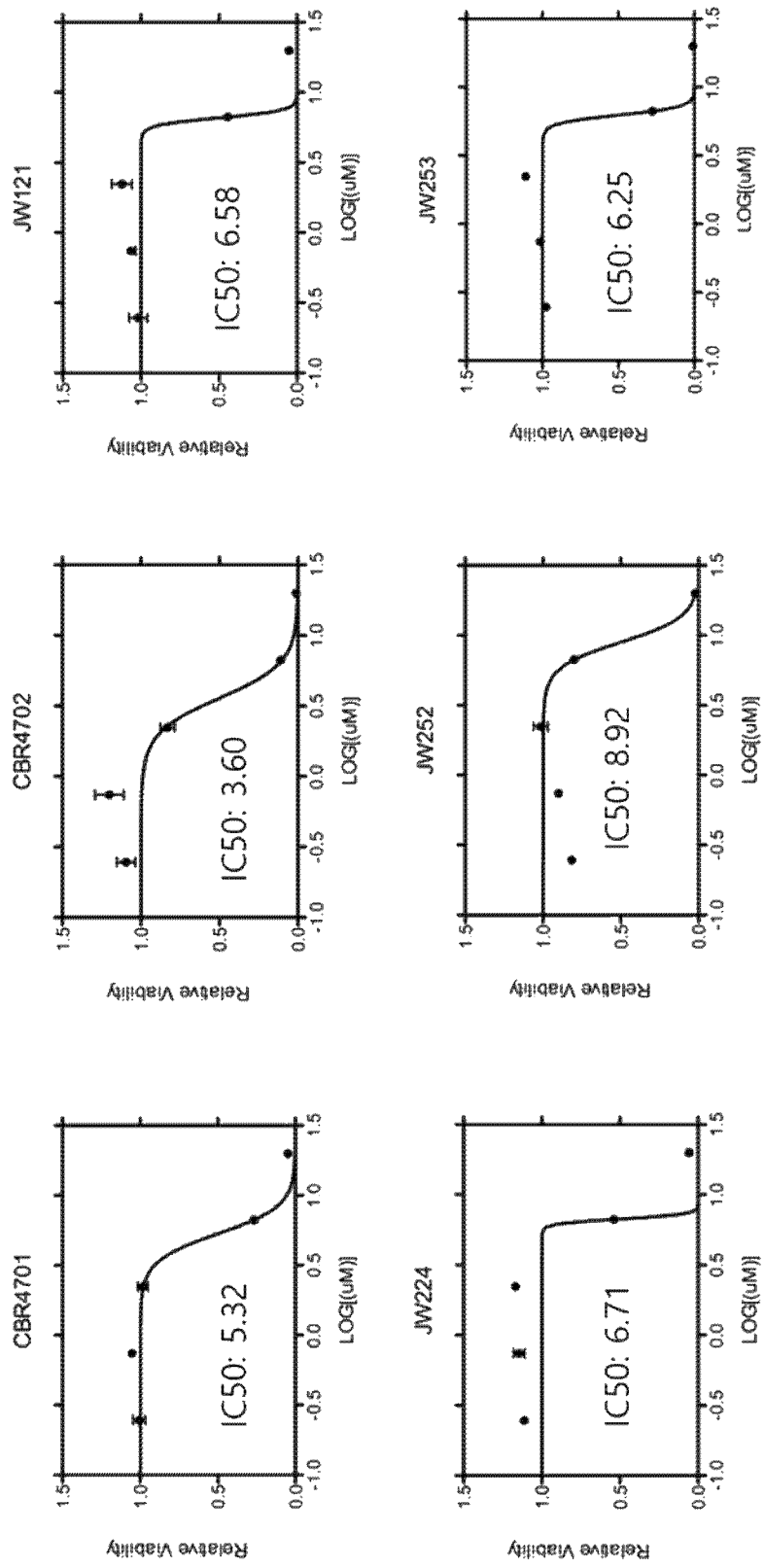
FIG. 26. Illustration of the relative viability as a function of increasing concentration of CBR 470-1, CBR 470-2, JW121, JW224, JW252, and JW253.
Figure 27:
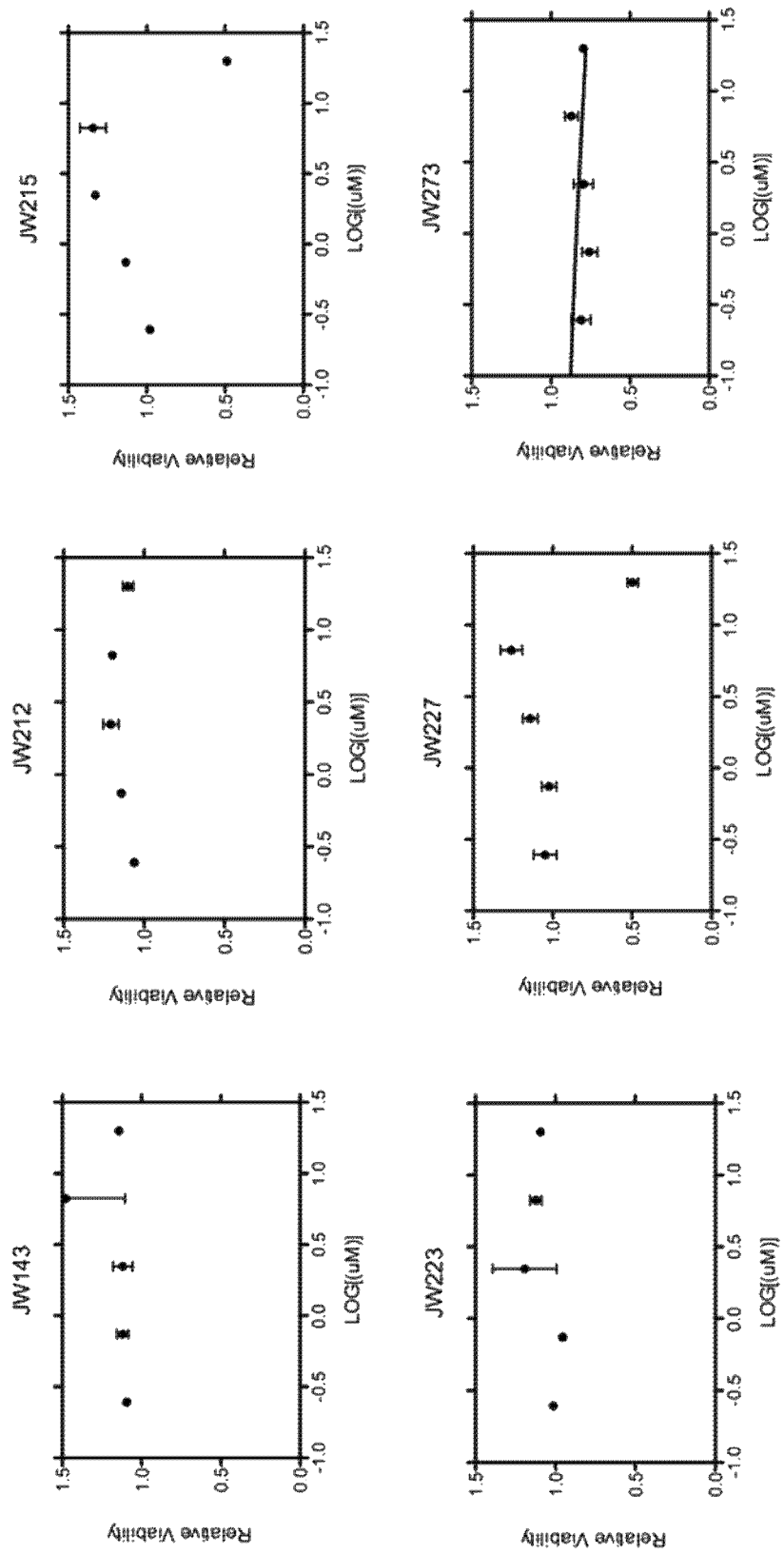
FIG. 27. Illustrates the relative viability as a function of increasing concentration of JW143, JW212, JW215, JW223, JW227, and JW273.
Figure 28:
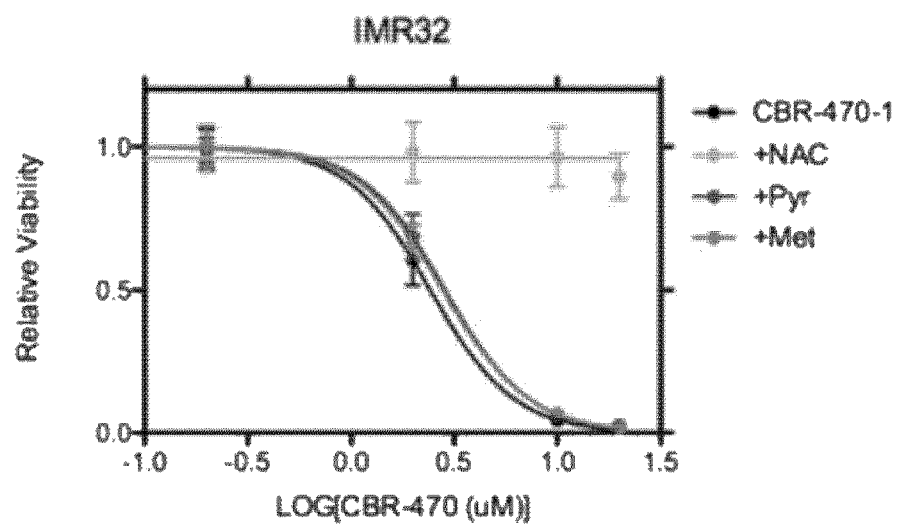
FIG. 28. Co-treatments modulate effects of CBR-470-1. Illustrating the differential sensitivity of the basal cell lines to CBR470-1 treatment, which is indicative of some cancer cell lines being susceptible to anti-proliferative effects in vivo when other cell types or tissues are not.
Figure 29A:
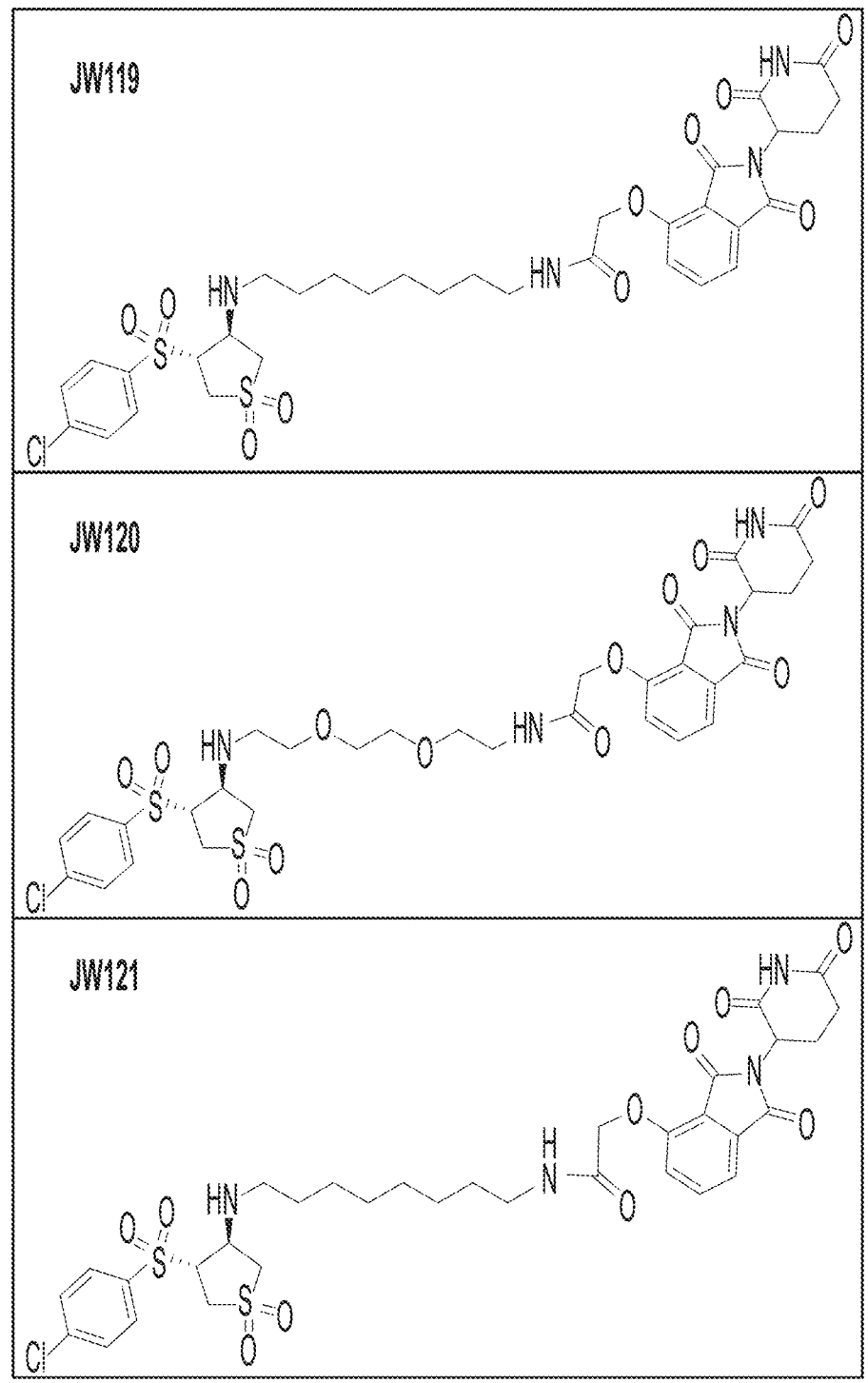
Figure 29A:
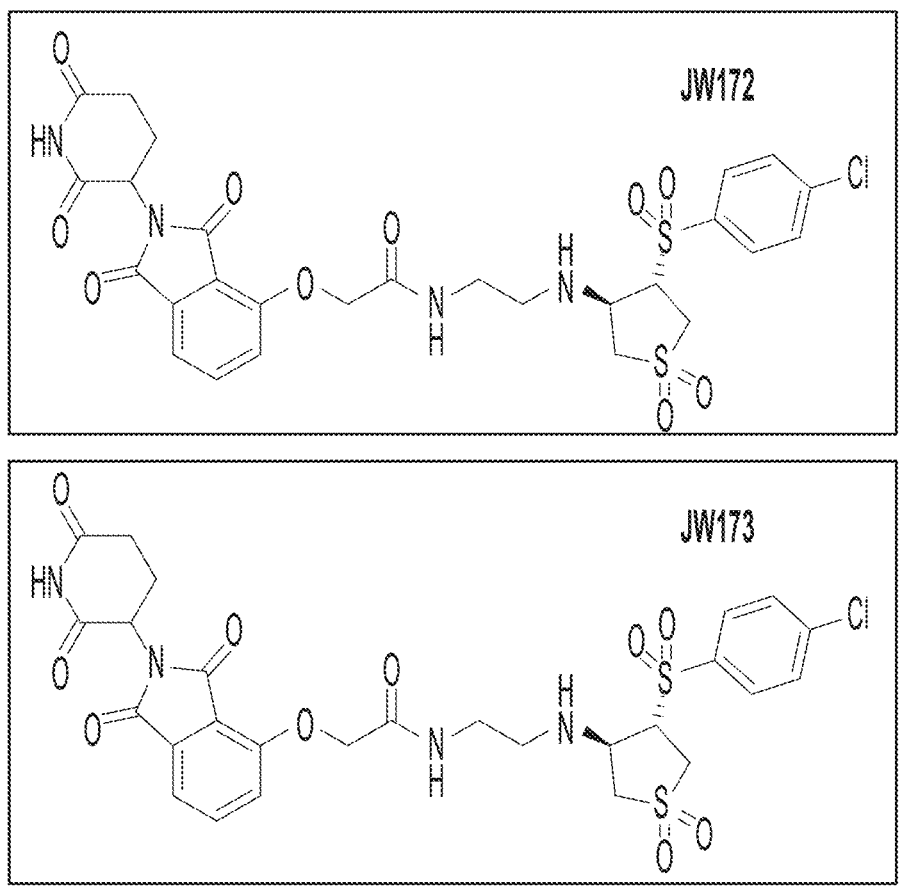
Figure 29A:
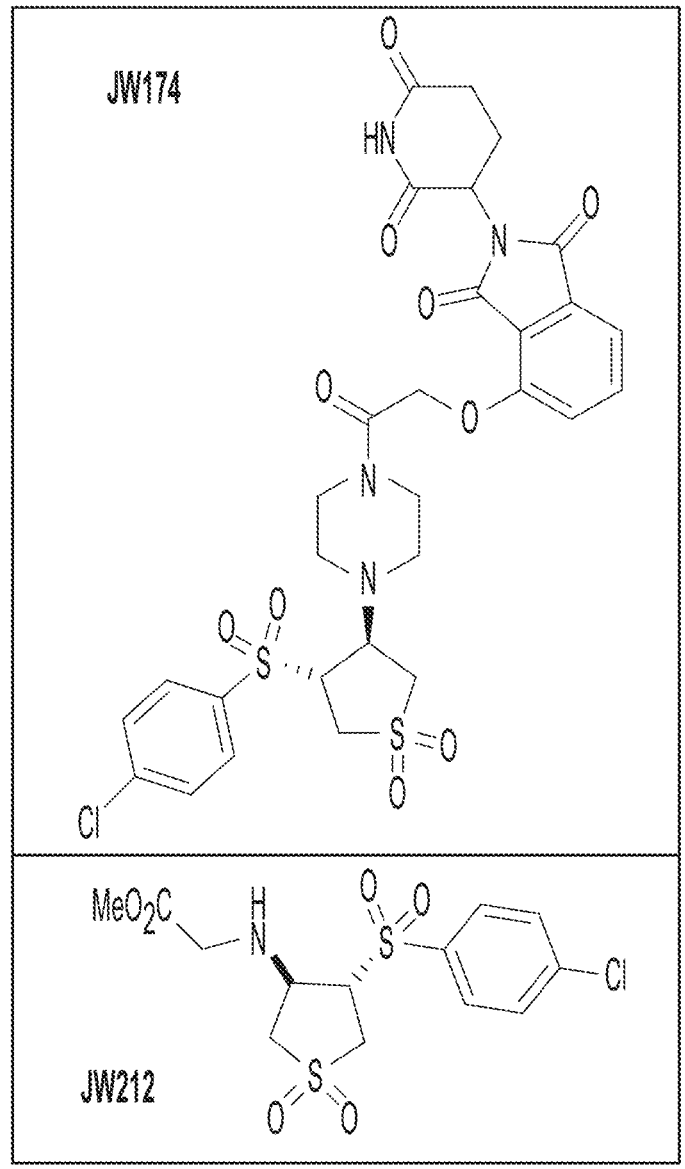

Small Molecule Activators of NRF2 Transcriptional Program, NRF2-Dependent Gene Expression NRF2 activation measured by western blot in H1299 cells treated with indicated compound at indicated dose for 8 hr (FIG. 24, 25). Beta-actin levels served as loading control for all experiments. Compound viability screening in IMR32 for 48 hr. Viability measured by cell titer glo quantification. IC50 values are listed in micromolar (FIG. 26, 27).

Example 3

Figure 22:
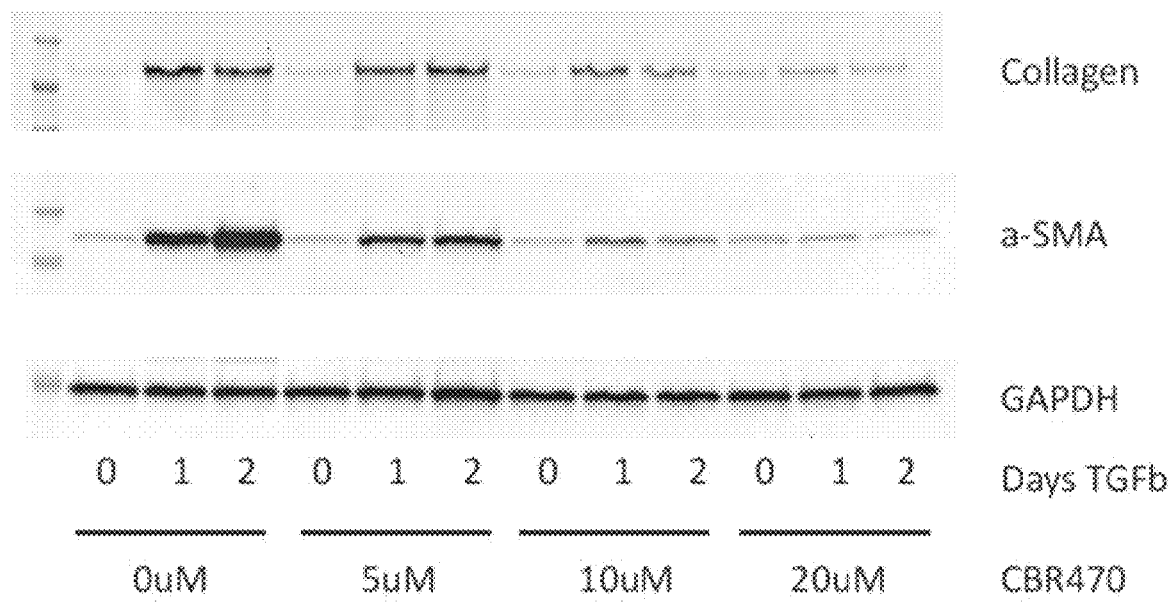
FIG. 22. Human lung fibroblasts were treated with TGF-beta and increasing doses of CBR-470 and measured collagen and alpha-smooth muscle actin (a-SMA), a marker for myofibroblast differentiation at day 0, 1, and 2. CBR-470-1 inhibited myofibroblast differentiation and collagen protein expression in a dose dependent manner.

NRF2 Activation and Glycolytic Suppression with CBR-470-1 Abrogates Collagen Synthesis by Lung Fibroblasts—A Disease Phenotype in Fibrotic Disease Fibrosis is defined by the overgrowth, hardening, and/or scarring of various tissues and is attributed to excess deposition of extracellular matrix components including collagen. Fibrosis is the end result of chronic inflammatory reactions induced by a variety of stimuli including persistent infections, autoimmune reactions, allergic responses, chemical insults, radiation, and tissue injury. Fibroblasts under stimulation by transforming growth factor (TGF)-β, a key cytokine in the pathogenesis of IPF, alter their gene expression profile with de novo expression of cytoskeletal and contractile proteins normally found within smooth muscle cells, and components of the extracellular matrix, including collagen. Fibroblast cells were treated with TGF-β for 24 or 48 hours or left untreated (0). Collagen was detected by Westernblot using an anti-collagen antibody (Cedarlane, CL50111AP-1, 1:3000 dilution). SMA was detected with an anti-SMA antibody from Sigma (T6074, 1:20000 dilution). CBR-470-1 treatment shows dose- and time-dependent inhibition of collagen and smooth-muscle actin (SMA) protein production in human lung fibroblasts induced by TGFb (in vitro treatments). Collagen and SMA production are biomarkers of fibrotic phenotypes in vivo (FIG. 22).

Example 4

NRF2 Activation and Glycolytic Suppression with CBR-470-1 Abrogates Opposes Inflammatory Cytokine Production in Acute Lung Injury Models In Vivo Systemic CBR-470-2 treatment in acute lung injury mouse model reduces bronchial alveolar lavage (immune cells) cell TNF, IL1b and IL6 production (FIG. 23). C57/B6 Mice were treated with either CBR-470-2 (50 mg/kg dissolved in water and NaOH (1:1)) or vehicle (NaOH) intraperitoneally, and intratracheally instill 0.7 mg/kg of lipopolysaccharide (LPS) to induce active lung injury. Mice which received CBR-470-2 had decreased TNF, IL6, and IL1b production but not KC. Examination of lung tissue gene expression demonstrated decreased gene expression of IL6 but not TNF, IL1b or KC (KC=chemokine (CXC motif) ligand 1 (CXCL1)) in mice treated with CBR470-2.

Example 5

Synthesis of Compounds Having Formula I

Compounds of formula II was synthesized according to scheme I, II or III

Scheme I

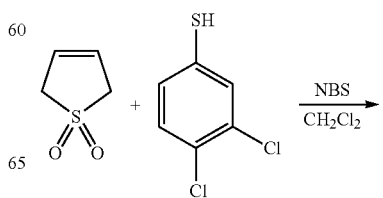

-continued
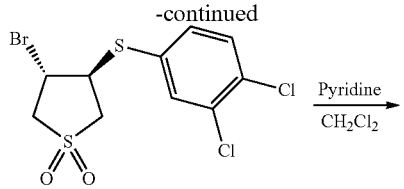
CRBN Ligand Synthesis
Scheme II
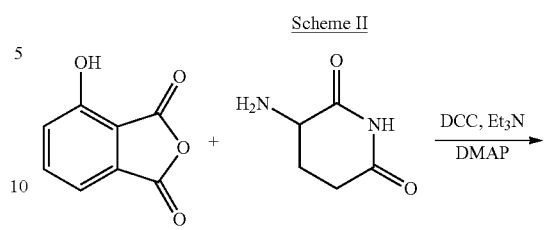
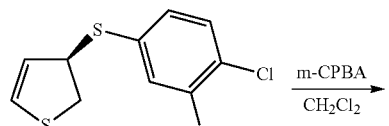
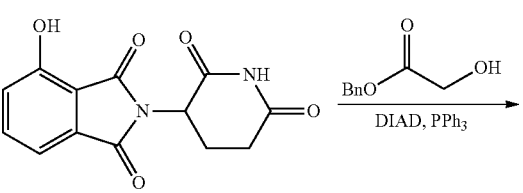
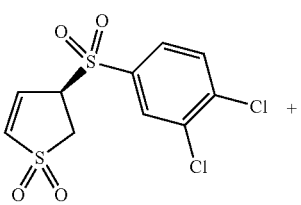
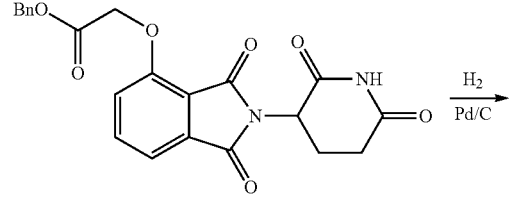
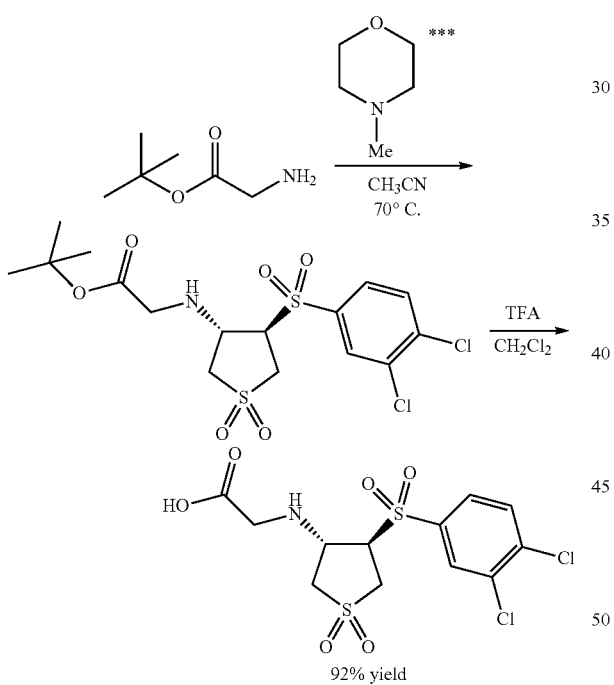
92% yield
JW121 synthesis
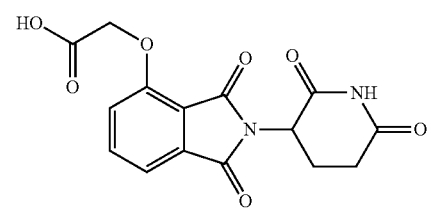
Scheme III
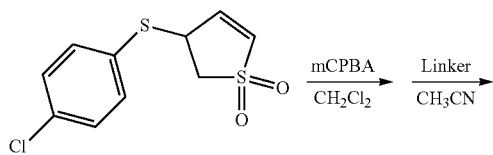

-continued

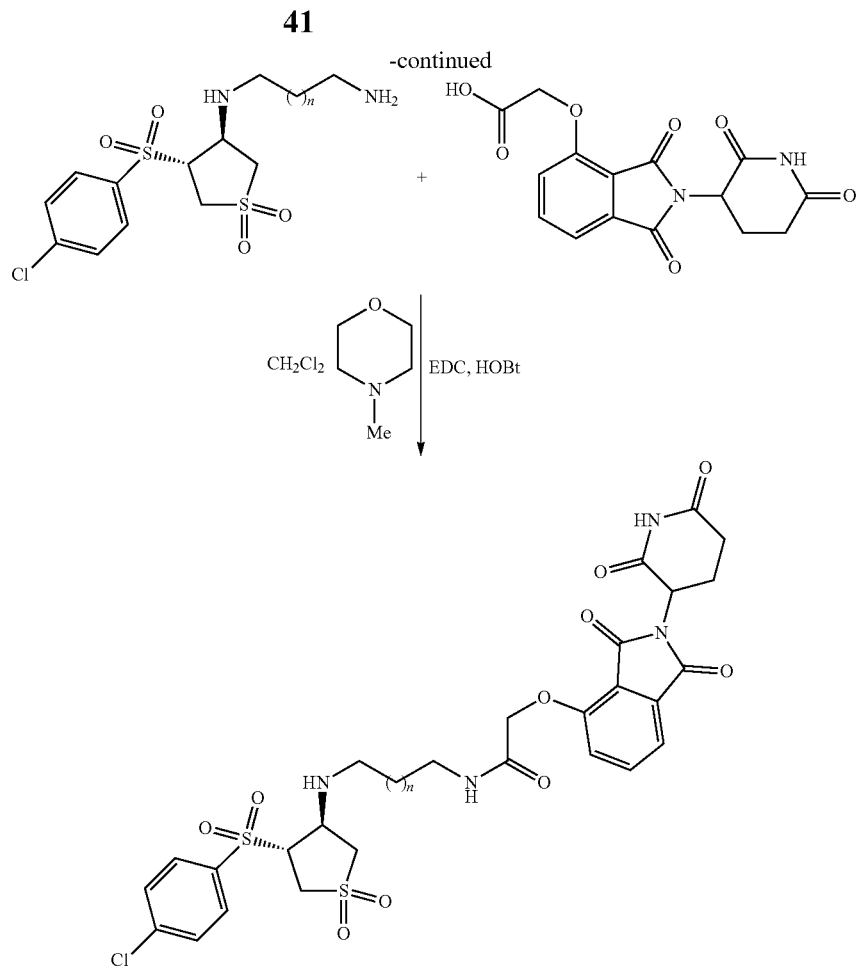

Example 6

CBR-470-1 Activates NRF2 and Inhibits PM-Induced Inflammatory Cytokine Production from Alveolar Macrophages Indicated transcript levels in response to PM exposure for 4 hr in the presence and absence of CBR-470-1, PGK1 inhibitor (10 micromolar). Western blot analysis of NRF2 protein levels. PM-exposure also results in activation of the NRF2 pathway, which is confirmed by increased transcript levels of its prototypical target Nqo1 (FIG. 30c) and NRF2 protein accumulation (FIG. 30d). Direct targeting of the Glycolytic-NRF2 axis through inhibition of PGK1 with CBR-470-1 results in dose-dependent decreases in Il6 and Tnfα mRNA levels in both control and PM-treated cells (FIG. 30a, 30b). CBR-470-1 treatment also activates NRF2-signaling in both control and PM-treated macrophages (FIG. 30c, 30d). FIG. 31 illustrates time dependent effects of CBR-470-1 on alveolar macrophage cytokine mRNA levels at specific timepoints. FIG. 32 shows CBR-470-1 does not cause significant ROS elevation in alveolar macrophages, and only a slight decrease in overall cellular bioenergetics in this cell and metabolic background. This represents a distinct mechanism of action compared to many other pharmacologic NRF2 activators, which achieve efficacy through induction of ROS (reactive oxygen species).

CBR-470-0

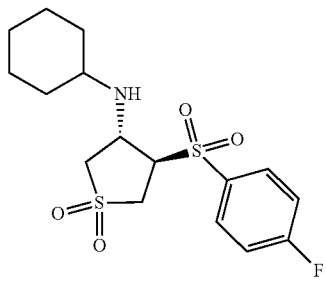

CBR-470-1

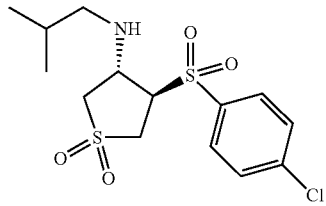

Example 7

Inhalational Exposure to Concentrated Ambient Particles (CAPs)

FIG. 33A shoes a photograph of and FIG. 33B a schematic of a VACES PM$_{2.5}$ impactor and chambers depicting how mice are exposed to CAPs or filtered air (FA). The $PM_{2.5}$ generated from ambient air are delivered to murine chambers housing up to 32 mice each (with food and water). Control mice are housed in an identical chamber, connected to the VACES with a Teflon filter placed in the chamber inlet. FIG. 33C shows ambient and delivered particle concentrations are measured using a TSI 3775 particle counter Particle concentrations are about 10-fold higher or lower than ambient air levels in the CAPs and FA chambers, respectively. $p<0.05$, *CAPs and †FA vs. ambient air. FIG. 33D illustrate a timeline for exposure to PM (8 h/d×3 days).

Identification of tissue resident (TR-AMs) and monocyte-derived (Mo-AMs) alveolar macrophages using PKH26 dye method. Mice are treated with PKH26 Red Fluorescent Cell Linker dye (Sigma) 1 day prior to intratracheal instillation of PM (10 μg/mouse). The PKH26 labels the lipid membrane of tissue resident alveolar macrophages (TR-AMs), but not the bone marrow cells from which infiltrating monocyte-derived recruited macrophages (Mo-AMs) arise. Following PM exposure, cells were collected and stained with F4/80 antibody to select for macrophages. Then TR-AMs (PKH26+) and recruited Mo-AMs (PKH26−) were flow-sorted based on PKH26 fluorescence. Flow cytometry plots show that (FIG. 34A) TR-AMs are the only subpopulation of AMs on day 0 and (FIG. 34B) both Mo-AMs and TR-AMs are seen following PM.

Inhibition of PGK1 (CBR-470) attenuates PM-induced cytokine production from alveolar macrophages in mice. C57Bl/6 mice were exposed to either PM or filtered air 8 h/day for 3 days while receiving either CBR-470 or control vehicle. At the end of exposure, alveolar macrophages were isolated and measured mRNA expression of (FIG. 35A) Tnfa and (FIG. 35B) Il6. Expression data is shown relative to FA samples and control housekeeping gene.

Example 8

Figure 37:
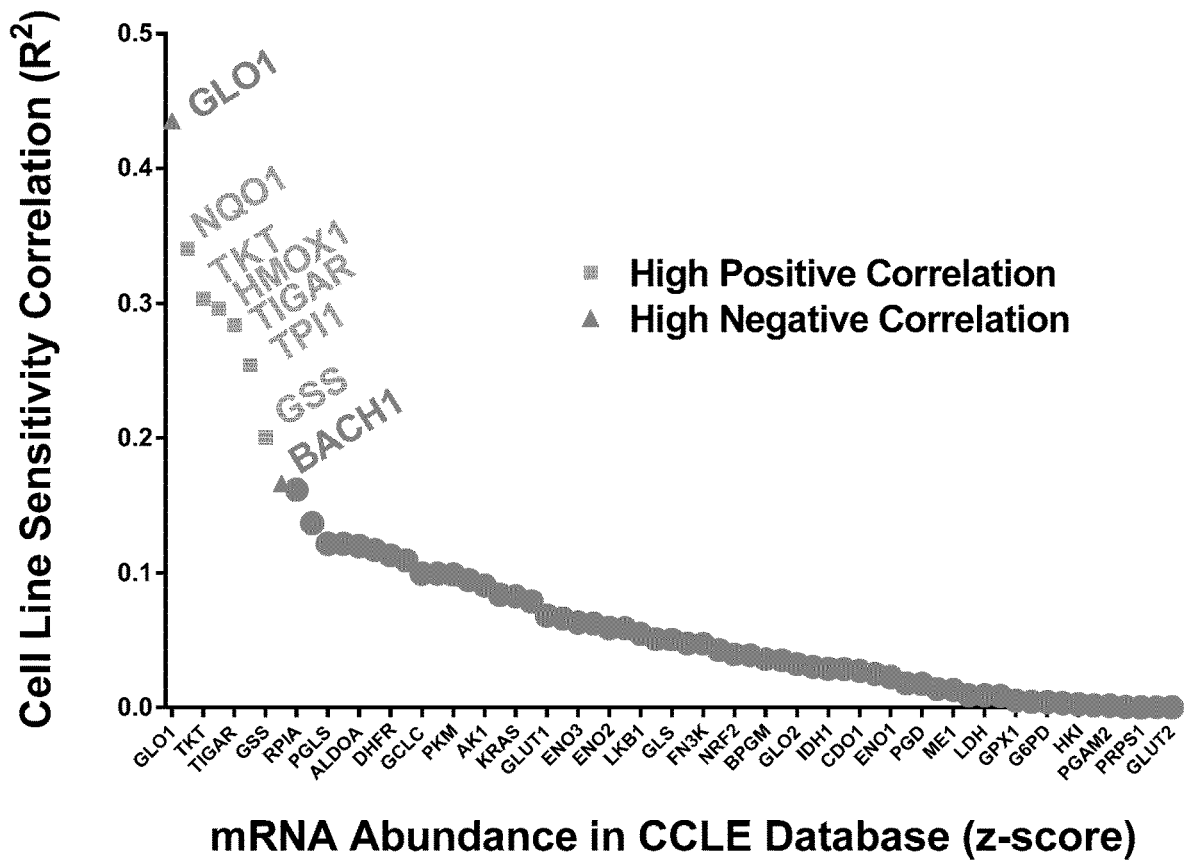
FIG. 37. Each point represents the correlation value ($R^2$) between cell line IC50 value (i.e. sensitivity) to CBR-470 plotted against the relative mRNA level (Z-score) for that cell line, and all other cell lines in the 20 line panel. mRNA levels were curated from the cancer cell line encyclopedia (CCLE)

Genetic Determinants of Cancer Cell Sensitivity to Growth Inhibition by PGK1 Inhibition or Inhibition of Central Metabolism Each point in FIG. 37 represents the correlation value ($R^2$) between cell line IC50 value (i.e. sensitivity) to CBR-470 plotted against the relative mRNA level (Z-score) for that cell line, and all other cell lines in the 20 line panel. mRNA levels were curated from the cancer cell line encyclopedia (CCLE). Cell lines with lower NRF2 target gene expression show increased sensitivity to PGK1 inhibition with CBR-470-1. Cell lines with high GLO1 exhibit higher sensitivity to PGK1 inhibition with CBR-470-1.

Figure 38:
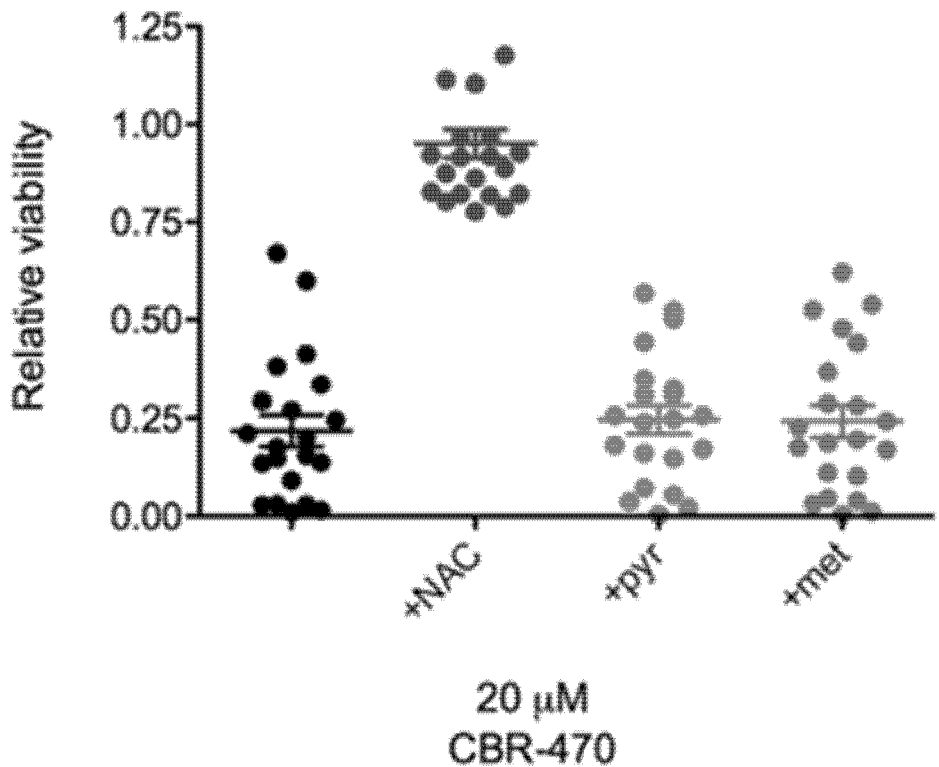
FIG. 38. PGK1 toxicity can be rescued with metabolites that are involved with GSH biosynthesis and quenching of reactive oxygen species and methylglyoxal. Replacement of lower glycolysis metabolites (pyruvate, pyr) and inhibition of oxidative phosphorylation with metformin (met) do not strongly effect viability effect of PGK1 inhibition across cell lines, on average. IMR32 cells treated for 48 hr in presence of indicated drugs.

PGK1 toxicity can be rescued with metabolites that are involved with GSH biosynthesis and quenching of reactive oxygen species and methylglyoxal. Replacement of lower glycolysis metabolites (pyruvate, pyr) and inhibition of oxidative phosphorylation with metformin (met) do not strongly affect viability effects of PGK1 inhibition across cell lines, on average (FIG. 38).

Figure 39:
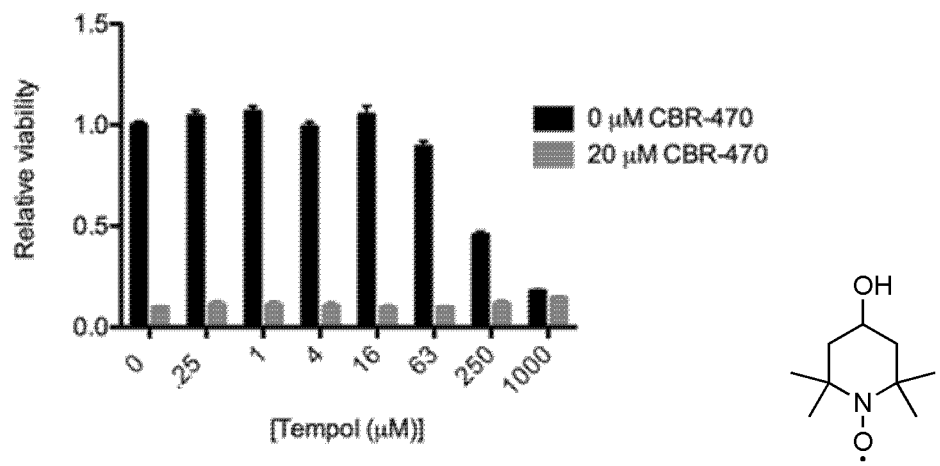
FIG. 39. Co-treatment of cells with a ROS scavenger, Tempol, does not effectively reduce anti-proliferative effects of CBR-470-1. Combined with NAC data, this suggests that reactive metabolite quenching (like MGO) and not a purely ROS-based mechanism underlies the toxicity of PGK1 inhibition.

Co-treatment of cells with a ROS scavenger, Tempol, does not effectively reduce anti-proliferative effects of CBR-470-1 (FIG. 39). Combined with NAC data, this suggests that reactive metabolite quenching (like MGO) and not a purely ROS-based mechanism underlies the toxicity of PGK1 inhibition.

Figure 40:
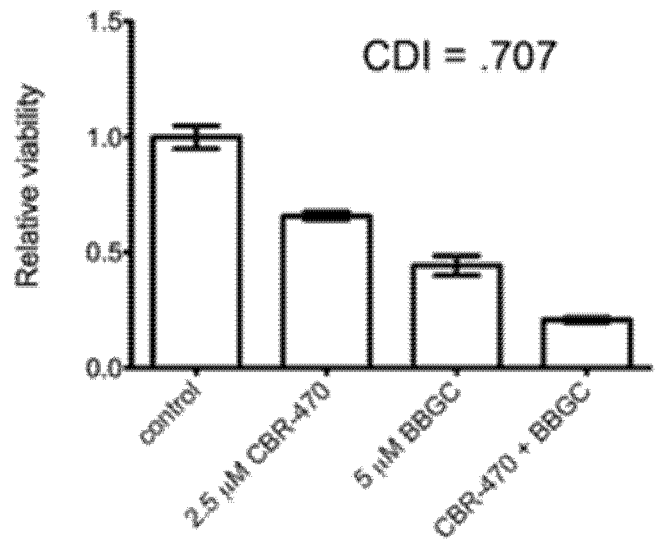
FIG. 40. Inhibition of central metabolism (PGK1) shows synergy with inhibition of GLO1.
Figure 41:
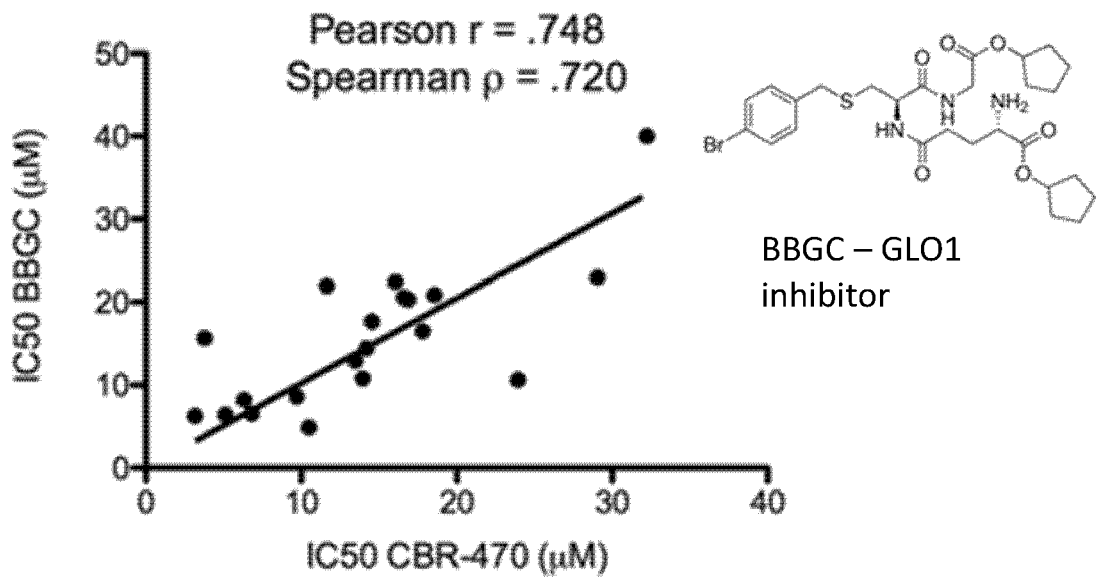
FIG. 41. Sensitivity of cell lines to direct inhibition of GLO1 (which detoxifies MGO) is generally correlated with sensitivity to PGK1 inhibition with CBR-470-1-consistent with MGO buildup playing a role in toxicity.

Inhibition of central metabolism (PGK1) shows synergy with inhibition of GLO1 (FIG. 40). IMR32 cells were treated for 48 hrs with CBR-470-1 and/or BBGC at combinations of doses in a synergy matrix (FIG. 41). Specific combinations show synergistic effects on viability rather than additivity. Viability measured using cell titer glo assay (Promega). Viability decreased at higher concentrations of CBR-470-1 and BBGC start at 5 uM. CDI is correlation of drug interaction, for which values <1 suggest synergistic activity. These results suggests that MGO toxicity is involved in cell viability effects of central metabolism inhibition and that combinations targeting this axis may be therapeutically useful. Sensitivity of cell lines to direct inhibition of GLO1 (which detoxifies MGO) is generally correlated with sensitivity to PGK1 inhibition with CBR-470-1-consistent with MGO buildup playing a role in toxicity.

Genetic manipulation of central glycolytic targets GLO1 and PGK1 regulate viability in the very sensitive colorectal cancer cell line HCT116. In line with genetic correlations, acclimation of cells to low GLO1 levels results in resistance to CBR-470-1 metabolic inhibition PGK1 knockdown cells grow more slowly and are more sensitive to CBR-470-1 metabolic inhibition. (FIG. 42). FIG. 43 shows IMR32, a more sensitive cell line to the anti-proliferative effects of CBR-470-1, exhibits reduced glycolytic flux and oxidative phosphorylation rate, as measured by global bioenergetics with a Seahorse XF96 global metabolic profile of Extracellular Acidification Rate (ECAR) and Oxygen Consumption Rate (OCR). Cells were plated for 24 hrs., then incubated with the indicated doses of CBR-470 for 1 hr. Under CBR-470-1 treated conditions, cellular ECAR and OCR was recorded for CBR-470 alone, CBR-470+10 mM Glucose, and CBR-470+3 μM Oligomycin.

Example 9

Synthesis of CBR470-1 and CBR470-2

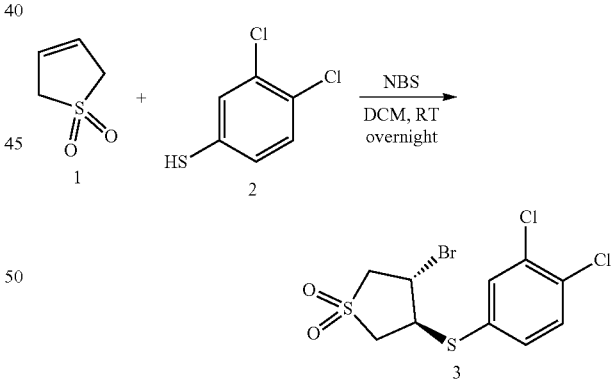

3,4-dichlorobenzenethiol (10.8 ml, 80 mmol) was added dropwise over a course of 30 minutes to a stirred solution of N-bromosuccinimide (15 g, 80 mmol) in dichloromethane (105 ml) at RT. After stirring for 45 minutes, a solution of 3-sulfolene (10 g, 80 mmol) was added dropwise to the reaction mixture and the mixture stirred overnight. Next day reaction was quenched by adding water. The aqueous layer was extracted with dichloromethane ×3. The combined organic layers were dried over $MgSO_4$ and concentrated in vacuo. The crude mixture was purified by column chromatography on silica gel (EtOAc:n-Hexane=1:5).

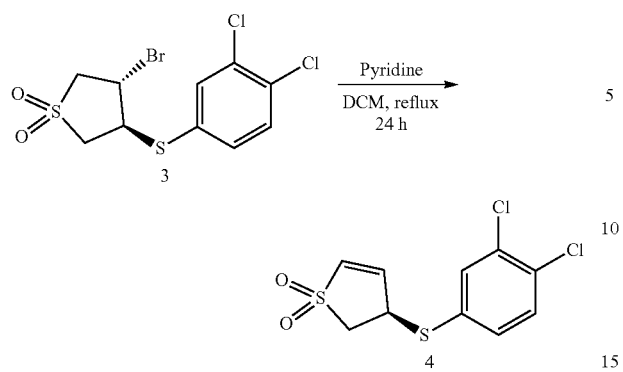

Pyridine (16 ml, 198.7 mmol) was added to a solution of 3 (20 g, 53 mmol) in dichloromethane (100 ml). After stirring under reflux for 24 hours, the reaction mixture was cooled to RT and then quenched with aq. NH$_4$Cl. The aqueous layer was extracted with dichloromethane ×3. Combined organic layers were washed with brine and dried over MgSO$_4$ and concentrated in vacuo. The crude mixture was used for next step without further purification.

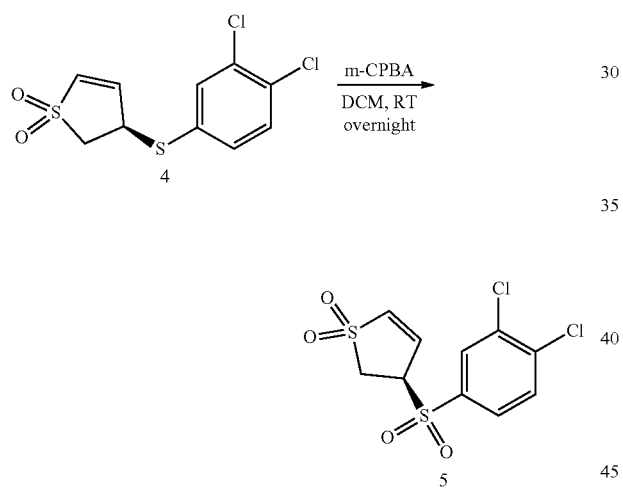

To a solution of 4 (17 g, 10 mmol) in dichloromethane (250 ml) was added meta-chloroperoxybenzoic acid (25 g, 144 mmol, 70~75%) in 3 portions. The reaction stirred overnight. The next day, the reaction mixture was filtered and quenched with NaHCO$_3$. The organic layer was washed with Brine and dried over MgSO$_4$ and concentrated in vacuo. The crude mixture was used for next step without further purification.

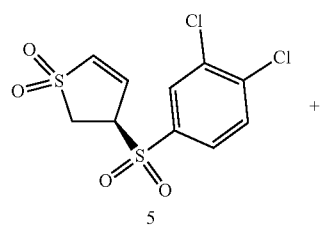

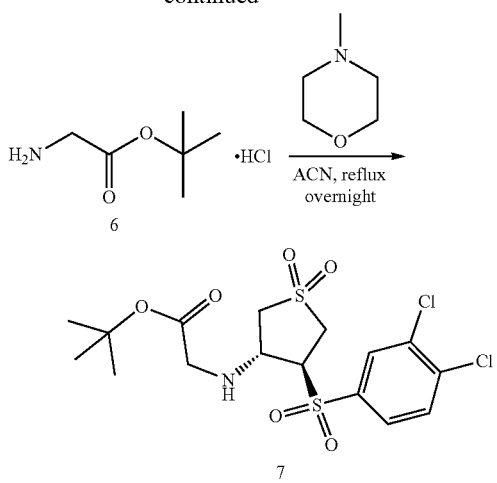

Compound 5 (3.15 g, 9.7 mmol) was dissolved in acetonitrile (80 ml) at RT. Glycine tert-butyl ester hydrochloride (6.5 g, 38.8 mmol) and N-methyl morpholine (5.3 ml, 48.4 mmol) were added to the reaction mixture. After stirring under reflux overnight, the reaction mixture was cooled to RT. Organic layer was washed with water ×3 and brine. The crude mixture was purified by column chromatography on silica gel (EtOAc:n-hexane=1:1).

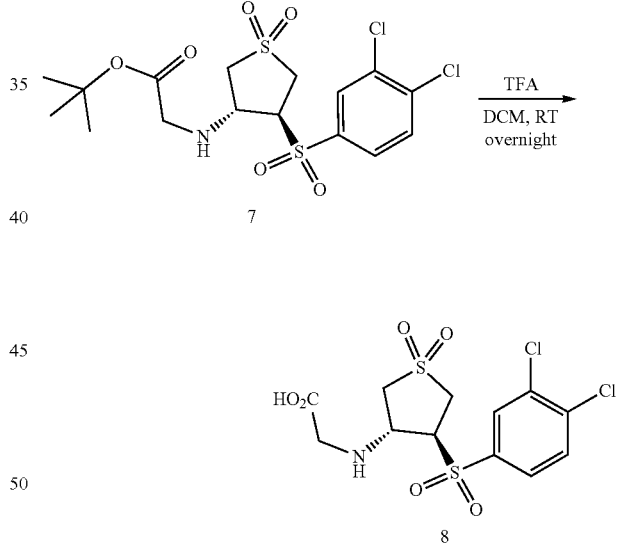

To a solution of 7 (3 g, 6.6 mmol) in dichloromethane (75 ml) was added trifluoroacetic acid (10 ml). After stirring overnight, reaction mixture was filtered to give BCBR-470-2.

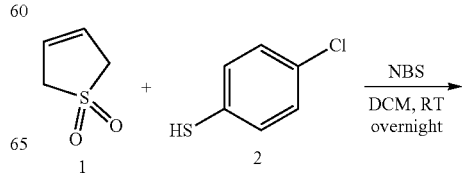

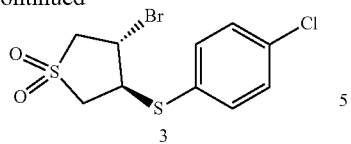

4-dichlorobenzenethiol (12.2 g, 80 mmol) was added dropwise over a course of 30 minutes to a stirred solution of N-bromosuccinimide (15 g, 80 mmol) in dichloromethane (105 ml) at RT. After stirring for 45 minutes, a solution of 3-sulfolene (10 g, 80 mmol) was added dropwise to the reaction mixture. The reaction mixture stirred overnight. Next day reaction was quenched by adding water. The aqueous layer was extracted with dichloromethane ×3. The combined organic layers were dried over MgSO₄ and concentrated in vacuo. The crude mixture was purified by column chromatography on silica gel (EtOAc:n-Hexane=1:4).

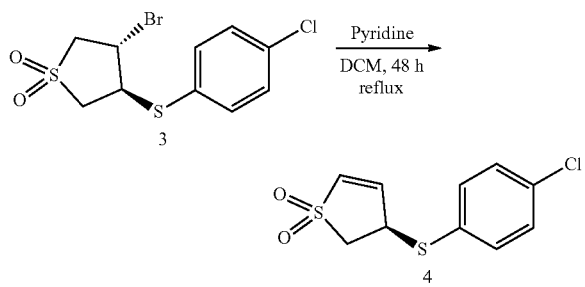

Pyridine (10.7 ml, 132.8 mmol) was added to a solution of 3 (4.7 g, 13.7 mmol) in dichloromethane (100 ml). After stirring under reflux for 48 hours, the reaction mixture was cooled to RT and then quenched with aq. NH₄Cl. The aqueous layer was extracted with dichloromethane ×3. Combined organic layer was washed with brine and dried over MgSO₄ and concentrated in vacuo. The crude mixture was used for next step without further purification.

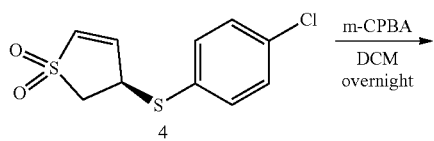

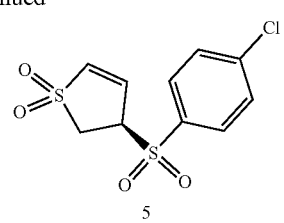

To a solution of 4 (3 g, 11.5 mmol) in dichloromethane (50 ml) was added meta-chloroperoxybenzoic acid (8.6 g, 34.8 mmol, 70~75%) in 3 portions. The reaction stirred overnight. The next day, the reaction mixture was filtered and quenched with NaHCO₃. The organic layer was washed with Brine and dried over MgSO₄ and concentrated in vacuo. The crude mixture was used for next step without further purification.

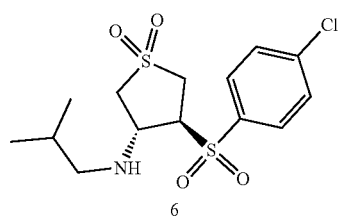

To a stirred solution of 5 (3 g, 10.2 mmol) in acetonitrile (80 ml) was added isobutylamine (1 ml, 10.2 mmol) at RT. After stirring at RT for 2 hours, solvent was removed in vacuo. The crude mixture was purified by HPLC to give CBR-470-1.

---

The invention claimed is:

1. A method for activating nuclear factor erythroid 2-related factor 2 (Nrf2) dependent gene expression by inhibiting phosphoglycerate kinase 1 (PGK1) in a subject in need thereof, comprising administering to the subject a PGK1 inhibitor having a structure selected from the group consisting of:

JW215
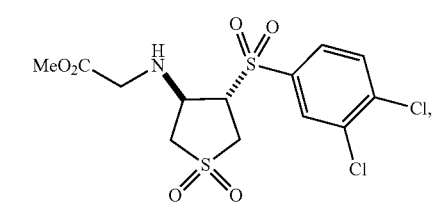

JW227
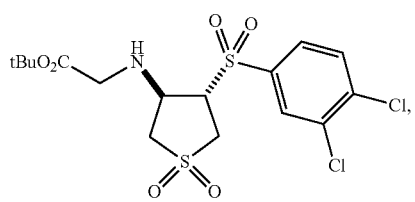

JW223
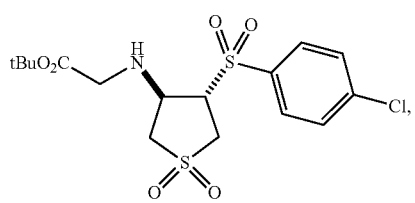

JW224
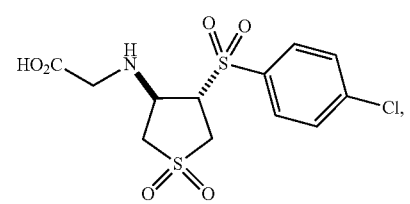

JW229
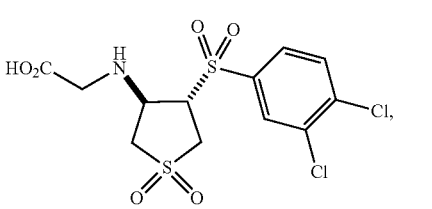
and

CBR-470-2
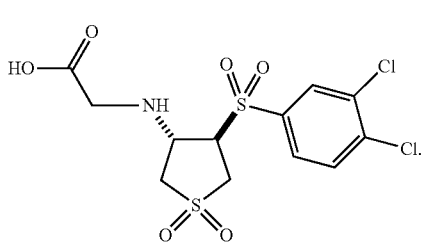

2. A method for treating a subject having pulmonary fibrosis or acute lung injury comprising administering to the subject an activator of Nrf2 dependent gene having a structure selected from the group consisting of:

JW215
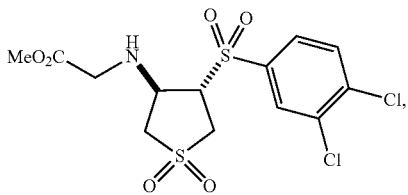

JW223
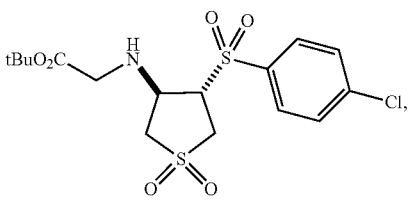

JW227
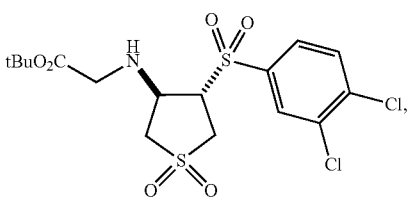

JW224
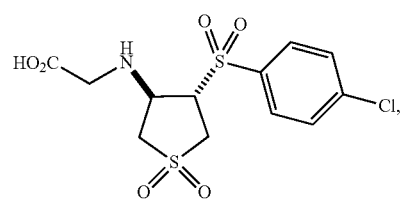

JW229
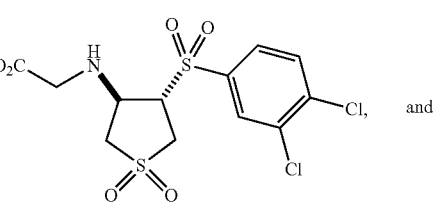
and

CBR-470-2
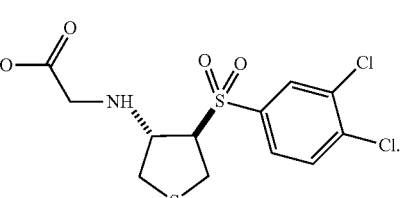

3. The method of claim 2, wherein the subject has pulmonary fibrosis.

4. The method of claim 2, wherein the subject has acute lung injury.

* * * * *

SEQUENCE LISTING

<160> NUMBER OF SEQ ID NOS: 69

<210> SEQ ID NO 1
<211> LENGTH: 624
<212> TYPE: PRT
<213> ORGANISM: Homo sapiens

<400> SEQUENCE: 1

Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

-continued

```
Tyr Ala Ser Thr Glu Cys Lys Ala Glu Val Thr Pro Ser Gln His Gly
             35                  40                  45

Asn Arg Thr Phe Ser Tyr Thr Leu Glu Asp His Thr Lys Gln Ala Phe
 50                  55                  60

Gly Ile Met Asn Glu Leu Arg Leu Ser Gln Gln Leu Cys Asp Val Thr
 65                  70                  75                  80

Leu Gln Val Lys Tyr Gln Asp Ala Pro Ala Ala Gln Phe Met Ala His
                 85                  90                  95

Lys Val Val Leu Ala Ser Ser Pro Val Phe Lys Ala Met Phe Thr
                100                 105                 110

Asn Gly Leu Arg Glu Gln Gly Met Glu Val Val Ser Ile Glu Gly Ile
            115                 120                 125

His Pro Lys Val Met Glu Arg Leu Ile Glu Phe Ala Tyr Thr Ala Ser
        130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
    290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Asn Ser Val Glu Arg Tyr Glu Pro Glu Arg Asp
        435                 440                 445
```

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
                500                 505                 510

Cys Val Leu His Asn Cys Ile Tyr Ala Ala Gly Gly Tyr Asp Gly Gln
                515                 520                 525

Asp Gln Leu Asn Ser Val Glu Arg Tyr Asp Val Glu Thr Glu Thr Trp
    530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
                580                 585                 590

Glu Val Thr Arg Met Thr Ser Gly Arg Ser Gly Val Gly Val Ala Val
    595                 600                 605

Thr Met Glu Pro Cys Arg Lys Gln Ile Asp Gln Gln Asn Cys Thr Cys
610                 615                 620

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gcctccttca tggcatagtt                                                     20

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
ggactgcacc agagccat                                                       18

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
gagtgtaagg acccatcgga                                                     20

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
gccagcaaca aagtgcaag                                                19

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ggagacgaaa tgcattcaca                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
acgaattcat ggaggcagtt                                               20

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
gcttcttgga aacttgcttc a                                             21

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
ctgtgtgatg ccaccagatt                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tcagggccgt tcatttttag                                               20

<210> SEQ ID NO 11
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 11
gatctgcccg ttgtgtttg                                                19

<210> SEQ ID NO 12

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
ggcaaagttc ttcaaagcca                                               20

<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 13
catcaaccgc cagatcaac                                                19

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
ttggaaagcc ataatcagca                                               20

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 15
caagctgggt ggcacttg                                                 18

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
cttcacgtgg atgaagtgga                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ctggcggaat gaatttgact                                               20

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide
```

```
<400> SEQUENCE: 18
gggatctctt ccacactgga t                                             21

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
catacaggcc ctgaagagga                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
gggcacacaa aggtgaagtc                                               20

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21
gctgttatgc cagatggtca g                                             21

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
tgcgtagtct ctcttcagcg                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
gcaactccta gagcggtcct                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
gggtgatctt gttcttccca                                               20

<210> SEQ ID NO 25
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
ggggaagctc ctgactatga                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
ccacaccttc actggtccat                                               20

<210> SEQ ID NO 27
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 27
ctagcgagtt atggcgacg                                                19

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
tcagggccgt tcattttag                                                20

<210> SEQ ID NO 29
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 29
gatctgcccg ttgtgtttg                                                19

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
ctcaaaaggc ttcagttgcc                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 31
acctccgctg caaatacatc                                              20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
ctttctcccc agacaggacc                                              20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
caaggacgtt ctcaagtggg                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
tggattagcg tcattccaag                                              20

<210> SEQ ID NO 35
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 35
gcggacccca gtaccaag                                                18

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cttgggacag cagccttaat                                              20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
caagctggac gttaaaggga                                              20

<210> SEQ ID NO 38

```
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 38
atctgcctcc cggtctatg                                                    19

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
tacctgtcgg aacatggagg                                                   20

<210> SEQ ID NO 40
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 40
tgaacggtgc tgtcatgtac cagatc                                            26

<210> SEQ ID NO 41
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 41
cccctcagga gactgtgact gcaggggc                                          28

<210> SEQ ID NO 42
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 42
gccctcccag catggcaa                                                     18

<210> SEQ ID NO 43
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 43
gtcacctccg ccttggactc agt                                               23

<210> SEQ ID NO 44
<211> LENGTH: 26
<212> TYPE: DNA
<213> ORGANISM: Artificial Sequence
<220> FEATURE:
<223> OTHER INFORMATION: synthetic oligonucleotide
```

<400> SEQUENCE: 44
tgaacggtgc tgtcatgtac cagatc                                           26

<210> SEQ ID NO 45
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 45
tgacgtggag gacagacttc tcgc                                             24

<210> SEQ ID NO 46
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 46
ccgaacttcc tgcagct                                                     17

<210> SEQ ID NO 47
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 47
cgtcaacgag tgggagcgca cg                                               22

<210> SEQ ID NO 48
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 48
gtccgactcc cgctgcaagg act                                              23

<210> SEQ ID NO 49
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 49
tgcaggatct cggacttctg cagctt                                           26

<210> SEQ ID NO 50
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 50
gaccaatcag tggtcgccct g                                                21

<210> SEQ ID NO 51

```
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 51
atggggttgt aagagtccag ggc                                           23

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
cgtgccccgt aaccgcatcg                                               20

<210> SEQ ID NO 53
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 53
ctcatggggg cgctgggcg                                                19

<210> SEQ ID NO 54
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 54
gccctcccag catggcaa                                                 18

<210> SEQ ID NO 55
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 55
gtcacctccg ccctgcactc agt                                           23

<210> SEQ ID NO 56
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 56
gccctcccag catggcaa                                                 18

<210> SEQ ID NO 57
<211> LENGTH: 23
<212> TYPE: DNA
<213> ORGANISM: Artificial Sequence
<220> FEATURE:
<223> OTHER INFORMATION: synthetic oligonucleotide
```

```
<400> SEQUENCE: 57
gtcacctccg ccatgcactc agt                                          23

<210> SEQ ID NO 58
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 58
gccctcccag catggcaa                                                18

<210> SEQ ID NO 59
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 59
gtcacctccg ccatggactc agt                                          23

<210> SEQ ID NO 60
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 60
tgaacggtgc tgtcatgtac cagatc                                       26

<210> SEQ ID NO 61
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 61
tgacgtggag gacacacatc tcgcc                                        25

<210> SEQ ID NO 62
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 62
gcagccagat cccgcgccta gcggggctg                                    29

<210> SEQ ID NO 63
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 63
cagccccgct aggcgcggga tctggctgc                                    29

<210> SEQ ID NO 64
```

```
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 64
gggcctgctg cgcattcctg cccctgca                                    28

<210> SEQ ID NO 65
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 65
tgcaggggca ggaatgcgca gcaggccc                                    28

<210> SEQ ID NO 66
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 66
ctcccagcat ggcaacgcca ccttcagcta cac                              33

<210> SEQ ID NO 67
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 67
gtgtagctga aggtggcgtt gccatgctgg gag                              33

<210> SEQ ID NO 68
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 68
cccaaggtca tggaggccct cattgaattc gcct                             34

<210> SEQ ID NO 69
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 69
aggcgaattc aatgagggcc tccatgacct tggg                             34
```